(12) United States Patent
Miura et al.

(10) Patent No.: US 11,975,002 B2
(45) Date of Patent: May 7, 2024

(54) PREPARATION AND COMPOSITION FOR TREATMENT OF MALIGNANT TUMORS

(71) Applicant: TAIHO PHARMACEUTICAL CO., LTD., Tokyo (JP)

(72) Inventors: Akihiro Miura, Tsukuba (JP); Hiroshi Sootome, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 127 days.

(21) Appl. No.: 16/082,117

(22) PCT Filed: Mar. 3, 2017

(86) PCT No.: PCT/JP2017/008599
§ 371 (c)(1),
(2) Date: Sep. 4, 2018

(87) PCT Pub. No.: WO2017/150725
PCT Pub. Date: Sep. 8, 2017

(65) Prior Publication Data
US 2020/0281927 A1 Sep. 10, 2020

(30) Foreign Application Priority Data
Mar. 4, 2016 (JP) ................ 2016-042662

(51) Int. Cl.
*A61K 31/5025* (2006.01)
*A61K 33/243* (2019.01)
*A61K 45/06* (2006.01)

(52) U.S. Cl.
CPC ........ *A61K 31/5025* (2013.01); *A61K 33/243* (2019.01); *A61K 45/06* (2013.01)

(58) Field of Classification Search
CPC ... A61K 31/5025; A61K 33/243; A61K 45/06
See application file for complete search history.

(56) References Cited

U.S. PATENT DOCUMENTS

| | | | |
|---|---|---|---|
| 4,724,141 A | 2/1988 | Schmidt et al. | |
| 8,772,238 B2 | 7/2014 | Francischetti et al. | |
| 9,108,973 B2 | 8/2015 | Sagara et al. | |
| 9,725,723 B2 | 8/2017 | Hedtjarn et al. | |
| 10,124,003 B2 * | 11/2018 | Sootome | A61K 31/437 |
| 10,835,536 B2 * | 11/2020 | Sootome | A61P 35/00 |
| 10,894,048 B2 * | 1/2021 | Ochiiwa | A61P 35/00 |
| 2002/0168413 A1 | 11/2002 | Stamm et al. | |
| 2004/0102360 A1 | 5/2004 | Barnett et al. | |
| 2006/0110383 A1 | 5/2006 | Honjo et al. | |
| 2007/0254033 A1 | 11/2007 | Bhatt et al. | |
| 2007/0299075 A1 | 12/2007 | Bhide et al. | |
| 2008/0026057 A1 | 1/2008 | Benke | |
| 2008/0207665 A1 | 8/2008 | Hashizume et al. | |
| 2010/0025143 A1 | 2/2010 | Gustavsson et al. | |
| 2010/0048620 A1 | 2/2010 | Yamamoto | |
| 2010/0285143 A1 | 11/2010 | Khedkar et al. | |
| 2011/0053866 A1 | 3/2011 | Duffield et al. | |
| 2012/0010164 A1 | 1/2012 | Summa et al. | |
| 2012/0101064 A1 | 4/2012 | Howard et al. | |
| 2013/0061403 A1 | 3/2013 | Bringewatt et al. | |
| 2013/0158000 A1 | 6/2013 | Brohm et al. | |
| 2013/0190354 A1 | 7/2013 | Hong et al. | |
| 2014/0005185 A1 | 1/2014 | Nakamura et al. | |
| 2014/0343035 A1 | 11/2014 | Sagra et al. | |
| 2015/0031676 A1 | 1/2015 | Lobell et al. | |
| 2015/0164909 A1 | 6/2015 | Koji et al. | |
| 2015/0166544 A1 | 6/2015 | Zhang et al. | |
| 2015/0307886 A1 | 10/2015 | Hedtjarn et al. | |
| 2016/0090633 A1 * | 3/2016 | Platero | C12Q 1/6886 506/2 |
| 2016/0102366 A1 | 4/2016 | Tetsuya et al. | |
| 2016/0136168 A1 | 5/2016 | Sootome | |
| 2016/0193210 A1 | 7/2016 | Ochiiwa et al. | |
| 2016/0287699 A1 | 10/2016 | Karkera et al. | |

(Continued)

FOREIGN PATENT DOCUMENTS

AU 2018448845 A1 6/2021
AU 2020228514 A1 10/2021

(Continued)

OTHER PUBLICATIONS

Mimura; Cancer Res, 2014,74 (16), 4458-4469. DOI: 10.1158/0008-5472.CAN-13-3652 (Year: 2014).*
Borad et al., "Fibroblast growth factor receptor 2 fusions as a target for treating cholangiocarcinoma", Curr Opin Gastroenterol, 2015, vol. 31(3), pp. 264-268.
Official Action of RU Pat. Appln. No. 2018134777, dated Jun. 1, 2020, 22 pages.
Caira M R, "Crystalline Polymorphism of Organic Compounds", Topics in Current Chemistry, 1998, vol. 198, pp. 163-208.
Office Action dated Feb. 5, 2019 for the corresponding MX patent application No. MX/a/2017/012568, 9 pages.
Hernandez et al., "Prospetvice Study of FGFR3 Mutations as a Prognostic Factor in Nonmuscle invasive Urothelial Bladder Carcinomas", Journal of Clinical Oncology, 2006, vol. 24, No. 22, pp. 3664-3671.

(Continued)

*Primary Examiner* — Daniel R Carcanague
(74) *Attorney, Agent, or Firm* — Rothwell, Figg, Ernst & Manbeck, P.C.

(57) ABSTRACT

It is intended to provide a novel method for treating a cancer using an FGFR inhibitor that exhibits a remarkably excellent antitumor effect and has fewer side effects. The present invention provides a combination preparation for the treatment of a malignant tumor comprising a compound represented by Formula (I) or a pharmaceutically acceptable salt thereof, and one or more additional compound(s) having an antitumor effect or pharmaceutically acceptable salt(s) thereof, and a pharmaceutical composition comprising both the active ingredients. The present invention also provides an antitumor effect enhancer, an antitumor agent, a kit for malignant tumor treatment, etc. comprising a compound represented by Formula (I) or a pharmaceutically acceptable salt thereof.

30 Claims, 32 Drawing Sheets

(56) References Cited

U.S. PATENT DOCUMENTS

| | | | |
|---|---|---|---|
| 2017/0035773 A1 | 2/2017 | Tomimatsu et al. | |
| 2017/0112894 A1 | 4/2017 | Kawabe | |
| 2017/0209574 A1 | 7/2017 | Cao et al. | |
| 2017/0252317 A1 | 9/2017 | Lyssikatos et al. | |
| 2017/0260168 A1* | 9/2017 | Andrews | A61K 31/5377 |
| 2018/0030067 A1 | 2/2018 | Masaya et al. | |
| 2018/0110782 A1 | 4/2018 | Egami | |
| 2018/0177788 A1 | 6/2018 | Pachter et al. | |
| 2019/0015417 A1* | 1/2019 | Sootome | A61K 31/519 |
| 2019/0183897 A1* | 6/2019 | Ochiiwa | A61P 43/00 |
| 2019/0224341 A1* | 7/2019 | Choi | A61K 47/6951 |
| 2019/0350932 A1 | 11/2019 | Miura et al. | |
| 2020/0168413 A1 | 5/2020 | Kang et al. | |
| 2021/0030755 A1* | 2/2021 | Kusumoto | A61K 9/48 |

FOREIGN PATENT DOCUMENTS

| | | | |
|---|---|---|---|
| AU | 2020229714 A1 | 10/2021 | |
| CN | 105859721 A | 8/2016 | |
| EA | 200970932 A1 | 4/2010 | |
| EA | 201101566 A1 | 5/2012 | |
| EP | 3138842 A1 | 3/2017 | |
| EP | 3279202 A1 | 7/2018 | |
| EP | 3888643 A1 | 6/2021 | |
| EP | 3882248 A1 | 9/2021 | |
| JP | S61-068431 A | 4/1986 | |
| JP | H11-005735 A | 1/1999 | |
| JP | 2009-143967 A | 7/2009 | |
| JP | 2011511759 A | 4/2011 | |
| JP | 2011-524888 A | 9/2011 | |
| JP | 2013079267 A | 5/2013 | |
| JP | 2015500307 A | 1/2015 | |
| JP | 2015508087 A | 3/2015 | |
| JP | 2016-501520 A | 1/2016 | |
| JP | 2016104762 A | 9/2016 | |
| JP | 2017-518276 A | 7/2017 | |
| JP | 2018-002662 A | 1/2018 | |
| JP | 2018511611 A | 4/2018 | |
| JP | 2018519327 A | 7/2018 | |
| JP | 2018537420 A | 12/2018 | |
| KR | 10-2009-0108100 A | 10/2009 | |
| RU | 2173157 C2 | 9/2001 | |
| RU | 2009127883 A | 1/2009 | |
| RU | 2493850 A | 7/2009 | |
| RU | 2428421 C2 | 9/2011 | |
| RU | 25958662 C2 | 10/2011 | |
| WO | 02/06213 A2 | 1/2002 | |
| WO | 03/077914 A1 | 9/2003 | |
| WO | 2004004771 A1 | 1/2004 | |
| WO | 2005/051906 A2 | 6/2005 | |
| WO | 2005/121142 A1 | 12/2005 | |
| WO | 2006/045514 A1 | 5/2006 | |
| WO | 2007/014011 A2 | 2/2007 | |
| WO | 2007/044515 A1 | 4/2007 | |
| WO | 2007041712 A1 | 4/2007 | |
| WO | 2007087395 A2 | 8/2007 | |
| WO | 2008077557 A1 | 12/2007 | |
| WO | 2008/124161 A1 | 10/2008 | |
| WO | 2008121742 A2 | 10/2008 | |
| WO | 2009153592 A1 | 12/2009 | |
| WO | 2010043865 A1 | 4/2010 | |
| WO | 2011093672 A2 | 8/2011 | |
| WO | 2011115937 A1 | 9/2011 | |
| WO | 2011153514 A2 | 12/2011 | |
| WO | 2012137870 A2 | 10/2012 | |
| WO | 2013/087725 A1 | 6/2013 | |
| WO | 2013108809 A1 | 7/2013 | |
| WO | 2013116293 A1 | 8/2013 | |
| WO | 2014007217 A1 | 1/2014 | |
| WO | 2015008844 A1 | 7/2014 | |
| WO | 2014138364 A1 | 9/2014 | |
| WO | 2014172644 A1 | 10/2014 | |
| WO | 2014203959 A1 | 12/2014 | |
| WO | 2015008839 A1 | 1/2015 | |
| WO | 2015/150900 A2 | 10/2015 | |
| WO | 2016115356 A1 | 7/2016 | |
| WO | 2016/130917 A1 | 8/2016 | |
| WO | 2016125169 A1 | 8/2016 | |
| WO | 2016136928 A1 | 9/2016 | |
| WO | 2016159327 A | 10/2016 | |
| WO | 2016159327 A1 | 10/2016 | |
| WO | 2016161239 A1 | 10/2016 | |
| WO | 2017017516 A1 | 2/2017 | |
| WO | 2017/086332 A1 | 5/2017 | |
| WO | 2017150725 A | 9/2017 | |
| WO | 2017150725 A1 | 9/2017 | |
| WO | 2018130928 A1 | 7/2018 | |
| WO | 2019/051296 A1 | 3/2019 | |
| WO | 2019/181876 A1 | 9/2019 | |
| WO | 2020/095452 A1 | 5/2020 | |
| WO | 2020/096042 A1 | 5/2020 | |
| WO | 2020/096050 A1 | 5/2020 | |
| WO | 2020/110974 A1 | 6/2020 | |
| WO | 2020/170355 A1 | 8/2020 | |
| WO | 2020/171113 A1 | 8/2020 | |
| WO | 2020/175697 A1 | 9/2020 | |
| WO | 2020/175704 A1 | 9/2020 | |
| WO | 2020/256096 A1 | 12/2020 | |

OTHER PUBLICATIONS

Gelsi-Boyer et al., "Comprehensive Profiling of 8p11-12 Amplification in Breast Cancer", Molecular Cancer Research, 2005, vol. 3, No. 12, pp. 655-667.

Turner et al., "FGFR1 Amplification Drives Endocrine Therapy Resistance and is a Therapeutic Target in Breast Cancer", Cancer Research, 2010, vol. 70, No. 5, pp. 2085-2094.

Wilson et al., "Widespread potential for growth-factor-driven resistance to anticancer kinase inhibitors", Nature, 2012, 487(7408): 505-509.

Chang et al., "Multiple receptor tyrosine kinase activation attenuates therapeutic efficacy of the fibroblast growth factor receptor 2 inhibitor AZD4547 in FGFR2 amplified gastric cancer", Oncotarget, vol. 6, No. 4, pp. 2009-2022.

Kleespies et al., "Tyrosine kinase inhibitors and gemcitabine: New treatment options in pancreatic cancer?", Drug Resistance Updates, 2006, pp. 1-18.

Office Action dated Apr. 24, 2018 for the corresponding RU patent application No. 2017134584.

Decision of Refusal for the corresponding JP patent application No. 2017-149671, 8 pages, dated May 15, 2018.

Lectures of Experimental Chemistry (continued) 2 Separation and purification, 1967, pp. 159-162, 184-193.

Handbook of Solvents, 1985, pp. 47-51.

Version 4 Lectures on experimental chemistry 1 Basic operation I, 1990, pp. 184-189.

Impurities: Guideline for Residual Solvents, 1998, No. 307, pp. 1-11.

Office Action for the corresponding RU patent application No. 2016105133, dated Feb. 2, 2017.

Folkman, "Angiogenesis in cancer, vascular, rheumatoid and other diseases", Nature Medicine, 1995, vol. 1, No. 1, pp. 27-31.

Lieu et al., "Beyond VEGF: Inhibition of the fibroblast growth factor pathway and antiangiogenesis", Clinical Cancer Research, 2011, vol. 17, No. 19, pp. 6130-6139.

International Search Report from PCT/JP2013/050740, dated Aug. 30, 2013, 7 pages.

Gong et al., "A novel 3-arylethynyl-substituted pyrido[2,3-b]pyrazine derivatives and pharmacophore model as Wnt2/β-catenin pathway inhibitors in a non-small-cell lung cancer cell lines", Bioorganic &Medicinal Chemistry, vol. 19, 2011, pp. 5639-5647.

Yuki Kagobutsu Kessho Sakusei Handbook—Genri to Know-how—, Maruzen Co., Ltd., 2008, pp. 57-84.

Office Action for the JP patent application No. 2016-566309, date of drafting Feb. 2, 2017, 3 pages.

Byrn et al., "Pharmaceutical Solids: A Strategic Approach to Regulatory Considerations", Pharmaceutical Research, 1995, 12(7), pp. 945-954.

(56) References Cited

OTHER PUBLICATIONS

Bavin et al., "Polymorphism in Process Development", Chemistry & Industry, 1989, (16), pp. 527-529.

Keiko Toyo Seizai no Sekkei to Hyoka, Kabushiki Kaisha Yakugyo Jihosha, 1995, pp. 76-79, 171-172.

Sootome et al., "Identification and Biological Charaacterization of a Highly Potent, Irreversible Inhibitor of FGFR, TAS-2985", European Journal of Cancer, 48:116, 2012.

Nakatsuru et al., "Significant in Vivo Antitumor Activity by a Highly Potent, Irreversible FGFR Inhibitor, TAS-2985", European Journal of Cancer, 2012, vol. 48, Suppl. 6, pp. 117.

Gangjee et al., "Synthesis of 5,7-disubstituted-4-methyl-7H-pyrrolo[2,3-d]pyrimidin-2-amines as microtubule inhibitors", Bioorganic & Medicinal Chemistry, 2013, 3, vol. 21, No. 5, pp. 1180-1189.

Fukumoto et al., "FGF23 is a hormone-regulating phosphate metabolism-Unique biological characteristics of FGF23", Bone, 2007, vol. 40, pp. 1190-1195.

Shimada et al., "Targeted ablation of Fgf23 demonstrates an essential physiological role of FGF23 in phosphate and vitamin D metabolism", Journal of Clinical Investigation, 2004, vol. 113, No. 4, pp. 561-568.

Razzaque et al., "FGF-23, vitamin D and calcification: the unholy triad", Nephrol. Dial. Transplant., 2005, vol. 20, pp. 2032-2035.

Jonker et al., "A phase I study to determine the safety, pharmacokinetics and pharmaodynamics of a dual VEGFR an FGFR inhibitor, brivanib, in patients with advanced or metastatic solid tumors", Annals of Oncology 22: pp. 1413-1419, 2011.

Pharmacodia (http://en.pharmacodia.com/web/drug/1_1258.html, retrieved Jun. 10, 2017).

Cayman (https://www.caymanchem.com/product/21136 , retrieved Jun. 10, 2017).

Konecny et al., "Activity of the Fibroblast Growth Factor Receptor Inhibitors Dovitinib (TK1258) and NVP-BGJ398 in Human Endometrial Cancer Cells", Molecular Cancer Therapeutics 12(5); 632-642, 2013.

Xie et al., "FGFR2 Gene Amplification in Gastric Cancer Predicts Sensitivity to the Selective FGFR Inhibitor AZD4547", Clinical Cancer Research, vol. 19, No. 9, pp. 2572-2583 (2013).

Byron et al., "Fibroblast Growth Factor Receptor Inhibition Synergizes with Paclitaxel and Doxorubicin in Endometrial Cancer Cells", International Journal of Gynecological Cancer, vol. 22, No. 9, pp. 1517-1526 (2012).

Formisano et al., "Association of FGFR1 with Eralpha Maintains ligands-Independent ER Transcription and Mediates Resistance to Estrogen Deprivation in ER+ Breast Cancer", Clinical Cancer Research, 2017, vol. 23, Issue 20, pp. 6138-6150.

Sobhani et al., "Current Status of Fibroblast Growth Factor Receptor-Targeted Therapies in Breast Cancer", cells. 2018, vol. 7, Issue 7, Art. No. 76, pp. 1-14.

Andre, "Rationale for targeting fibroblast growth factor receptor signaling in breast cancer", Breast Cancer Research and Treatment, 2015, vol. 150, Issue 1, pp. 1-8.

Chae, "Inhibition of the fibroblast growth factor receptor (FGFR) pathway: the current landscape and barriers to clinical application", Oncotarget, 2017, vol. 8, No. 9, pp. 16052-16074.

Perez-Garcia et al., "Targeting FGFR pathway in breast cancer", The Breast, 2018, vol. 37, pp. 126-133.

Musolino et al., "Phase II, randomized placebo-controlled study of dovitinib in combination with fulvestrant in postmenopausal patients with HR+, HER2-breast cancer that had progressed during or after prior endocrine therapy", Breast Cancer Research, 2017, vol. 19, Art. No. 18, pp. 1-14.

Li et al., "Novel EGFR inhibitors prepared by combination of dithiocarbamic acid esters and 4-anilinoquinazolines", Bioorg. Med. Chem. Lett. 21, 2011, pp. 3637-3640, S1-S27.

Kubinyi, "3D QSAR in Drug Design: Ligand-Protein interactions and Molecular Similarity", vol. 2-3,1998, pp. 243-244.

Wermuth, "The Practice of Medicinal Chemistry, 2d ed.", 2003, Chs. 9-10.

Office Action for U.S. Appl. No. 16/274,573, dated Mar. 13, 2020, 17 pages.

Patani et al., "Landscape of activating cancer mutations in FGFR kinases and their differential responses to inhibitors in clinical use", Oncotarget, 2016, vol. 7, No. 17, pp. 24252-24268.

Singh et al., "Transforming Fusions of FGFR and TACC Genes in Human Glioblastoma", Science, 2012, vol. 337, pp. 1231-1235.

Brown et al., "Maximising the potential of AKT inhibitors as anti-cancer treatments", Pharmacology & Therapeutics, 2017, vol. 172, pp. 101-115.

Yunokawa et al., "First-in-human phase I study of TAS-117, an allosteric AKT inhibitor, in patients with advanced solid tumours", Annals of Oncology, 2019, vol. 30, Suppl. 5, p. v169.

Byron et al., "The N550K/H Mutations in FGFR2 Confer Differential Resistance to PD173074, Dovitinib, and Ponatinib ATP-Competitive Inhibitors", Neoplasia, vol. 15, No. 8, pp. 975-988, 2013.

Office Action dated Jun. 26, 2019 cited in U.S. Appl. No. 16/149,522, 19 pages.

Belikov V.G., Pharmaceutical Chemistry in Two Parts, "Pharmaceutical Chemistry", 1993, 432 pp. 43-47.

Mashkovsky M.D., Medicinal media—16th ed., Revised—M .: Novaya Volna, 2012.—1216 p.

"Mashkovsky M.D. Medicaments, Moscow, NewWave, 2001, in 2 parts, vol. 1, p. 11".

Official Action for RU Pat. Appln. No. 2018134777 dated Apr. 28, 2021.

Turner et al., "Fibroblast growth factor signalling: from development to cancer", Nature Reviews Cancer, 2010, vol. 10, pp. 116-129.

Elsheikh et al., "FGFR1 amplification in breast carcinomas: a chromogenic in situ hybridisation analysis", Breast Cancer Research, 2007, vol. 9, No. 2, R23.

Corn et al., "Targeting Fibroblast Growth Factor Pathways in Prostate Cancer", Clin. Cancer Res., 2013, 19(21), pp. 5856-5866.

"Boget et al., ""Fibroblast growth factor receptor 1 (FGFR1) is over-expressedin benign prostatic hyperplasia whereas FGFR2-IIIC and FGFR3are not"", European Journal of Endocrinology, 2001, 145, pp. 303-310".

"Bluemn et al., ""Androgen Receptor Pathway-Independent ProstateCancer Is Sustained through FGF Signaling"", Cancer Cell, 2017, 32, pp. 474-489".

Jones et al., "Recurrent somatic alterations of FGFR1 and NTRK2 in pilocytic astrocytoma", Nature Genetics, 2013, vol. 45, No. 8, pp. 927-932.

Pardoll, "The blockade of immune checkpoints in cancer immunotherapy", Nature Reviews Cancer, vol. 12, 2012.

Topalian et al., "Safety, Activity, and Immune Correlates of Anti-PD-1 Antibody in Cancer", The New England Journal of Medicine, vol. 366, No. 26, 2012, pp. 2443-2454.

Sharma et al., "Primary, Adaptive, and Acquired Resistance to Cancer Immunotherapy", CELL, vol. 168, 2017, pp. 707-723.

Zaretsky et al., "Mutations Associated with Acquired Resistance to PD-1 Blockade in Melanoma", The New England Journal of Medicine, vol. 375, No. 9, 2016, pp. 819-829.

Arlauckas et al., "In vivo imaging reveals a tumor-associated macrophage-mediated resistance pathway in anti-PD-1 therapy", Science Translational Medicine, 9, eaal3604, 2017.

Nassar et al., "Sequential Response to FGFR3 Inhibition With Subsequent Exceptional Response to Atezolizumab in a Patient With FGFR3-TACC3 Fusion-Positive Metastatic Urothelial Carcinoma", JCO Precision Oncology, DOI: 10.1200/P0.18.00117, 2018.

Liu et al., "Reductions in Myeloid-Derived Suppressor Cells and Lung Metastases using AZD4547 Treatment of a Metastatic Murine Breast Tumor Model", Cellular Physiology and Biochemistry, 33, pp. 633-645, 2014.

Weber et al., "Myeloid-Derived Suppressor Cells Hinder the Anti-Cancer Activity of immune Checkpoint inhibitors", frontiers in Immunology, vol. 9, art. 1310, 2018.

"Manning et al., ""AKT/PKB Signaling:Navigating Downstream""", CELL, 2007, 129, pp. 1261-1274".

(56) References Cited

OTHER PUBLICATIONS

"Markman et al., ""Status of PI3K inhibition and biomarker development in cancer therapeutics"", Annals of Oncology 2010, 21: pp. 683-691".

"Yap et al., ""First-in-Man Clinical Trial of the Oral Pan-AKT InhibitorMK-2206 in Patients With Advanced Solid Tumors"", Journal of Clinical Oncology, 2011, vol. 29, No. 35, pp. 4688-4695".

"Saleh et al., ""Abstract LB-197: First-in-human study with ARQ092, a novel pan AKT-inhibitor: Results from theadvanced solid tumors cohorts."", 2013, 73 (Suppl 8)".

Banerji et al., "A Phase 1 open-label study to identify a dosing regimen of the pan-AKT inhibitor AZD5363 for evaluation in solid tumors and in PIK3CA-mutated breast and gynecologic cancers", 2018, (9): 2050-2059, (doi 10.1158/1078/0432. CRC-17-2260).

Abe et al., "Characterization of TAS-117, a novel, highly potent and selective inhibitor of AKT", 2017, Poster of EORTC-NCI-AACR 2017.

Offical Action for RU Patent Application No. 2020133810, dated Feb. 16, 2021, 20 pages.

Li-Hua et al. "Drug-excipient interactions resulting from powder mixing. V. Role of sodium lauryl sulfate", International Journal of Pharmaceutics, vol. 60, No. 1, 1990, pp. 61-78.

Extended European search report dated Nov. 11, 2021 for EP Pat. Appln. 19771998.2, 13 pgs.

Kharkevich, Pharmacology: textbook, 10th ed , 2010, pp. 72-82.

Urmancheeva et al., Modern hormone therapy of endometrial cancer, Siberian Oncological Journal, 2007, Appendix, pp. 89-93.

Chissov et al., Oncology: textbook with CD, GEOTAR-Media, 2007 pp. 106-107.

Tarutinov V.I. et al., Hormone therapy in breast cancer: current state of the problem. // Oncology. vol. 9, 2, 2007, pp. 125-128.

Vorobyeva L.I. et al., Hormonal carcinogenesis and the rationale for the use of hormone therapy in the treatment of patients with ovarian cancer (literature review) // Clinical oncology, 1 (9), 2013, pp. 56-64.

Kaprin A.D. et al., The role of hormone therapy in the complex treatment of localized and locally advanced prostate cancer// Russian Medical Journal, 28, 2006, 13 pages.

Office Action dated Feb. 28, 2022 for RU Pat. Appln. No. 2021118562, 42 pages.

Shaabani et al., "A patent review on PD-1/PD-L1 antagonists: small molecules, peptides and macrocycles (2015-2018)", Expert Opin Ther Pat. 2018, 28(9), 665-678.

Tol et al., "Chemotherapy, Bevacizumab, and Cetuximab in Metastatic Colorectal Cancer", The New England Journal of Medicine, 2009; 360: 563-72.

Yu et al., "A phase 1/2 trial of ruxolitinib and erlotinib in patients with EGFR-mutant lung adenocarcinomas with acquired resistance to erlotinib", J Thorac Oncol. 2017, 12(1): 102-109.

Official Action dated Apr. 4, 2022 for RU Pat. Appln. 2021128137, 21 pages.

Ochiiwa et al., "Abstract A270: TAS-120, a highly potent and selective irreversible FGFR inhibitor, is effective in tumors harboring various FGFR gene abnormalities", Molecular Cancer Therapeutics, vol. 12, No. 11_Supplement, 2013, p. A270.

Balko et al., "Discordant Cellular Response to Presurgical Letrozole in Bilateral Synchronous ER+ Breast Cancers with a KRAS Mutation or FGFR1 Gene Amplication", Molecular Cancer Therapeutics, vol. 11, No. 10, 2012, pp. 2301-2305.

EESR dated Jul. 22, 2022 for EP patent application No. 19888521.2, 9 pages.

Katoh, Masaru; FGFR inhibitors: Effects on cancer cells, tumor microenvironment and whole-body homeostasis (Review), International Journal of Molecular Medicine, 2016, vol. 38, pp. 3-15.

Notice of Reasons for Refusal for the related JP Patent Application No. 2021-502667, dated Aug. 25, 2022, 9 pages with translation.

Kalyukina et al., "TAS-120 Cancer Target Binding: Defining Reactivity and Revealing the First Fibroblast Growth Factor Receptor 1 (FGFR1) Irreversible Structure", ChemMedChem 14, 2019, 494-500.

Meric-Bernstam et al., "Efficacy of TAS-120 an irreversible fibroblast growth factor receptor (FGFR) inhibitor, in cholangiocarcinoma patients with FGFR pathway alternations who were previously treated with chemotherapy and other FGFR inhibitors", Annals of Oncology 29 (Supplement 5), 2018, v100-v110.

Bockorny et al., "RAS-MAPK Reactivation Facilitates Acquired Resistance in FGFR1-Amplified Lung Cancer and Underlies a Rationale for Upfront FGFR-MEK Blockade", Molecular Cancer Therapeutics, 17(7), 2018, pp. 1526-1539.

ISR and Written Opinion for PCT/JP2021/0105032, May 11, 2021, 9 pgs. with translation.

Orinitz et al., "Achondroplasia: Development, Pathogenesis, and Therapy", Developmental Dynamics, 2017, 246 (4), 291-309.

Bellys et al., "Distinct Missense Mutations of the FGFR3 Lys650 Codon Modulate Receptor Kinase Activation and the Severity of the Skeletal Dylplasia Phenotype", Am J Hum Genet., 2000, 67 (6), 1411-21.

Rousseau et al., "Mutations in the gene encoding fibroblast growth factor receptor-3 in achondroplasia", Nature, 1994, 371 (6494), 252-4.

Bellus et al., "A recurrent mutation in the tyrosine kinase domain of fibroblast growth factor receptor 3 causes hypochondroplasia", Nature Genetics, 1995, 10 (3), 357-9.

Bonaventure et al., "Common Mutations in the Fibroblast Growth Factor Receptor 3 (FGFR 3) Gene Account for Achondroplasia, Hypochondroplasia, annd Thanatophoric Dwarfism", American Journal of Medical Genetics, 1995, 63 (1), 148-54.

Komla-Ebri et al., "Tyrosine kinase inhibitor NVP-BGJ398 functionally improves FGFR3-related dwarfism in mouse model", J Clin Invest., 2016, vol. 126, No. 5, pp. 1871-1884.

Garcia et al., Postnatal soluble FGFR3 therapy rescues achondroplasia symptoms and restores bone growth in mice, Sci Transl Med., 2013, vol. 5, No. 203, Art. 203ra124.

Ramaswami et al., Genotype and phenotype in hypochondroplasia, J Pediatr, 1998, vol. 133, No. 1, pp. 99-102.

Kimura et al., The incidence of thanatophoric dysplasia mutations in FGFR3 gene is higher in low-grade or superficial bladder carcinomas, Cancer, 2001, vol. 92, No. 10, pp. 2555-2561.

ISR and Written Opinion of PCT/JP2021/033133, dated Mar. 16, 2021, 16 pages with translation.

Lattanzi et al., "Current Status and Future Direction of Immunotherapy in Urothelial Carcinoma", Current Oncology Reports, vol. 21, No. 3, 2019, pp. 1-12.

EESR dated Nov. 4, 2022 for EP Patent Application No. 20763207. 6, 9 pages.

He et al., "Development of a rapidly dispersing tablet of a poorly wettable compound—formulation DOE and mechanistic study of effects of formulation excipients on wetting of celecoxib", International Journal of Pharmaceutics, vol. 353, Issues 1-2, 2008, pp. 176-186.

Bathool et al., "Development and evaluation of microporous osmotic tablets of diltiazem hydrochloride", Journal of Advanced Pharmaceutical Technology & Research, vol. 3, issues 2, 2012, pp. 124-129.

Israr et al., "Formulation design and evaluation of Cefuroxime axetil 125 mg immediate release tablets using different concertration of sodium lauryl sulphate as solubility enhancer", Brazilian Journal of Pharmaceutical Sciences, vol. 50, n. 4, Oct./Dec. 2014.

OA dated Nov. 22, 2022 for U.S. Appl. No. 16/982,377, 19 pages.

Request for the Submission of an Opinion issued in KR10-2022-7025906 dated Jan. 6, 2023, 11 pages.

Mashkovsky M.D. Drugs, Moscow, Medicine, 1993, part 1, p. 8.pdf (3 pgs.).

Richard J. Bastin et al, "Salt Selection and Optimisation Procedures for Pharmaceutical New Chemical Entities", Organic Process Research & Development, 2000, 4, 427-435.

Vengerovsky, "Pharmacological incompatibility", Bulletin Siberian Medicine, 3, 2003, pp. 49-56.

OA dated Feb. 7, 2023 for RU Pat. Appl. 2021128138, 32 pages.

(56) References Cited

OTHER PUBLICATIONS

"Chemical Encyclopedia Dictionary", Soviet Encyclopedia, 1983, pp. 130-131.
Belikov V.G. "Pharmaceutical chemistry", 2007, MEDpress-inform, pp. 27-29.
Kholodov L.E. et al. "Clinical pharmacokinetics", Medicine, 1985, pp. 83-98, 134-138, 160, 378-380.
Wesserling et al, "Will In Vitro Tests Replace Animal Models in Experimental Oncology", Journal of tissue science and engineering, 2011, V.2, No. 1, 102e, 4 pgs.
Szajewska, "Evidence-based medicine and clinical research: both are needed, neither is perfect", Annals of nutrition and metabolism, 2018, V.72, N.3, pp. 13-23.
Sergeev, "A short course of molecular pharmacology", 1975, p. 10, 4 pgs.
Russian Office Action issued in 2021118562 dated Feb. 28, 2023, 23 pgs.
Harris, "TAS-117 shows Limited Efficacy in Ovarian, Breast Tumors", 2021, Retrived from the internet: https://www.onclive.com/view/tas-117-shows-limited-efficacy-in-ovarian-breast-tumors, 2 pgs.
Lee et al., "Phase 2 study of TAS-117, an allosteric akt inhibitor in advanced solid turmors harboring phosphatidylinositol 3-kinase/v-akt murine thyroma viral ocogene homolog gene mutations", Investigational New Drugs, 2021, vol. 39, No. 5, pp. 1366-1374.
Extended European Search Report cited in 20827927.3-1112 dated Jun. 1, 2023, 13 pgs.
Shim, "One target, different effects: a comparison of distinct antibodies against the same targets", Experimental and Molecular Medicine, 2011, vol 43, No. 10, 539-549.
OA dated Jun. 29, 2023 for RU Pat. Appl. 2021128137, 13 pgs.
Jain et al., "Effect of pH-Sodium Lauryl Sulfate Combination on Solubilization of PG-300995 (an Anti-HIV Agent): A Technical Note", AAPS Pharma Sci Tech, 2004, 5(3), pp. 1-3.
Hearing Notice dated Oct. 12, 2023 for IN Pat. Appl. 202017041678 (2 pages).
Office Action dated Sep. 19, 2023 for RU Pat. Appl. 2022101214, 13 pgs.
Extended European Search Report dated Feb. 19, 2024 for EP Application No. 21747642.3, 8 pages.
DeFriend et al., "Effects of 4-hydroxytamoxifen and a novel pure antioesterogen (ICI 182780) in the clonogenic growth of human breast cancer cells in vitro," Br. J. Cancer, vol. 70, pp. 204-211 (1994).
Heo et al., "Clinical activity of fulvestrant in metastatic breast cancer previously treated with endocrine therapy and/or chemotherapy," Korean J. Intern. Med., vol. 34, pp. 1100-1106 (2019).
Request for Submission of Opinion dated Feb. 20, 2024 for KR Application No. 10-2021-7019419, 14 pages.
Li et al., "Oncogenic fusion protein FGFR2-PPHLN1: Requirements for biological activation, and efficacy of inhibitor,s" Translational Oncology, vol. 13, 100858, pp. 1-8 (2020).
Extended European Search Report dated Apr. 4, 2024 for EP Application No. 21784104.8, 10 pages.

\* cited by examiner

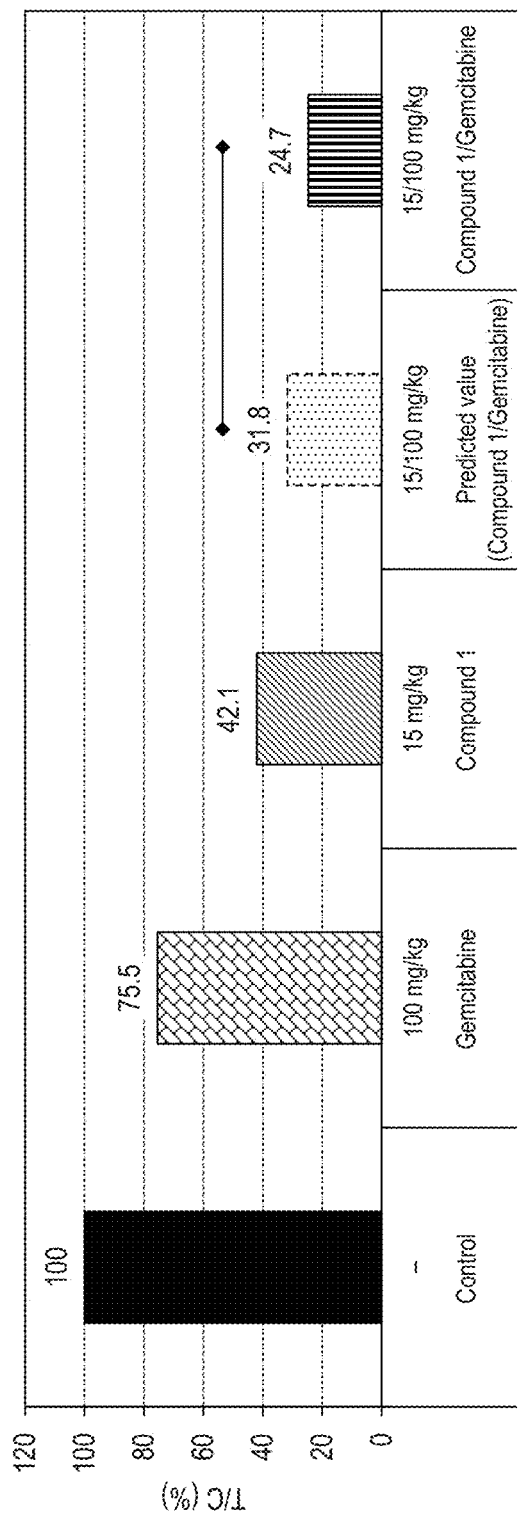

Fig. 12A

| Cell line | Tumor type | EGFR state |
|---|---|---|
| HCC4006 | NSCLC | Exon19 del |
| NCI-H1650 | NSCLC | Exon19 del |
| NCI-H322 | NSCLC | WT |

PREPARATION AND COMPOSITION FOR TREATMENT OF MALIGNANT TUMORS

CROSS REFERENCE TO RELATED APPLICATION

This application is a 35 U.S.C. 371 National Phase Entry Application from PCT/JP2017/008599, filed Mar. 3, 2017, which claims the benefit of Japanese Patent Application No. 2016-042662 filed on Mar. 4, 2016, the disclosure of which is incorporated herein in its entirety by reference.

TECHNICAL FIELD

The present invention relates to a combination preparation and a pharmaceutical composition for the treatment of a malignant tumor. More specifically, the present invention relates to a preparation and a composition for the treatment of a malignant tumor by concomitant use of a specific FGFR inhibitor and an antitumor agent.

BACKGROUND ART

As average life expectancy, has increased in recent years, cancers, i.e., malignant tumors, have occupied a high proportion of the cause of death from diseases. Methods for treating malignant tumors are broadly divided into surgical operation, radiotherapy, and chemotherapy. As medicines for use in chemotherapy, i.e., antitumor agents, antimetabolites, antitumor antibiotics, alkaloid antitumor agents, and platinum-containing drugs as well as molecular targeting drugs of antibodies or low-molecular-weight compounds have been developed.

The relation of some aberrant signaling pathways to carcinogenesis has been reported, and the relationship between aberrant fibroblast growth factor (FGF)/fibroblast growth factor receptor (FGFR) signaling and various human cancers has also been reported. Aberrant activation of FGF/FGFR signaling in human cancer is considered to be attributable to overexpression and/or gene amplification of FGFR, gene mutation chromosomal translocation or an autocrine or paracrine mechanism due to overexpression of its ligand FGFs (NPL 1, NPL 2, and NPL 3). Moreover, such aberrant signaling is considered to be partly responsible for resistance to treatment with existing chemotherapeutic antitumor agents or other receptor tyrosine kinase inhibitors in human cancer (NPL 4)

Accordingly, therapies targeted for FGF/FGFR signaling are expected to be able to provide medicines enhancing the drug effects of existing chemotherapeutic antitumor agents or molecular targeting drugs including other receptor tyrosine kinase inhibitors, or effective therapeutic remedies, alone or in concomitant use with other medicines for cancer types that are resistant or unresponsive to these drugs. A plurality of FGFR inhibitors are currently under clinical development as antitumor agents. For example, AZD4547 is being tested on concomitant use with other antitumor agents such as 5-FU, cisplatin, anti-EGFR antibody, and docetaxel (NPL 5 and NPL 6). Also, it has been suggested that concomitant use of a pyrimidine antimetabolite gemcitabine with an FGFR inhibitor is promising (NPL 7).

Meanwhile, disubstituted benzene alkynyl compounds having an FGFR inhibitory effect have been reported (PTL 1). It is also reported that these compounds are effective against cancers having a specific FGFR2 mutation (PTL 2) and that intermittent administration can be useful as a dosing schedule (PTL 3).

CITATION LIST

Patent Literature

PTL 1: WO 2013/108809
PTL 2: WO 2015/008844
PTL 3: WO 2015/008839

Non Patent Literature

NPL 1: J. Clin. Oncol. 24, 3664-3671 (2006)
NPL 2: Mol. Cancer Res. 3, 655-667 (2005)
NPL 3: Cancer Res., 2085-2094 (2010)
NPL 4: Nature. 26; 487 (7408): 505-9 (2012)
NPL 5: Clin Cancer Res. 2572-83 (2013)
NPL 6: Oncotarget. 2009-22 (2015)
NPL 7: Drug Resistance Updates 9 (2006), 1-18

SUMMARY OF INVENTION

Technical Problem

Even antitumor agents having high therapeutic effects need to be carefully used or may be unable to be used in some cases, if these agents have severe side effects or are highly toxic. It is also known that such antitumor agents may differ in effect among patients or may reduce their effects due to the long-term administration of the same agent.

An object of the present invention is to provide a novel method for treating a cancer using an FGFR inhibitor that exhibits a remarkably excellent antitumor effect and has fewer side effects.

Solution to Problem

The present inventor has studied concomitant use of a compound represented by Formula (I) and an additional compound having an antitumor effect, and consequently found that such concomitant use remarkably enhances an antitumor effect without remarkably exacerbating toxicity, as compared with the case of using the compound represented by Formula (I) or the additional compound having an antitumor effect alone.

The present invention provides the following [1] to [36]:
[1] A combination preparation for the treatment of a malignant tumor comprising a compound represented by Formula (I)

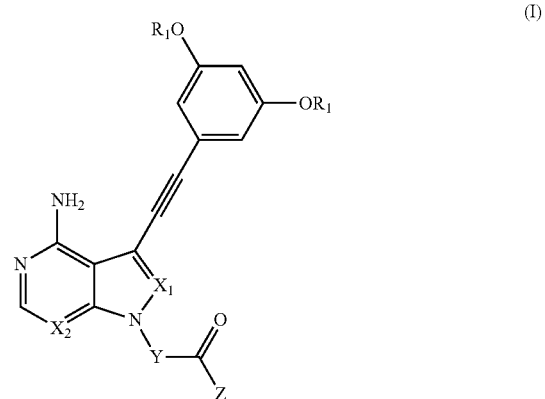

wherein $R_1$ is the same or different, and each represents $C_1$-$C_6$ alkyl;

$X_1$ and $X_2$ independently represent N or CH;

Y is a group represented by Formula (A)

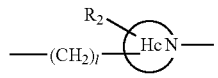

(A)

(wherein the divalent moiety represented by

is nitrogen-containing $C_3$-$C_{10}$ heterocycloalkylene), a group represented by Formula (B)

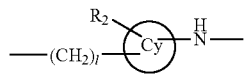

(B)

(wherein the divalent moiety represented by

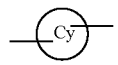

is $C_3$-$C_{10}$ cycloalkylene), or a group represented by Formula (C)

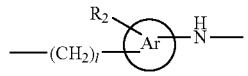

(C)

(wherein the divalent moiety represented by

is $C_6$-$C_{12}$ arylene);

$R_2$ is hydrogen, $C_2$-$C_6$ alkynyl, —C(=O)O$R_x$, —C(=O)N($R_x$)($R_y$), hydroxy-$C_1$-$C_6$ alkyl, di($C_1$-$C_6$ alkyl)amino-$C_1$-$C_6$ alkyl, or $C_2$-$C_9$ heteroaryl optionally having $R_3$;

$R_3$ is $C_1$-$C_6$ alkyl or di($C_1$-$C_6$ alkyl)amino-$C_1$-$C_6$ alkyl;

Z is —C($R_4$)=C($R_5$)($R_6$) or —C≡C—$R_7$;

$R_4$, $R_5$, and $R_6$ are the same or different, and each represents hydrogen, halogen, $C_1$-$C_6$ alkyl optionally having $R_8$, or a group represented by Formula (D)

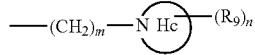

(D)

(wherein the monovalent moiety represented by

is nitrogen-containing $C_3$-$C_{10}$ heterocycloalkyl), $R_7$ is hydrogen, $C_1$-$C_6$ alkyl, or hydroxy-$C_1$-$C_6$ alkyl;

$R_8$ is —O$R_x$ or —N($R_x$)($R_y$);

$R_9$ is $C_1$-$C_6$ alkyl, halogen, or —O$R_x$;

$R_x$ and $R_y$ are the same or different, and each represents hydrogen, $C_1$-$C_6$ alkyl, $C_3$-$C_{10}$ cycloalkyl, di($C_1$-$C_6$ alkyl)amino-$C_1$-$C_6$ alkyl, or $C_1$-$C_6$ alkoxy-$C_1$-$C_6$ alkyl;

l is an integer of 0 to 3;

m is an integer of 1 to 3; and n is an integer of 0 to 2; or a salt thereof; and one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

[2] The combination preparation according to [1], wherein the compound represented by Formula (I) or the pharmaceutically acceptable salt thereof is (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or a pharmaceutically acceptable salt thereof.

[3] The combination preparation according to [1] or [2], wherein the additional compound having an antitumor effect or the pharmaceutically acceptable salt thereof is a pyrimidine antimetabolite, an alkaloid antitumor agent, a platinum-containing drug, or a molecular targeting drug.

[4] The combination preparation according to [3], wherein the pyrimidine antimetabolite is selected from the group consisting of 5-fluorouracil, tegafur/gimeracil/oteracil potassium, capecitabine, and gemcitabine.

[5] The combination preparation according to [3], wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 000.1 to 10 moles per mole of the pyrimidine antimetabolite.

[6] The combination preparation according to [3], wherein the alkaloid antitumor agent is selected from the group consisting of paclitaxel, docetaxel, irinotecan, and vinblastine.

[7] The combination preparation according to [3], wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.01 to 200 moles per mole of the alkaloid antitumor agent.

[8] The combination preparation according to [3], wherein the platinum-containing drug is selected from the group consisting of cisplatin, carboplatin, and oxaliplatin.

[9] The combination preparation according to [3], wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.001 to 50 moles per mole of the platinum-containing drug.

[10] The combination preparation according to [3], wherein the molecular targeting drug is selected from the group consisting of a low-molecular-weight molecular targeting drug and an antibody molecular targeting drug.

[11] The combination preparation according to [10], wherein the antibody molecular targeting drug is selected from the group consisting of ramucirumab and bevacizumab.

[12] The combination preparation according to [10], wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.005 to 1 mg per mg of the antibody molecular targeting drug.

[13] The combination preparation according to [10], wherein the low-molecular-weight molecular targeting drug is selected from the group consisting of everolimus, MK2206, and trans-3-amino-1-methyl-3-(4-(3-phenyl-5H-imidazo[1,2-c]pyrido[3,4-e][1,3]oxazin-2-yl)phenyl)cyclobutanol.

[14] The combination preparation according to [10], wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 1 to 1000 moles per mole of the low-molecular-weight molecular targeting drug.

[15] The combination preparation according to [1] or [2], wherein the additional compound having an antitumor effect or the pharmaceutically acceptable salt thereof is an antifolate.

[16] The combination preparation according to [15], wherein the antifolate is methotrexate.

[17] The combination preparation according to [1] or [2], wherein the additional compound having an antitumor effect or the pharmaceutically acceptable salt thereof is an alkylating agent.

[18] The combination preparation according to any of [1] to [17], wherein the compound represented by Formula (I) or the pharmaceutically acceptable salt thereof, and the additional compound having an antitumor effect or the pharmaceutically acceptable salt thereof are administered simultaneously, separately, or sequentially.

[19] The combination preparation according to any of [1] to [18], wherein the compound represented by Formula (I) or the pharmaceutically acceptable salt thereof, and the additional compound having an antitumor effect or the pharmaceutically acceptable salt thereof are administered through the same route or administered through different routes.

[20] A pharmaceutical composition comprising a compound represented by Formula (I) or a pharmaceutically acceptable salt thereof, and one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

[21] An antitumor effect enhancer for one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent, the antitumor effect enhancer comprising a compound represented by Formula (I) or a pharmaceutically acceptable salt thereof as an active ingredient.

[22] An antitumor agent comprising a compound represented by Formula (I) or a pharmaceutically acceptable salt thereof, wherein the antitumor agent is concomitantly used with one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

[23] An antitumor agent comprising a compound represented by Formula (I) or a pharmaceutically acceptable salt thereof, wherein the antitumor agent is for the treatment of a cancer patient given one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

[24] Use of a compound represented by Formula (I) or a pharmaceutically acceptable salt thereof in the manufacture of an antitumor effect enhancer for one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

[25] Use of a compound represented by Formula (I) or a pharmaceutically acceptable salt thereof in the enhancement of the antitumor effect of one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

[26] A method for treating a tumor comprising administering a compound represented by Formula (I) or a pharmaceutically acceptable salt thereof, and one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent to a patient in need thereof.

[27] A kit for malignant tumor treatment comprising a compound represented by Formula (I) or a pharmaceutically acceptable salt thereof, and one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

[28] The combination preparation according to any of [1] to [19], the pharmaceutical composition according to [20], the antitumor effect enhancer according to [21], the antitumor agent according to [22] or [23], the use according to [24] or [25], or the method according to [26], wherein the tumor is selected from the group consisting of lung cancer, esophagus cancer, gastric cancer, duodenum cancer, liver cancer, hepatocellular cancer, biliary tract cancer, pancreatic cancer, colorectal cancer, breast cancer, uterine cancer, ovarian cancer, renal cancer, bladder cancer, prostate cancer, testicular tumor, thyroid cancer, bone or soft tissue tumor, leukemia, malignant lymphoma, multiple myeloma, head and neck cancer, brain tumor, and skin cancer.

[29] The combination preparation according to any of [1] to [19], the pharmaceutical composition according to [20], the antitumor effect enhancer according to [21], the antitumor agent according to [22] or [23], the use according to [24] or [25], or the method according to [26], wherein the tumor is selected from the group consisting of gastric cancer, biliary tract cancer, uterine cancer, bladder cancer, and brain tumor.

[30] The combination preparation according to any of [1] to [19], the pharmaceutical composition according to [20], the antitumor effect enhancer according to [21], the antitumor agent according to [22] or [23], the use according to [24] or [25], or the method according to [26], wherein the tumor is gastric cancer, and the additional compound having an antitumor effect or the pharmaceutically acceptable salt thereof is selected from the group consisting of paclitaxel, docetaxel, tegafur/gimeracil/oteracil potassium, 5-fluorouracil, gemcitabine, capecitabine, oxaliplatin, cisplatin, and ramucirumab.

[31] The combination preparation according to any of [1] to [19], the pharmaceutical composition according to [20], the antitumor effect enhancer according to [21], the antitumor agent according to [22] or [23], the use according to [24] or [25], or the method according to [26], wherein the tumor is biliary tract cancer, and the additional compound having an antitumor effect or the pharmaceutically acceptable salt thereof is selected from the group consisting of gemcitabine and cisplatin.

[32] The combination preparation according to any of [1] to [19], the pharmaceutical composition according to [20], the antitumor effect enhancer according to [21], the antitumor agent according to [22] or [23], the use according to [24] or [25], or the method according to [26], wherein the tumor is bladder cancer, and the additional compound having an antitumor effect or the pharmaceutically acceptable salt thereof is selected from the group consisting of methotrexate, gemcitabine, paclitaxel, docetaxel, vinblastine, cisplatin, carboplatin, doxorubicin, and atezolizumab.

[33] The combination preparation according to any of [1] to [19], the pharmaceutical composition according to [20], the antitumor effect enhancer according to [21], the antitumor agent according to [22] or [23], the use according to [24] or [25], or the method according to [26], wherein the tumor is brain tumor, and the additional compound having an antitumor effect or the pharmaceutically acceptable salt thereof is selected from the group consisting of irinotecan, bevacizumab, and temozolomide.

[34] The combination preparation according to any of [1] to [19], the pharmaceutical composition according to [20], the antitumor effect enhancer according to [21], the antitumor agent according to [22] or [23], the use according to [24] or [25], or the method according to [26], wherein the tumor is endometrial cancer, and the additional compound having an antitumor effect or the pharmaceutically acceptable salt thereof is selected from the group consisting of 5-fluorouracil, gemcitabine, cisplatin, carboplatin, paclitaxel, doxorubicin, and cyclophosphamide.

[35] The combination preparation according to any of [1] to [19], the pharmaceutical composition according to [20], the antitumor effect enhancer according to [21], the antitumor agent according to [22] or [23], the use according to [24] or [25], or the method according to [26], wherein FGFR is mutated in the tumor to be treated.

[36] The combination preparation according to any of [1] to [19], the pharmaceutical composition according to [20], the antitumor effect enhancer according to [21], the antitumor agent according to [22] or [23], the use according to [24] or [25], or the method according to [26], wherein the tumor to be treated has resistance to the additional compound having an antitumor effect.

The present specification encompasses the contents disclosed in Japanese Patent Application No. 2016-042662 on which the priority of the present application is based.

Advantageous Effects of Invention

According to the present invention, cancer treatment that exerts high antitumor effects (particularly, a cytoreductive effect and a tumor growth-delaying effect (life-prolonging effect)), while suppressing the occurrence of side effects of an antitumor agent, can be performed. Therefore, the long-term survival of cancer patients can be brought about.

BRIEF DESCRIPTION OF DRAWINGS

FIG. 4C shows the antitumor effects of Compound 1 and gemcitabine used alone or concomitantly. The effects (T/C (%)) of Compound 1 and gemcitabine used alone or concomitantly at Day 15 are shown.

FIG. 12A shows the state of EGFR in human non-small cell lung cancer lines HCC4006, NCI-H1650 and NCI-H322.

DESCRIPTION OF EMBODIMENTS

Figure 1A:
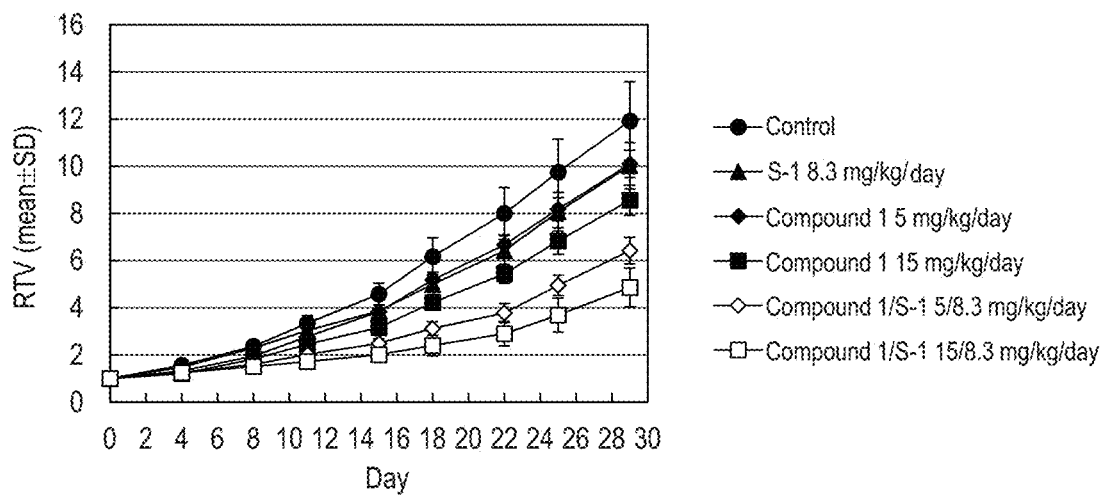
FIG. 1A shows the antitumor effects of Compound 1 and tegafur/gimeracil/oteracil potassium (S-1) used alone or concomitantly. The relative tumor volumes (RTV) in medicine administration groups and a control group are shown.

According to the first embodiment, the present invention provides a combination preparation for the treatment of a malignant tumor comprising a compound represented by Formula (I) or a pharmaceutically acceptable salt thereof, and one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent as active ingredients.

In the present specification, the term "$C_1$-$C_6$ alkyl" refers to a straight or branched alkyl group having 1 to 6 carbon atoms. Specific examples thereof include methyl, ethyl, n-propyl, isopropyl, n-butyl, isobutyl, sec-butyl, tert-butyl, pentyl, hexyl, and the like. The $C_1$-$C_6$ alkyl is preferably a straight or branched alkyl group having 1 to 4 carbon atoms (a $C_1$-$C_4$ alkyl group), and more preferably methyl, ethyl, isopropyl, and tert-butyl.

In this specification, the term "$C_3$-$C_{10}$ cycloalkyl" refers to a monocyclic or polycyclic cycloalkyl group having 3 to 10 carbon atoms, and is preferably a monocyclic cycloalkyl group having 3 to 6 carbon atoms (a $C_3$-$C_6$ cycloalkyl group). Specific examples thereof include cyclopropyl, cyclobutyl, cyclopentyl, cyclohexyl, cycloheptyl, decalyl, and the like. Cyclopropyl and cyclobutyl are preferable.

In this specification, the divalent moiety represented by

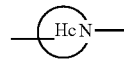

of the group represented by Formula (A)

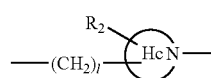

(A)

(wherein $R_2$ and l are as defined above)
is a $C_3$-$C_{10}$ divalent heterocycloalkylene group containing at least one nitrogen atom in the ring and further containing 0 to 2 same or different heteroatoms selected from oxygen and sulfur atoms in the ring (a nitrogen-containing $C_3$-$C_{10}$ heterocycloalkylene group), and is preferably a $C_3$-$C_5$ heterocycloalkylene group containing 1 to 3 nitrogen atoms in the ring and further containing 0 to 1 oxygen atom in the ring (a nitrogen-containing $C_3$-$C_5$ heterocycloalkylene group). Specific examples thereof include azetidinylene, pyrrolidinylene, piperidinylene, piperazinylene, morpholinylene, octahydroquinolinylene, octahydroindolylene, and the like. Among them, azetidinylene, pyrrolidinylene, piperidinylene, piperazinylene, and morpholinylene are preferable.

The group represented by Formula (A)

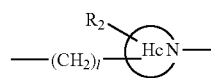

(A)

refers to a divalent nitrogen-containing $C_3$-$C_{10}$ heterocycloalkylene group represented by

wherein the nitrogen atom has one arm and the other arm is connected to a substituent (—$(CH_2)_l$—), and a substituent $R_2$ is present on the ring.

In this specification, the divalent moiety represented by

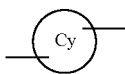

of the group represented by Formula (B)

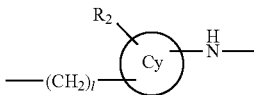
(B)

(wherein $R_2$ and l are as defined above)
refers to a monocyclic or polycyclic divalent cycloalkylene group having 3 to 10 carbon atoms (a $C_3$-$C_{10}$ cycloalkylene group), and preferably a monocyclic divalent cycloalkylene group having 3 to 6 carbon atoms (a $C_3$-$C_6$ cycloalkylene group). Specific examples thereof include cyclopropylene, cyclobutylene, cyclopentylene, cyclohexylene, cycloheptylene, decalylene, and the like. Cyclopropylene and (1,2- or 1,3-)cyclobutylene are preferable.

Formula (B)

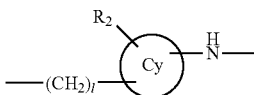
(B)

refers to a divalent $C_3$-$C_{10}$ cycloalkylene group represented by

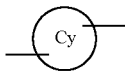

wherein one arm is connected to an adjacent amino group (NH) and the other arm is connected to a substituent (—$(CH_2)_l$—), and a substituent $R_2$ is present on the ring.

In the present specification, the divalent moiety represented by

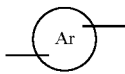

of the group represented by Formula (C)

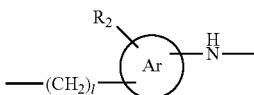
(C)

Formula (C)

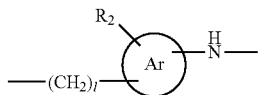
(C)

refers to a divalent $C_6$-$C_{12}$ arylene group represented by

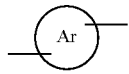

wherein one arm is connected to an adjacent amino group (NH) and the other arm is connected to a substituent (—$(CH_2)_l$—), and a substituent $R_2$ is present on the ring.

In this specification, the monovalent moiety represented by

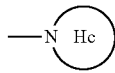

of the group represented by Formula (D)

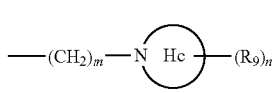
(D)

(wherein $R_9$, m, and n are as defined above)
refers to a $C_3$-$C_{10}$ heterocycloalkyl group containing at least one nitrogen atom in the ring and further containing 0 to 2 same or different heteroatoms selected from oxygen and sulfur atoms in the ring (a nitrogen-containing $C_3$-$C_{10}$ heterocycloalkylene group), and is preferably a $C_3$-$C_5$ heterocycloalkylene group containing 1 to 3 nitrogen atoms in the ring and further containing 0 to 1 oxygen atom in the ring (a nitrogen-containing $C_3$-$C_5$ heterocycloalkylene group). Specific examples thereof include azetidinyl, pyrrolidinyl, piperidinyl, piperazinyl, morpholino, octahydroquinolinyl, octahydroindolinyl, and the like. Azetidinyl, pyrrolidinyl, piperidinyl, piperazinyl, and morpholino groups are preferable.

Formula (D)

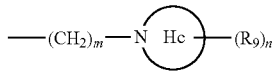
(D)

denotes a nitrogen-containing $C_3$-$C_{10}$ heterocycloalkylene group represented by

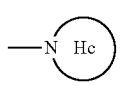

wherein the nitrogen atom is bound to a substituent (—$(CH_2)_m$—), and n substituents (—$(R_9)_n$) are present on the ring.

In this specification, the "$C_2$-$C_9$ heteroaryl" refers to a monocyclic or bicyclic $C_2$-$C_9$ heteroaryl group containing 1 to 3 same or different heteroatoms selected from nitrogen, oxygen, and sulfur atoms; and is preferably a monocyclic $C_2$-$C_5$ heteroaryl group containing 1 to 3 same or different heteroatoms selected from nitrogen, oxygen, and sulfur atoms (a $C_2$-$C_5$ heteroaryl group). Specific examples thereof include thienyl, furyl, pyrrolyl, triazolyl, imidazolyl, pyrazolyl, oxadiazolyl, isothiazolyl, isoxazolyl, pyridyl, pyrazinyl, pyrimidinyl, pyridazinyl, isobenzofuryl, indolizinyl, isoindolyl, indolyl, indazolyl, quinolyl, isoquinolyl, phthalazinyl, naphthyridinyl, and the like. 1,3,4-Oxadiazolyl is preferable.

In this specification, the term "$C_2$-$C_6$ alkynyl" refers to a straight or branched $C_2$-$C_6$ alkynyl group having at least one carbon-carbon triple bond. Specific examples thereof include ethynyl, 2-propynyl, 2-hexynyl, and the like. Ethynyl is preferable.

In the present specification, the term "hydroxy-$C_1$-$C_6$ alkyl" refers to a straight or branched $C_1$-$C_6$ alkyl group having one hydroxy group. Specific examples thereof include hydroxymethyl, hydroxyethyl, hydroxypropyl, hydroxybutyl, hydroxypentyl, hydroxyhexyl, and the like. Among them, hydroxymethyl, 2-hydroxyethyl, 2-hydroxypropyl, and 2-hydroxybutyl are preferable.

In this specification, the term "di($C_1$-$C_6$ alkyl)amino-$C_1$-$C_6$ alkyl group" refers to a straight or branched $C_1$-$C_6$ alkyl group having an amino group having two straight or branched $C_1$-$C_6$ alkyl groups. A straight or branched $C_1$-$C_4$ alkyl group having an amino group having two straight or branched $C_1$-$C_4$ alkyl groups (a di($C_1$-$C_4$ alkyl)amino-$C_1$-$C_4$ alkyl group) is preferable. Specific examples thereof include dimethylaminomethyl, dimethylaminoethyl, dimethylaminopropyl, dimethylaminobutyl, dimethylaminopentyl, dimethylaminohexyl, diethylaminomethyl, diethylaminoethyl, diethylaminopropyl, diethylaminobutyl, diethylaminopentyl, diethylaminohexyl, dipropylaminomethyl, dibutylaminomethyl, dipentylaminomethyl, dihexylaminomethyl, ethyl(methyl)aminomethyl, and the like. Dimethylaminomethyl and diethylaminoethyl are preferable.

In this specification, the term "$C_1$-$C_6$ alkoxy-$C_1$-$C_6$ alkyl" refers to a straight or branched $C_1$-$C_6$ alkyl group having a straight or branched $C_1$-$C_6$ alkoxy group. It is preferably a straight or branched $C_1$-$C_4$ alkyl group having a straight or branched $C_1$-$C_4$ alkoxy group (a $C_1$-$C_4$ alkoxy-$C_1$-$C_4$ alkyl group). Specific examples of such groups include methoxymethyl, methoxyethyl, methoxypropyl, methoxybutyl, methoxypentyl, methoxyhexyl, ethoxymethyl, ethoxyethyl, ethoxypropyl, ethoxybutyl, ethoxypentyl, ethoxyhexyl, propoxymethyl, butoxymethyl, pentyloxymethyl, hexyloxymethyl, and the like. Among them, 2-methoxyethyl is preferable.

In this specification, examples of the "halogen" include chlorine, bromine, fluorine, and iodine. Fluorine is preferable.

In Formula (I), the following combinations of $X_1$ and $X_2$ are preferable. (1) When $X_2$ is N, $X_1$ is N or CH. (2) When $X_2$ is CH, $X_1$ is CH.

In Formula (I), l is preferably 0 or 1.

In Formula (I), Y is preferably a group represented by Formula (A)

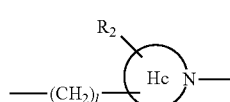
(A)

(wherein $R_2$ and l are as defined above) or a group represented by Formula (C)

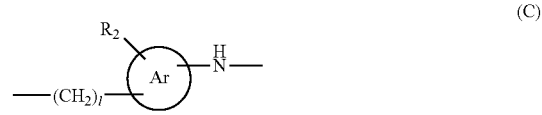
(C)

(wherein $R_2$ and l are as defined above). More preferably, the divalent moiety represented by

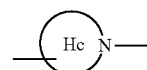

of a group represented by Formula (A) is pyrrolidinylene, azetidinylene, or piperidinylene, or the divalent moiety represented by

of a group represented by Formula (C) is phenylene.

In Formula (I), the following combinations of Y and Z are preferable. When Y is a group represented by Formula (A)

(A)

(wherein $R_2$ and l are as defined above), Z is —C($R_4$)=C($R_5$)($R_6$) or —C≡C—$R_7$. When Y is a group represented by the following Formula (B) or (C):

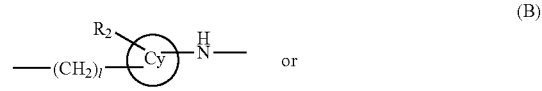
(B)

or

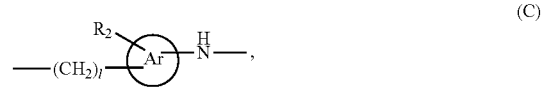
(C)

(wherein $R_2$ and l are as defined above), Z is —C($R_4$)=C($R_5$)($R_6$).

In Formula (I), $R_1$ is preferably $C_1$-$C_4$ alkyl, and more preferably methyl or ethyl.

In Formula (I), $R_2$ is preferably hydrogen, $C_2$-$C_6$ alkynyl, —C(=O)$OR_x$, hydroxy-$C_1$-$C_4$ alkyl, or $C_2$-$C_9$ heteroaryl optionally having $R_3$, and more preferably ethynyl, methoxycarbonyl, hydroxymethyl, or 1,3,4-oxadiazolyl optionally having $R_3$.

In Formula (I), $R_3$ is preferably $C_1$-$C_4$ alkyl or di-($C_1$-$C_4$ alkyl)amino-$C_1$-$C_4$ alkyl, and more preferably methyl or dimethylaminomethyl.

In Formula (I), $R_4$ is preferably hydrogen or halogen, more preferably hydrogen or fluorine, and even more preferably hydrogen.

In Formula (I), $R_5$ and $R_6$ are preferably hydrogen, $C_1$-$C_4$ alkyl group optionally having $R_8$, or a group represented by Formula (D)

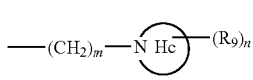

(wherein $R_9$, m, and n are as defined above), and more preferably hydrogen, methyl having $R_8$, or a group represented by Formula (D)

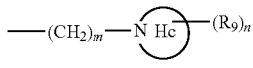

(wherein $R_9$, m, and n are as defined above).

In Formula (I), m is preferably 1.

In Formula (I), $R_9$ is preferably $C_1$-$C_4$ alkyl, fluorine, or hydroxy, and more preferably methyl, fluorine, or hydroxy.

In Formula (I), n is preferably 0 or 1.

In Formula (I), $R_7$ is preferably hydrogen, $C_1$-$C_4$ alkyl, or hydroxy-$C_1$-$C_4$ alkyl, and more preferably hydrogen, hydroxymethyl, methyl, or 2-hydroxy-2-methyl-ethyl.

In Formula (I), $R_8$ is preferably hydroxy or —N($R_x$)($R_y$). In this formula, $R_x$ and $R_y$ are preferably hydrogen, $C_1$-$C_4$ alkyl, $C_3$-$C_{10}$ cycloalkyl, or $C_1$-$C_4$ alkoxy-$C_1$-$C_4$ alkyl, and more preferably hydrogen, methyl, ethyl, tert-butyl, isopropyl, cyclopropyl, cyclobutyl, or 2-methoxyethyl.

Preferable compounds of the present invention are compounds represented by Formula (I) wherein $R_1$ is $C_1$-$C_4$ alkyl; $X_1$ and $X_2$ are independently N or CH; Y is a group represented by the following Formula (A) or (C):

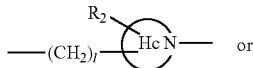

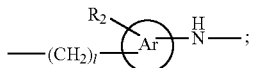

$R_2$ is hydrogen, $C_2$-$C_6$ alkynyl, —C(=O)$OR_x$, hydroxy-$C_1$-$C_4$ alkyl, or $C_2$-$C_9$ heteroaryl optionally having $R_3$; $R_3$ is $C_1$-$C_4$ alkyl or di($C_1$-$C_4$ alkyl)amino-$C_1$-$C_4$ alkyl; Z is —C($R_4$)=C($R_5$)($R_6$) or —C≡C—$R_7$; $R_4$ is hydrogen or halogen; $R_5$ and $R_6$ are the same or different, and each represents hydrogen, $C_1$-$C_4$ alkyl optionally having $R_8$, or a group represented by Formula (D)

$R_7$ is hydrogen, $C_1$-$C_4$ alkyl, or hydroxy-$C_1$-$C_4$ alkyl; $R_8$ is hydroxy or —N($R_x$)($R_y$); $R_9$ is $C_1$-$C_4$ alkyl, fluorine, or hydroxy; $R_x$ and $R_y$ are the same or different, and each represents hydrogen, $C_1$-$C_4$ alkyl, $C_3$-$C_{10}$ cycloalkyl, or $C_1$-$C_4$ alkoxy-$C_1$-$C_4$ alkyl; and l is 0 or 1, m is 1, and n is 0 or 1.

More preferable compounds of the present invention are compounds represented by Formula (I) wherein $R_1$ is $C_1$-$C_4$ alkyl, $X_1$ and $X_2$ are such that (1) when $X_2$ is N, $X_1$ is N or CH, and (2) when $X_2$ is CH, $X_1$ is CH; in Y, the divalent moiety represented by

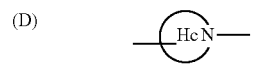

of the group represented by Formula (A)

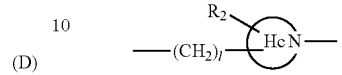

is pyrrolidinylene, azetidinylene, or piperidinylene, or the divalent moiety represented by

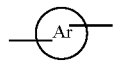

of the group represented by Formula (C)

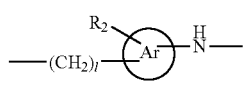

is phenylene;
(a) when Y is a group represented by Formula (A)

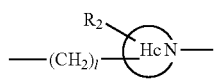

(wherein $R_2$ is hydrogen, ethynyl, methoxycarbonyl, hydroxymethyl, or 1,3,4-oxadiazolyl optionally having $R_3$; $R_3$ is $C_1$-$C_4$ alkyl; and l is 0 or 1), Z is —C($R_4$)=C($R_5$)($R_6$) or —C≡C—$R_7$, (b) when Y is a group represented by Formula (C)

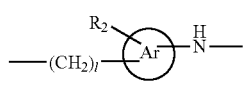

(wherein $R_2$ is hydrogen; and l is 0 or 1), Z is —C($R_4$)=C($R_5$)($R_6$); $R_4$ is hydrogen or fluorine; $R_5$ and $R_6$ are the same or different, and each represents hydrogen, $C_1$-$C_4$ alkyl optionally having $R_8$, or a group represented by Formula (D)

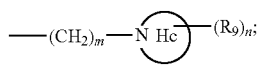

$R_7$ is hydrogen, hydroxymethyl, methyl, or 2-hydroxy-2-methyl-ethyl; $R_8$ is —N($R_x$)($R_y$); $R_9$ is $C_1$-$C_4$ alkyl, fluorine, or hydroxy; $R_x$ and $R_y$ are the same or different, and each represents hydrogen, $C_1$-$C_4$ alkyl, $C_3$-$C_{10}$ cycloalkyl, or $C_1$-$C_4$ alkoxy-$C_1$-$C_4$ alkyl, m is 1, and n is 0 or 1.

Even more preferable compounds of the present invention are compounds represented by Formula (I) wherein $R_1$ is methyl or ethyl; $X_1$ and $X_2$ are such that (1) when $X_2$ is N, $X_1$ is N or CH, and (2) when $X_2$ is CH, $X_1$ is CH; in Y, the divalent moiety represented by

is pyrrolidinylene, azetidinylene, piperidinylene, or the divalent moiety represented by

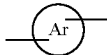

is phenylene;

(a) when Y is a group represented by Formula (A)

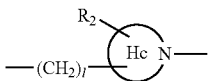

(wherein $R_2$ is hydrogen, ethynyl, methoxycarbonyl, hydroxymethyl, or 1,3,4-oxadiazolyl optionally having methyl; and l is 0 or 1), Z is $-C(R_4)=C(R_5)(R_6)$ or $-C\equiv C-R_7$, (b) when Y is a group represented by Formula (C)

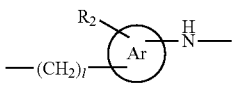

(wherein $R_2$ is hydrogen; and l is 1), Z is $-C(R_4)=C(R_5)(R_6)$; $R_4$ is hydrogen; $R_5$ and $R_6$ are the same or different, and each represents hydrogen, methyl having $R_8$, or the monovalent moiety represented by

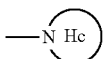

of the group represented by Formula (D)

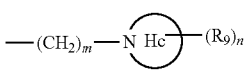

is pyrrolidinyl, piperidinyl, azetidinyl, piperazinyl, or morpholinyl; $R_7$ is hydrogen, hydroxymethyl, methyl, or 2-hydroxy-2-methyl-ethyl; $R_8$ is $-N(R_x)(R_y)$; $R_9$ is methyl, fluorine, or hydroxy and; $R_x$ and $R_y$ are the same or different, and each represents hydrogen, methyl, ethyl, tert-butyl, isopropyl, cyclopropyl, cyclobutyl, or 2-methoxyethyl; and m is 1, and n is 0 or 1.

Specific examples of preferable compounds as a compound of Formula (I) include the following:

(1) (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one, (2) (S)-1-(3-(4-amino-3-((3,5-dimethoxyphenyl)ethynyl)-1H-pyrazolo[3,4-d]pyrimidin-1-yl)pyrrolidin-1-yl)prop-2-yn-1-one, (3) (S)-1-(3-(4-amino-3-((3,5-diethoxyphenyl)ethynyl)-1H-pyrazolo[3,4-d]pyrimidin-1-yl)pyrrolidin-1-yl)prop-2-en-1-one, (4) 1-(3-(4-amino-3-((3,5-dimethoxyphenyl)ethynyl)-1H-pyrazolo[3,4-d]pyrimidin-1-yl)azetidin-1-yl)prop-2-en-1-one, (5) 1-(3-(4-amino-3-((3,5-dimethoxyphenyl)ethynyl)-1H-pyrazolo[3,4-d]pyrimidin-1-yl)azetidin-1-yl)-4-hydroxybut-2-yn-1-one, (6) 1-(3-(4-amino-3-((3,5-dimethoxyphenyl)ethynyl)-1H-pyrazolo[3,4-d]pyrimidin-1-yl)azetidin-1-yl)-4-(dimethylamino)but-2-en-1-one, (7) 1-(3-(4-amino-3-((3,5-dimethoxyphenyl)ethynyl)-1H-pyrazolo[3,4-d]pyrimidin-1-yl)azetidin-1-yl)-4-(cyclopropylamino)but-2-en-1-one, (8) 1-(3-(4-amino-3-((3,5-dimethoxyphenyl)ethynyl)-1H-pyrazolo[3,4-d]pyrimidin-1-yl)azetidin-1-yl)-4-(isopropylamino)but-2-en-1-one, (9) 1-(3-(4-amino-3-((3,5-dimethoxyphenyl)ethynyl)-1H-pyrazolo[3,4-d]pyrimidin-1-yl)azetidin-1-yl)-4-(ethyl(methyl)amino)but-2-en-1-one,

(10) 1-(3-(4-amino-3-((3,5-dimethoxyphenyl)ethynyl)-1H-pyrazolo[3,4-d]pyrimidin-1-yl)azetidin-1-yl)-4-(cyclobutylamino)but-2-en-1-one,

(11) 1-(3-(4-amino-3-((3,5-dimethoxyphenyl)ethynyl)-1H-pyrazolo[3,4-d]pyrimidin-1-yl)azetidin-1-yl)-4-(diethylamino)but-2-en-1-one,

(12) 1-(3-(4-amino-3-((3,5-dimethoxyphenyl)ethynyl)-1H-pyrazolo[3,4-d]pyrimidin-1-yl)azetidin-1-yl)-4-(tert-butylamino)but-2-en-1-one,

(13) 1-(3-(4-amino-3-((3,5-dimethoxyphenyl)ethynyl)-1H-pyrazolo[3,4-d]pyrimidin-1-yl)azetidin-1-yl)-4-(isopropyl(methyl)amino)but-2-en-1-one,

(14) 1-(3-(4-amino-3-((3,5-dimethoxyphenyl)ethynyl)-1H-pyrazolo[3,4-d]pyrimidin-1-yl)azetidin-1-yl)-4-(piperidin-1-yl)but-2-en-1-one (Compound of Example 20),

(15) (S)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one,

(16) (R)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one,

(17) 1-((2S,4S)-4-(4-amino-3-((3,5-dimethoxyphenyl)ethynyl)-1H-pyrazolo[3,4-d]pyrimidin-1-yl)-2-(hydroxymethyl)pyrrolidin-1-yl)prop-2-en-1-one,

(18) 1-(2S,4S)-4-(4-amino-3-((3,5-dimethoxyphenyl)ethynyl)-1H-pyrazolo[3,4-d]pyrimidin-1-yl)-2-ethynylpyrrolidin-1-yl)prop-2-en-1-one,

(19) (S)-1-(3-(4-amino-5-((3,5-dimethoxyphenyl)ethynyl)-7H-pyrrolo[2,3-d]pyrimidin-7-yl)pyrrolidin-1-yl)-4-(dimethylamino)but-2-en-1-one,

(20) (S)-1-(3-(4-amino-5-((3,5-dimethoxyphenyl)ethynyl)-7H-pyrrolo[2,3-d]pyrimidin-7-yl)pyrrolidin-1-yl)prop-2-en-1-one,

(21) (S)-1-(3-(4-amino-5-((3,5-dimethoxyphenyl)ethynyl)-7H-pyrrolo[2,3-d]pyrimidin-7-yl)pyrrolidin-1-yl)-4-(pyrrolidin-1-yl)but-2-en-1-one,

(22) (S)-1-(3-(4-amino-5-((3,5-dimethoxyphenyl)ethynyl)-7H-pyrrolo[2,3-d]pyrimidin-7-yl)pyrrolidin-1-yl)-4-(4-hydroxypiperidin-1-yl)but-2-en-1-one,

(23) (S)-1-(3-(4-amino-5-((3,5-dimethoxyphenyl)ethynyl)-7H-pyrrolo[2,3-d]pyrimidin-7-yl)pyrrolidin-1-yl)but-2-yn-1-one,

(24) (S)-1-(3-(4-amino-5-((3,5-dimethoxyphenyl)ethynyl)-7H-pyrrolo[2,3-d]pyrimidin-7-yl)pyrrolidin-1-yl)-4-hydroxy-4-methylpent-2-yn-1-one,

(25) 1-((S)-3-(4-amino-5-((3,5-dimethoxyphenyl)ethynyl)-7H-pyrrolo[2,3-d]pyrimidin-7-yl)pyrrolidin-1-yl)-4-((S)-3-fluoropyrrolidin-1-yl)but-2-en-1-one,

(26) (S)-1-(3-(4-amino-5-((3,5-dimethoxyphenyflethynyl)-7H-pyrrolo[2,3-d]pyrimidin-7-yl)pyrrolidin-1-yl)-4-(piperidin-1-yl)but-2-en-1-one,

(27) 1-(3-(4-amino-5-((3,5-dimethoxyphenyl)ethynyl)-7H-pyrrolo[2,3-d]pyrimidin-7-yl)azetidin-1-yl)prop-2-en-1-one,

(28) 1-(3-(4-amino-5-((3,5-dimethoxyphenyl)ethynyl)-7H-pyrrolo[2,3-d]pyrimidin-7-yl)azetidin-1-yl)-4-(dimethylamino)but-2-en-1-one,

(29) 1-(3-(4-amino-5-((3,5-dimethoxyphenyl)ethynyl)-7H-pyrrolo[2,3-d]pyrimidin-7-yl)azetidin-1-yl)-4-(pyrrolidin-1-yl)but-2-en-1-one,

(30) 1-(3-(4-amino-5-((3,5-dimethoxyphenyl)ethynyl)-7H-pyrrolo[2,3-d]pyrimidin-7-yl)azetidin-1-yl)-4-(azetidin-1-yl)but-2-en-1-one,

(31) 1-(3-(4-amino-5-((3,5-dimethoxyphenyl)ethynyl)-7H-pyrrolo[2,3-d]pyrimidin-7-yl)azetidin-1-yl)-4-(ethyl(methyl)amino)but-2-en-1-one,

(32) 1-(3-(4-amino-5-((3,5-dimethoxyphenyl)ethynyl)-7H-pyrrolo[2,3-d]pyrimidin-7-yl)azetidin-1-yl)-4-(isopropylamino)but-2-en-1-one,

(33) 1-(3-(4-amino-5-((3,5-dimethoxyphenyl)ethynyl)-7H-pyrrolo[2,3-d]pyrimidin-7-yl)azetidin-1-yl)-4-(diethylamino)but-2-en-1-one,

(34) 1-(3-(4-amino-5-((3,5-dimethoxyphenyl)ethynyl)-7H-pyrrolo[2,3-d]pyrimidin-7-yl)azetidin-1-yl)-4-((2-methoxyethyl)(methyl)amino)but-2-en-1-one,

(35) 1-(3-(4-amino-5-((3,5-dimethoxyphenyl)ethynyl)-7H-pyrrolo[2,3-d]pyrimidin-7-yl)azetidin-1-yl)-4-(4-hydroxypiperidin-1-yl)but-2-en-1-one,

(36) (S)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one,

(37) (R)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one,

(38) (2S,4S)-methyl 1-acryloyl-4-(4-amino-5-((3,5-dimethoxyphenyl)ethynyl)-7H-pyrrolo[2,3-d]pyrimidin-7-yl)pyrrolidine-2-carboxylate,

(39) 1-((2S,4S)-4-(4-amino-5-((3,5-dimethoxyphenyl)ethynyl)-7H-pyrrolo[2,3-d]pyrimidin-7-yl)-2-(1,3,4-oxadiazol-2-yl)pyrrolidin-1-yl)prop-2-en-1-one, and

(40) (S)-1-(3-(4-amino-3-((3,5-dimethoxyphenyl)ethynyl)-1H-pyrrolo[3,2-c]pyridin-1-yl)pyrrolidin-1-yl)prop-2-en-1-one.

Among them, (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one is preferable.

The compound represented by Formula (I) or a pharmaceutically acceptable salt thereof in the above-described combination preparation of the present invention can be synthesized on the basis of a production method described in, for example, WO 2013/108809 (PTL 1), though the production method is not particularly limited thereto.

(S)-1-(3-(4-Amino-3-((3,5-dimethoxyphenyl)ethynyl)-1H-pyrazolo[3,4-d]pyrimidin-1-yl)pyrrolidin-1-yl)prop-2-en-1-one, which is one example of the compound represented by Formula (I), is a disubstituted benzene alkynyl compound having a structure described below. In the present specification, the compound is referred to as "Compound 1" for the sake of convenience. Compound 1 is described as Example Compound 2 in WO 2013/108809.

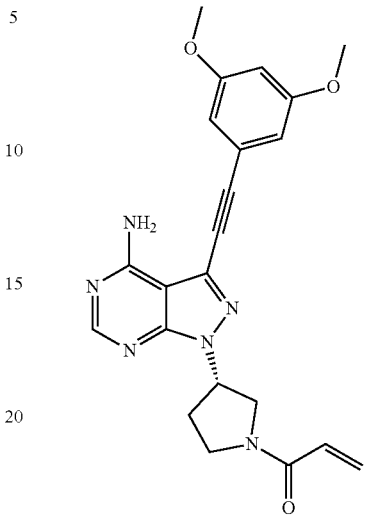

In the present invention, the compound represented by Formula (I) can be used directly or in the form of a pharmaceutically acceptable salt. The pharmaceutically acceptable salt of the compound represented by Formula (I) is not particularly limited, and examples thereof include addition salts with inorganic acids such as hydrochloric acid and sulfuric acid, organic acids such as acetic acid, citric acid, tartaric acid, and maleic acid; salts with alkali metals such as potassium and sodium; salts with alkaline earth metals such as calcium and magnesium; and salts with organic bases, such as ammonium salts, ethylamine salts, and alginate.

The compound represented by Formula (I) is an antitumor agent that has an excellent FGFR inhibitory effect and has reduced side effects, and, when concomitantly used with various additional compounds having an antitumor effect, has an effect of enhancing the antitumor effects of the additional compounds having an antitumor effect without remarkably exacerbating toxicity.

Accordingly, the combination preparation of the present invention comprises one or more additional compound(s) having an antitumor effect or pharmaceutically acceptable salt(s) thereof, which is different from the compound represented by Formula (I). Examples of the number of additional compounds having an antitumor effect or pharmaceutically acceptable salts thereof include one or more, preferably one. The additional compound having an antitumor effect or pharmaceutically acceptable salt thereof is selected from an antimetabolite (a purine antimetabolite, a pyrimidine antimetabolite, an antifolate, etc.), an alkaloid antitumor agent, a platinum-containing drug, a molecular targeting drug (a low-molecular-weight molecular targeting drug, an antibody molecular targeting drug, etc.), an antitumor antibiotic, and an alkylating agent.

In this context, the "additional compound having an antitumor effect or pharmaceutically acceptable salt thereof" is intended to exclude the compound represented by Formula (I), because the compound represented by Formula (I) is an antitumor agent based on an FGFR inhibitory effect. The additional compound having an antitumor effect is not particularly limited, and examples thereof include antimetabolites (purine antimetabolites, antifolates, and pyrimidine antimetabolites), alkaloid antitumor agents, platinum-containing drugs, molecular targeting drugs (low-molecular-weight molecular targeting drugs, antibody molecular targeting drugs, and immune checkpoint inhibitors), antitumor antibiotics, alkylating agents, and more specifically include purine antimetabolites such as fludarabine, cladribine, and nelarabine;

pyrimidine antimetabolites such as 5-fluorouracil (5-FU), tegafur/gimeracil/oteracil potassium (TS-1 or S-1, trade name: "TS-1"), tegafur/uracil (UFT, trade name: "UFT"), trifluridine/tipiracil hydrochloride (TAS-102, trade name: "LONSURF"), capecitabine, doxifluridine, 5-fluoro-2'-deoxyuridine (FdUrd), gemcitabine, and cytarabine;

antifolates such as pemetrexed and methotrexate;

alkaloid antitumor agents such as paclitaxel (sold under trade names of "Taxol", "Abraxane", etc.; paclitaxel includes derivatives such as albumin-bound paclitaxel (e.g., ABI-007) and PEG-bound paclitaxel), docetaxel (trade name "Taxotere", etc.), cabazitaxel, eribulin, irinotecan, nogitecan, etoposide, vinorelbine, vincristine, and vinblastine;

platinum-containing drugs such as cisplatin, carboplatin, oxaliplatin, and nedaplatin;

low-molecular-weight molecular targeting drugs such as imatinib, gefitinib, erlotinib, lapatinib, sunitinib, dasatinib, everolimus, temsirolimus, selumetinib, trametinib, sorafenib, afatinib, regorafenib, dabrafenib, vemurafenib, trans-3-amino-1-methyl-3-(4-(3-phenyl-5H-imidazo[1,2-c]pyrido[3,4-e][1,3]oxazin-2-yl)phenyl)cyclobutanol (in the present specification, referred to as "Compound 2") and pharmaceutically acceptable salts thereof, and 8-[4-(1-aminocyclobutyl)phenyl]-9-phenyl-1,2,4-triazolo[3,4-f][1,6]naphthyridin-3(2H)-one (MK2206) and pharmaceutically acceptable salts thereof;

antibody molecular targeting drugs such as trastuzumab, cetuximab, bevacizumab, panitumumab, veltuzumab, rituximab, and ramucirumab;

immune checkpoint inhibitors such as nivolumab, pembrolizumab, atezolizumab, durvalumab, avelumab, ipilimumab, tremelimumab, and abatacept;

antitumor antibiotics such as doxorubicin, daunorubicin, epirubicin, actinomycin D, and mitomycin C; and alkylating agents such as cyclophosphamide, dacarbazine, temozolomide, nimustine, busulfan, procarbazine, and melphalan.

The above-described low-molecular-weight molecular targeting drugs include those based on various mechanisms of action. For example, gefitinib is known to exert an antitumor effect through an EGFR inhibitory effect and is called an EGFR inhibitor. It is also known that MAPK, PI3K/AKT/mTOR, and NF-κB signaling pathways are aberrantly activated in various cancer cells. Inhibitors of these signaling pathways can also be used as antitumor agents in the present invention.

Examples of AKT inhibitors known to exert an antitumor effect through an AKT inhibitory effect may include trans-3-amino-1-methyl-3-(4-(3-phenyl-5H-imidazo[1,2-c]pyrido[3,4-e][1,3]oxazin-2-yl)phenyl)cyclobutanol (Compound 2) and pharmaceutically acceptable salts thereof, and 8-[4-(1-aminocyclobutyl)phenyl]-9-phenyl-1,2,4-triazolo[3,4-f][1,6]naphthyridin-3(2H)-one (MK2206) and pharmaceutically acceptable salts thereof.

The above-described Compound 2 is a compound described in Example 32 of WO 2012/137870 and can be synthesized on the basis of a production method described therein.

Examples of mTOR inhibitors known to exert an antitumor effect through a mTOR inhibitory effect may include everolimus.

Examples of the pyrimidine antimetabolite include the above-described compounds. The pyrimidine antimetabolite is preferably 5-fluorouracil(5-FU), tegafur/gimeracil/oteracil potassium, or gemcitabine, more preferably tegafur/gimeracil/oteracil potassium or gemcitabine, and particularly preferably tegafur/gimeracil/oteracil potassium.

Examples of the alkaloid antitumor agent include the above-described compounds. The alkaloid antitumor agent is preferably paclitaxel.

Examples of the platinum-containing drug include the above-described compounds. The platinum-containing drug is preferably cisplatin.

Examples of the low-molecular-weight molecular targeting drug include the above-described compounds. The low-molecular-weight molecular targeting drug is preferably an AKT inhibitor, an mTOR inhibitor, or an EGFR inhibitor, and more preferably an AKT inhibitor or an mTOR inhibitor.

Examples of the additional compound having an antitumor effect include the above-described compounds. The additional compound having an antitumor effect is preferably a pyrimidine antimetabolite, an alkaloid antitumor agent, a platinum-containing drug, or a low-molecular-weight molecular targeting drug. More preferably, the additional compound having an antitumor effect is a pyrimidine antimetabolite, a vegetable alkaloid antitumor agent, a platinum-containing drug, an AKT inhibitor, or an mTOR inhibitor. Even more preferably, the additional compound having an antitumor effect is tegafur/gimeracil/oteracil potassium, gemcitabine, paclitaxel, cisplatin, everolimus, or trans-3-amino-1-methyl-3-(4-(3-phenyl-5H-imidazo[1,2-c]pyrido[3,4-e][1,3]oxazin-2-yl)phenyl)cyclobutanol (Compound 2) or a pharmaceutically acceptable salt thereof, 8-[4-(1-aminocyclobutyl)phenyl]-9-phenyl-1,2,4-triazolo[3,4-f][1,6]naphthyridin-3(2H)-one (MK2206) or a pharmaceutically acceptable salt thereof, or everolimus, and particularly preferably tegafur/gimeracil/oteracil potassium or paclitaxel. Alternatively, the additional compound having an antitumor effect may be provided as a derivative or as a complex without reducing its pharmacological effect or in order to enhance its pharmacological effect, for example, in order to improve pharmacokinetics in vivo, improve delivery to a target site, or suppress decomposition.

The respective action mechanisms, doses and therapeutic targets of the above-described antitumor agents are known, and persons skilled in the art can obtain these antitumor agents together with necessary information.

As known to persons skilled in the art, even medicines excellent in antitumor effect may inflict additional suffering to patients due to their side effects. The combination preparation of the present invention can reduce the dose and dosing frequency of a medicine by the enhancement of the antitumor effect and can consequently be effective for the suppression of side effects.

The malignant tumor that can be treated with the combination preparation of the present invention is not particularly limited, and examples thereof include epithelial cancer (respiratory cancer, gastrointestinal cancer, genital cancer, cancer of the secretory system, breast cancer, etc.), sarcoma, hematopoietic tumor, tumor of the central nervous system, and tumor of the peripheral nervous system.

Specific examples of the respiratory cancer include lung cancer (non-small cell lung cancer, small-cell lung cancer, etc.). Specific examples of the gastrointestinal cancer include esophagus cancer, gastric cancer, duodenum cancer, liver cancer, hepatocellular cancer, biliary tract cancer (gallbladder cancer, cholangiocarcinoma, intrahepatic cholangiocarcinoma, extrahepatic cholangiocarcinoma, etc.), pancreatic cancer, and colorectal cancer (colon cancer, rectum cancer, etc.). Specific examples of the genital cancer include ovarian cancer, uterine cancer (cervical cancer, endometrial cancer, etc.), renal cancer, bladder cancer, prostate cancer, and testicular tumor. Specific examples of the cancer of the secretory system include thyroid cancer. Specific examples of the sarcoma include bone or soft tissue tumor. Specific examples of the hematopoietic tumor include leukemia, malignant lymphoma, and multiple myeloma. Specific examples of the tumor of the central nervous system include head and neck cancer and brain tumor. Specific examples of the tumor of the peripheral nervous system include skin cancer.

The malignant tumor to be treated in the present invention is even more preferably lung cancer, esophagus cancer, gastric cancer, biliary tract cancer (gallbladder cancer, cholangiocarcinoma, intrahepatic cholangiocarcinoma, or extrahepatic cholangiocarcinoma), endometrial cancer, bladder cancer, breast cancer, osteosarcoma, soft tissue sarcoma, multiple myeloma, or brain tumor, and particularly preferably gastric cancer, biliary tract cancer (gallbladder cancer, cholangiocarcinoma, intrahepatic cholangiocarcinoma, or extrahepatic cholangiocarcinoma), endometrial cancer, bladder cancer, or brain tumor.

Examples of the additional compound having an antitumor effect or the pharmaceutically acceptable salt thereof that can be preferably used in the combination preparation of the present invention for gastric cancer to be treated in the present invention include pyrimidine antimetabolites, alkaloid antitumor agents, platinum-containing drugs, and antitumor antibiotics. Such an additional compound having an antitumor effect or a pharmaceutically acceptable salt thereof is preferably selected from the group consisting of paclitaxel, docetaxel, tegafur/gimeracil/oteracil potassium, 5-fluorouracil, gemcitabine, capecitabine, oxaliplatin, cisplatin, and ramucirumab, and is more preferably tegafur/gimeracil/oteracil potassium or paclitaxel.

Examples of the additional compound having an antitumor effect or the pharmaceutically acceptable salt thereof that can be preferably used in the combination preparation of the present invention for biliary tract cancer to be treated in the present invention include pyrimidine antimetabolites and platinum-containing drugs, preferably gemcitabine and cisplatin.

Examples of the additional compound having an antitumor effect or the pharmaceutically acceptable salt thereof that can be preferably used in the combination preparation of the present invention for bladder cancer to be treated in the present invention include pyrimidine antimetabolites, antifolates, alkaloid antitumor agents, platinum-containing drugs, antitumor antibiotics, and immune checkpoint inhibitors. Such an additional compound having an antitumor effect or a pharmaceutically acceptable salt thereof is preferably selected from the group consisting of methotrexate, gemcitabine, paclitaxel, docetaxel, vinblastine, cisplatin, carboplatin, doxorubicin, and atezolizumab.

Examples of the additional compound having an antitumor effect or the pharmaceutically acceptable salt thereof that can be preferably used in the combination preparation of the present invention for brain tumor to be treated in the present invention include antibody molecular targeting drugs, alkaloid antitumor agents, and alkylating agents. Such an additional compound having an antitumor effect or a pharmaceutically acceptable salt thereof is preferably selected from the group consisting of irinotecan, bevacizumab, and temozolomide.

Examples of the additional compound having an antitumor effect or the pharmaceutically acceptable salt thereof that can be preferably used in the combination preparation of the present invention for endometrial cancer to be treated in the present invention include pyrimidine antimetabolites, platinum-containing drugs, alkaloid antitumor agents, antitumor antibiotics, and alkylating agents. Such an additional compound having an antitumor effect or a pharmaceutically acceptable salt thereof is preferably selected from the group consisting of 5-fluorouracil, gemcitabine, cisplatin, carboplatin, paclitaxel, doxorubicin, and cyclophosphamide.

In the combination preparation of the present invention, the compound represented by Formula (I) or the pharmaceutically acceptable salt thereof, and one or more additional compound(s) having an antitumor effect or pharmaceutically acceptable salt(s) thereof, selected from a pyrimidine antimetabolite, an alkaloid antitumor agent, a platinum-containing drug, and a molecular targeting drug may be separately formulated in a plurality of preparations or may be collectively formulated in a single preparation. Also, the combination preparation of the present invention may further contain an active ingredient other than the compound represented by Formula (I) or the pharmaceutically acceptable salt and the additional compound having an antitumor effect or the pharmaceutically acceptable salt thereof, and is preferably a combination preparation containing only the compound represented by Formula (I) or the pharmaceutically acceptable salt thereof, and the additional compound having an antitumor effect or the pharmaceutically acceptable salt thereof as active ingredients.

When the compound represented by Formula (I) or the pharmaceutically acceptable salt thereof, and the additional compound having an antitumor effect or the pharmaceutically acceptable salt thereof are contained as active ingredients in preparations, a pharmaceutical carrier can be added to each active ingredient, if required, thereby forming various suitable dosage forms according to prevention and treatment purposes. Examples of the dosage form include oral preparations, injections, suppositories, ointments, and patches. Oral preparations are preferable. The oral preparations can be forms such as tablets, capsules, granules, powders, and syrups and are not particularly limited. Such dosage forms can be manufactured by methods conventionally known to persons skilled in the art. Preparations or pharmaceutical compositions can be supplemented with a suitable carrier such as an excipient, diluent, bulking agent, or disintegrant according to dosage forms or if necessary.

The daily dose of the compound represented by Formula (I) or the pharmaceutically acceptable salt thereof may vary depending on the condition, body weight, age, and sex of a patient, etc., and cannot be generalized. Usually, the daily dose is approximately 1 to 1000 mg, preferably approximately 10 to 500 mg, and more preferably approximately 20 to 300 mg of the compound represented by Formula (I) or the pharmaceutically acceptable salt thereof, per adult (body weight: 60 kg).

In the case of administering each day the daily dose of the compound represented by Formula (I) or the pharmaceutically acceptable salt thereof, the compound represented by Formula (I) or the pharmaceutically acceptable salt thereof is administered at approximately 1 to 200 mg per day, preferably 2 to 100 mg per day, more preferably 4 to 50 mg per day, and even more preferably 10 to 40 mg per day.

In the case of administering every other day the daily dose of the compound represented by Formula (I) or the pharmaceutically acceptable salt thereof, the compound represented by Formula (I) or the pharmaceutically acceptable salt thereof is administered at approximately 2 to 1000 mg per day, preferably 10 to 500 mg per day, more preferably 20 to 200 mg per day, and even more preferably 50 to 160 mg per day.

When the compound represented by Formula (I) or the pharmaceutically acceptable salt thereof, and the additional compound having an antitumor effect or the pharmaceutically acceptable salt thereof are separately formulated as two or more different preparations, the preparation containing the compound represented by Formula (I) or the pharmaceutically acceptable salt thereof and the preparation containing the additional compound having an antitumor effect or the pharmaceutically acceptable salt thereof can be administered simultaneously, separately, or sequentially. The dosing interval for the separate administration is not particularly limited and can be selected so as to optimally exert the respective effects of the compound represented by Formula (I) or the pharmaceutically acceptable salt thereof, and the additional compound having an antitumor effect or the pharmaceutically acceptable salt thereof, and the effect of concomitant use. For the sequential administration, the preparation containing the compound represented by Formula (I) or the pharmaceutically acceptable salt thereof and the preparation containing the additional compound having an antitumor effect or the pharmaceutically acceptable salt thereof can be administered in any order.

In the combination preparation of the present invention, the preparation containing the compound represented by Formula (I) or the pharmaceutically acceptable salt thereof and the preparation containing the additional compound having an antitumor effect or the pharmaceutically acceptable salt thereof may be administered through the same route or different routes. For example, both of the preparation containing the compound represented by Formula (I) or the pharmaceutically acceptable salt thereof and the preparation containing the additional compound having an antitumor effect or the pharmaceutically acceptable salt thereof can be orally administered. Alternatively, for example, the preparation containing the compound represented by Formula (I) or the pharmaceutically acceptable salt thereof can be orally administered while the preparation containing the additional compound having an antitumor effect or the pharmaceutically acceptable salt thereof can be administered by intravenous injection. The administration route can be appropriately determined according to the active ingredients to be administered and in consideration of the degree of progression of the malignant tumor in a patient, the general condition of the patient, etc.

The combination preparation of the present invention can be administered to a patient before or after operation and can also be administered to an inoperable patient. The combination preparation of the present invention can further contain a medicine for enhancing an antitumor effect and can also contain a medicine for reducing side effects.

In one aspect of the present invention, for the treatment of gastric cancer, for example, the compound represented by Formula (I) or the pharmaceutically acceptable salt thereof and a pyrimidine antimetabolite tegafur/gimeracil/oteracil potassium can be concomitantly used, and both the medicines can be orally administered as active ingredients in the combination preparation or as active ingredients in a pharmaceutical composition described below.

In another aspect of the present invention, for the treatment of gastric cancer, for example, the compound represented by Formula (I) or the pharmaceutically acceptable salt thereof and an alkaloid antitumor agent paclitaxel can be concomitantly used, and the compound represented by Formula (I) or the pharmaceutically acceptable salt thereof can be orally administered while paclitaxel can be intravenously administered.

In one aspect of the present invention, for the treatment of biliary tract cancer, for example, the compound represented by Formula (I) or the pharmaceutically acceptable salt thereof and an alkaloid antitumor agent gemcitabine can be concomitantly used, and the compound represented by Formula (I) or the pharmaceutically acceptable salt thereof can be orally administered while gemcitabine can be intravenously administered.

In another aspect of the present invention, for the treatment of biliary tract cancer, for example, the compound represented by Formula (I) or the pharmaceutically acceptable salt thereof and a platinum-containing drug cisplatin can be concomitantly used, and the compound represented by Formula (I) or the pharmaceutically acceptable salt thereof can be orally administered while cisplatin can be intravenously administered.

In one aspect of the present invention, for the treatment of bladder cancer, for example, the compound represented by Formula (I) or the pharmaceutically acceptable salt thereof and a platinum-containing drug cisplatin can be concomitantly used, and the compound represented by Formula (I) or the pharmaceutically acceptable salt thereof can be orally administered while cisplatin can be intravenously administered.

In one aspect of the present invention, for the treatment of brain tumor, for example, the compound represented by Formula (I) or the pharmaceutically acceptable salt thereof and an alkylating agent temozolomide can be concomitantly used, and the compound represented by Formula (I) or the pharmaceutically acceptable salt thereof can be orally administered while temozolomide can be intravenously or orally administered.

In one aspect of the present invention, for the treatment of endometrial cancer, for example, the compound represented by Formula (I) or the pharmaceutically acceptable salt thereof and a platinum-containing drug cisplatin, a pyrimidine antimetabolite gemcitabine, or a molecular targeting drug everolimus can be concomitantly used, and the administration route and dosing frequency of each medicine can be appropriately determined.

The administration or mixing ratios of the compound represented by Formula (I) or the pharmaceutically acceptable salt thereof and the additional compound having an antitumor effect or the pharmaceutically acceptable salt thereof are not particularly limited insofar as the ratios fall within a range that exerts an enhancing effect on an antitumor effect. The compound represented by Formula (I) or the pharmaceutically acceptable salt thereof can be used at approximately 0.001 to 1000 moles, preferably approximately 0.01 to 100 moles, in terms of a free form per mole of the additional compound having an antitumor effect.

When the additional compound having an antitumor effect is a pyrimidine antimetabolite, for example, the compound represented by Formula (I) or the pharmaceutically acceptable salt thereof can be used in an amount ranging from preferably 0.001 to 10 moles, and more preferably from 0.01 to 1 moles, per mole of the pyrimidine antimetabolite.

When the additional compound having an antitumor effect is an alkaloid antitumor agent, the compound represented by Formula (I) or the pharmaceutically acceptable salt thereof can be used in an amount ranging from preferably 0.01 to 200 moles, and more preferably from 0.1 to 100 moles, per mole of the alkaloid antitumor agent.

When the additional compound having an antitumor effect is a platinum-containing drug, the compound represented by Formula (I) or the pharmaceutically acceptable salt thereof can be used in an amount ranging from preferably 0.001 to 50 moles, and more preferably from 0.01 to 10 moles, per mole of the platinum-containing drug.

When the additional compound having an antitumor effect is a low-molecular-weight molecular targeting drug, the compound represented by Formula (I) or the pharmaceutically acceptable salt thereof can be used in an amount ranging from preferably 1 to 1000 moles, and more preferably from 10 to 100 moles, per mole of the low-molecular-weight molecular targeting drug.

When the additional compound having an antitumor effect is an mTOR inhibitor, for example, the compound represented by Formula (I) or the pharmaceutically acceptable salt thereof can be used in an amount ranging from preferably 1 to 1000 moles, and more preferably from 10 to 100 moles, per mole of the mTOR inhibitor.

When the additional compound having an antitumor effect is an antibody molecular targeting drug, the compound represented by Formula (I) or the pharmaceutically acceptable salt thereof can be used in an amount ranging from preferably 0.005 to 1 mg, and more preferably from 0.01 to 0.5 mg, per mg of the antibody molecular targeting drug.

When the additional compound having an antitumor effect is tegafur/gimeracil/oteracil potassium (pyrimidine antimetabolite), for example, the compound represented by Formula (I) or the pharmaceutically acceptable salt thereof can be used at 0.01 to 10 moles, preferably 0.1 to 2 moles, per mole of tegafur. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.01 to 1 moles and more preferably 0.05 to 0.5 moles, per mole of tegafur. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.01 to 10 moles and more preferably from 0.1 to 3 moles, per mole of tegafur.

When the additional compound having an antitumor effect is 5-fluorouracil (pyrimidine antimetabolite), the compound represented by Formula (I) or the pharmaceutically acceptable salt thereof can be used at 0.0001 to 1 moles, preferably 0.0005 to 0.5 moles, per mole of 5-fluorouracil. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.0001 to 0.1 moles and more preferably 0.005 to 0.05 moles, per mole of 5-fluorouracil. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.0001 to 1 moles and more preferably from 0.001 to 0.5 moles, per mole of 5-fluorouracil.

When the additional compound having an antitumor effect is capecitabine (pyrimidine antimetabolite), the compound represented by Formula (I) or the pharmaceutically acceptable salt thereof can be used at 0.001 to 1 moles, preferably 0.005 to 0.1 moles, per mole of capecitabine. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.001 to 0.1 moles and more preferably 0.005 to 0.05 moles, per mole of capecitabine. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.005 to 0.5 moles and more preferably from 0.01 to 0.1 moles, per mole of capecitabine.

When the additional compound having an antitumor effect is gemcitabine (pyrimidine antimetabolite), the compound represented by Formula (I) or the pharmaceutically acceptable salt thereof can be used at 0.001 to 1 moles, preferably 0.005 to 0.1 moles, per mole of gemcitabine. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.001 to 0.1 moles and more preferably from 0.005 to 0.05 moles, per mole of gemcitabine. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.005 to 1 moles and more preferably from 0.01 to 0.1 moles, per mole of gemcitabine.

When the additional compound having an antitumor effect is paclitaxel (alkaloid antitumor agent), the compound represented by Formula (I) or the pharmaceutically acceptable salt thereof can be used at 0.01 to 10 moles, preferably 0.05 to 5 moles, per mole of paclitaxel. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.01 to 1 moles and more preferably from 0.05 to 0.5 moles, per mole of paclitaxel. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.1 to 10 moles and more preferably from 0.2 to 5 moles, per mole of paclitaxel.

When the additional compound having an antitumor effect is docetaxel (alkaloid antitumor agent), the compound represented by Formula (I) or the pharmaceutically acceptable salt thereof can be used at 0.05 to 10 moles, preferably 0.1 to 5 moles, per mole of docetaxel. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.05 to 1 moles and more preferably from 0.1 to 0.5 moles, per mole of docetaxel. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.1 to 10 moles and more preferably from 0.5 to 5 moles, per mole of docetaxel.

When the additional compound having an antitumor effect is irinotecan (alkaloid antitumor agent), the compound represented by Formula (I) or the pharmaceutically acceptable salt thereof can be used at 0.01 to 2 moles, preferably 0.02 to 1 moles, per mole of irinotecan. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.01 to 1 moles and more preferably from 0.02 to 0.1 moles, per mole of irinotecan. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.05 to 2 moles and more preferably from 0.1 to 1 moles, per mole of irinotecan.

When the additional compound having an antitumor effect is vinblastine (alkaloid antitumor agent), the compound represented by Formula (I) or the pharmaceutically acceptable salt thereof can be used at 1 to 200 moles, preferably 5 to 100 moles, per mole of vinblastine. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 1 to 30 moles and more preferably from 5 to 20 moles, per mole of vinblastine. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 5 to 200 moles and more preferably from 10 to 100 moles, per mole of vinblastine.

When the additional compound having an antitumor effect is cisplatin (platinum-containing drug), the compound represented by Formula (I) or the pharmaceutically acceptable salt thereof can be used at 0.01 to 50 moles, preferably 0.05 to 10 moles, per mole of cisplatin. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.01 to 10 moles and more preferably from 0.05 to 2 moles, per mole of cisplatin. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.1 to 10 moles and more preferably from 0.2 to 6 moles, per mole of cisplatin.

When the additional compound having an antitumor effect is oxaliplatin (platinum-containing drug), the compound represented by Formula (I) or the pharmaceutically acceptable salt thereof can be used at 0.01 to 5 moles, preferably 0.05 to 2 moles, per mole of oxaliplatin. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.01 to 1 moles and more preferably from 0.05 to 0.5 moles, per mole of oxaliplatin. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.05 to 5 moles and more preferably from 0.1 to 2 moles, per mole of oxaliplatin.

When the additional compound having an antitumor effect is carboplatin (platinum-containing drug), the compound represented by Formula (I) or the pharmaceutically acceptable salt thereof can be used at 0.001 to 1 moles, preferably 0.01 to 0.5 moles, per mole of carboplatin. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.001 to 0.1 moles and more preferably from 0.01 to 0.1 moles, per mole of carboplatin. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.01 to 1 moles and more preferably from 0.05 to 0.5 moles, per mole of carboplatin.

When the additional compound having an antitumor effect is everolimus (low-molecular-weight molecular targeting drug), the compound represented by Formula (I) or the pharmaceutically acceptable salt thereof can be used at 1 to 1000 moles, preferably 10 to 100 moles, per mole of everolimus.

When the additional compound having an antitumor effect is ramucirumab (antibody molecular targeting drug), the compound represented by Formula (I) or the pharmaceutically acceptable salt thereof can be used at 0.01 to 1 mg, preferably 0.02 to 0.5 mg, per mg of ramucirumab. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.01 to 0.2 mg and more preferably from 0.02 to 0.1 mg, per mg of ramucirumab. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.02 to 1 mg and more preferably from 0.05 to 0.5 mg, per mole of ramucirumab.

When the additional compound having an antitumor effect is bevacizumab (antibody molecular targeting drug), the compound represented by Formula (I) or the pharmaceutically acceptable salt thereof can be used at 0.005 to 1 mg, preferably 0.01 to 0.5 mg, per mg of bevacizumab. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.005 to 0.1 mg and more preferably from 0.01 to 0.1 mg, per mg of bevacizumab. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.01 to 1 mg and more preferably 0.05 to 0.5 mg, per mg of bevacizumab.

When the additional compound having an antitumor effect is atezolizumab (immune checkpoint inhibitor), the compound represented by Formula (I) or the pharmaceutically acceptable salt thereof can be used at 0.001 to 1 mg, preferably 0.01 to 0.5 mg, per mg of atezolizumab. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.001 to 0.1 mg and more preferably from 0.01 to 0.05 mg, per mg of atezolizumab. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.01 to 1 mg and more preferably from 0.03 to 0.5 mg, per mg of atezolizumab.

When the additional compound having an antitumor effect is methotrexate (antifolate), the compound represented by Formula (I) or the pharmaceutically acceptable salt thereof can be used at 0.1 to 20 moles, preferably 0.2 to 5 moles, per mole of methotrexate. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.1 to 2 moles and more preferably from 0.2 to 1 moles, per mole of methotrexate. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.5 to 10 moles and more preferably from 1 to 5 moles, per mole of methotrexate.

When the additional compound having an antitumor effect is doxorubicin (antitumor antibiotic), the compound represented by Formula (I) or the pharmaceutically acceptable salt thereof can be used at 0.05 to 20 moles, preferably 0.1 to 10 moles, per mole of doxorubicin. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.05 to 2 moles and more preferably from 0.1 to 1 moles, per mole of doxorubicin. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.1 to 20 moles and more preferably 0.5 to 10 moles, per mole of doxorubicin.

When the additional compound having an antitumor effect is temozolomide (alkylating agent), the compound represented by Formula (I) or the pharmaceutically acceptable salt thereof can be used at 0.001 to 1 moles, preferably 0.01 to 0.5 moles, per mole of temozolomide. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.001 to 0.1 moles and more preferably from 0.01 to 0.05 moles, per mole of temozolomide. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.01 to 1 moles and more preferably from 0.05 to 0.5 moles, per mole of temozolomide.

When the additional compound having an antitumor effect is cyclophosphamide (alkylating agent), the compound represented by Formula (I) or the pharmaceutically acceptable salt thereof can be used at 0.001 to 1 moles, preferably 0.01 to 0.3 moles, per mole of cyclophosphamide. In the case of administering each day the daily dose of the compound represented by Formula (I) or the pharmaceutically acceptable salt thereof, the compound represented by Formula (I) or the pharmaceutically acceptable salt thereof can be used in an amount ranging from preferably 0.001 to 0.1 moles and more preferably from 0.01 to 0.05 moles, per mole of cyclophosphamide. In the case of administering every other day the daily dose of the compound represented by Formula (I) or the pharmaceutically acceptable salt thereof, the compound represented by Formula (I) or the pharmaceutically acceptable salt thereof can be used in an amount ranging from preferably 0.005 to 1 moles and more preferably from 0.01 to 0.2 moles, per mole of cyclophosphamide.

In the second embodiment, the present invention also provides a pharmaceutical composition comprising a compound represented by Formula (I) or a pharmaceutically acceptable salt thereof, and one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

The pharmaceutical composition of the present invention contains the compound represented by Formula (I) or the pharmaceutically acceptable salt thereof, and the one or more additional compound(s) having an antitumor effect or pharmaceutically acceptable salt(s) thereof as active ingredients in the same composition, whereas the above-described combination preparation comprises these active ingredients in separate preparations. The mixing ratios of the compound represented by Formula (I) or the pharmaceutically acceptable salt thereof, and the one or more additional compound(s) having an antitumor effect or pharmaceutically acceptable salt(s) thereof in the composition may be within the range described above.

In the third embodiment, the present invention also provides an antitumor effect enhancer for one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent, the antitumor effect enhancer comprising a compound represented by Formula (I) or a pharmaceutically acceptable salt thereof as an active ingredient.

In the fourth embodiment, the present invention also provides an antitumor agent comprising a compound represented by Formula (I) or a pharmaceutically acceptable salt thereof, wherein the antitumor agent is concomitantly used with one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

In the fifth embodiment, the present invention further provides a kit for malignant tumor treatment comprising a compound represented by Formula (I) or a pharmaceutically acceptable salt thereof, and one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

In the sixth embodiment, the present invention further provides an antitumor agent comprising a compound represented by Formula (I) or a pharmaceutically acceptable salt thereof, wherein the antitumor agent is for the treatment of a cancer patient given one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

In the seventh embodiment, the present invention further provides use of a compound represented by Formula (I) or a pharmaceutically acceptable salt thereof in the manufacture of an antitumor effect enhancer for one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

In the eighth embodiment, the present invention further provides use of a compound represented by Formula (I) or a pharmaceutically acceptable salt thereof in the enhancement of the antitumor effect of one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent.

In the ninth embodiment, the present invention further provides a method for treating a tumor comprising administering a compound represented by Formula (I) or a pharmaceutically acceptable salt thereof, and one or more additional compound(s) having an antitumor effect or pharmaceutically acceptable salt(s) thereof, selected from an antimetabolite, an alkaloid antitumor agent, a platinum-containing drug, a molecular targeting drug, an antitumor antibiotic, and an alkylating agent to a patient in need thereof.

The embodiments of the present invention have been confirmed to be highly effective not only for a tumor having wild-type FGFR but for a tumor having amplified or mutated FGFR. Accordingly, the target to be treated in the present invention also includes, but is not particularly limited to, tumors having wild-type FGFR, or amplified or mutated FGFR. Although the target to be treated in the present invention is not limited to a tumor having specific wild-type FGFR, it is preferably a tumor having wild-type FGFR3. Also, although the target to be treated in the present invention is not limited to specific FGFR amplification, it is preferably a tumor having FGFR1 or FGFR2 amplification. Furthermore, although the target to be treated in the present invention is not limited to a tumor having a specific FGFR mutation, it is preferably a tumor having an FGFR2 mutation.

The compound represented by Formula (I) or the pharmaceutically acceptable salt thereof can be effectively used even for a tumor having resistance to the additional compound having an antitumor effect. For example, an EGFR inhibitor gefitinib is known to reduce its effects due to long-term use. However, its concomitant use with the compound represented by Formula (I) or the pharmaceutically acceptable salt thereof can remarkably decrease the survival rate of tumor cells. Moreover, the compound represented by Formula (I) or the pharmaceutically acceptable salt thereof can be effectively used even for a tumor having resistance to an FGFR inhibitor other than the compound represented by Formula (I) or the pharmaceutically acceptable salt thereof.

EXAMPLES

The present invention is explained in detail below with reference to Examples; however, the scope of the present invention is not limited to these Examples. Although the present invention is fully explained by means of Examples, it should be understood that persons skilled in the art can make various changes or modifications. Accordingly, such changes or modifications are encompassed in the present invention without departing from the scope of the present invention. Various reagents used in Examples were commercially available products unless otherwise specified.

Example 1: Measurement of Antitumor Effect of Concomitant Use of Compound 1 and S-1 on Tumor from Human Gastric Cancer Cell Line SNU-16 Subcutaneously Implanted to Nude Mouse With reference to Clin Cancer Res. 2013; 19 (9): 2572-83, a cell suspension of a human gastric cancer line SNU-16 (available from American Type Culture Collection) was subcutaneously implanted to 6-week-old male BALB/cAJcl-nu/nu mice (CLEA Japan, Inc.) at $8 \times 10^6$ cells/mouse. For grouping (n=10/group), after the cell suspension implantation, tumor volumes (TV) were calculated according to the expression given below, and mice having TV of 100 to 300 mm$^3$ were selected and assigned such that average TV was equal among groups. The day at which the grouping was carried out was defined as Day 0.

$$TV(mm^3) = (Major\ axis \times Minor\ axis^2)/2\ (units\ for\ the\ major\ axis\ and\ the\ minor\ axis\ were\ mm).$$

Compound 1 at 5 or 15 mg/kg/day and tegafur/gimeracil/oteracil potassium (S-1; mixing molar ratio: 1:0.4:1) at 8.3 mg/kg/day (in terms of tegafur) were orally administered once a day for 14 days.

The dose of Compound 1 was set to 15 mg/kg which corresponded to an effective dose for this mouse subcutaneous implantation model and a low dose of 5 mg/kg for confirming the effect of concomitant use. The dose of S-1 was set in consideration of the maximum tolerated dose for nude mice, etc.

Antitumor effects were evaluated by using the difference between the average values of relative tumor volumes (RTV) in two groups to be compared at the day of assessment, as an index. RTV was calculated according to the expression given below from TV values on the day of measurement and on the day of grouping. Also, T/C (%) was calculated from the average RTV values in medicine administration groups and a control group.

$$RTV = (TV\ on\ the\ day\ of\ measurement)/(TV\ on\ the\ day\ of\ grouping)$$

$$T/C\ (\%) = (Average\ RTV\ in\ each\ medicine\ administration\ group\ on\ the\ day\ of\ assessment)/(Average\ RTV\ in\ the\ control\ group\ on\ the\ day\ of\ assessment) \times 100$$

As a result, each of the treatment with Compound 1 (5 and 15 mg/kg) and the treatment with S-1 (8.3 mg/kg) inhibited alone the growth of subcutaneously implanted SNU-16 tumor, with respective T/C (%) on the day of assessment being 83.6%, 69.0% and 84.3%. By contrast, the concomitant treatment with 5 or 15 mg/kg Compound 1 and 8.3 mg/kg S-1 in combination inhibited tumor growth stronger than the treatment with each medicine alone, with respective T/C (%) being 54.4% and 43.9%.

Figure 1B:
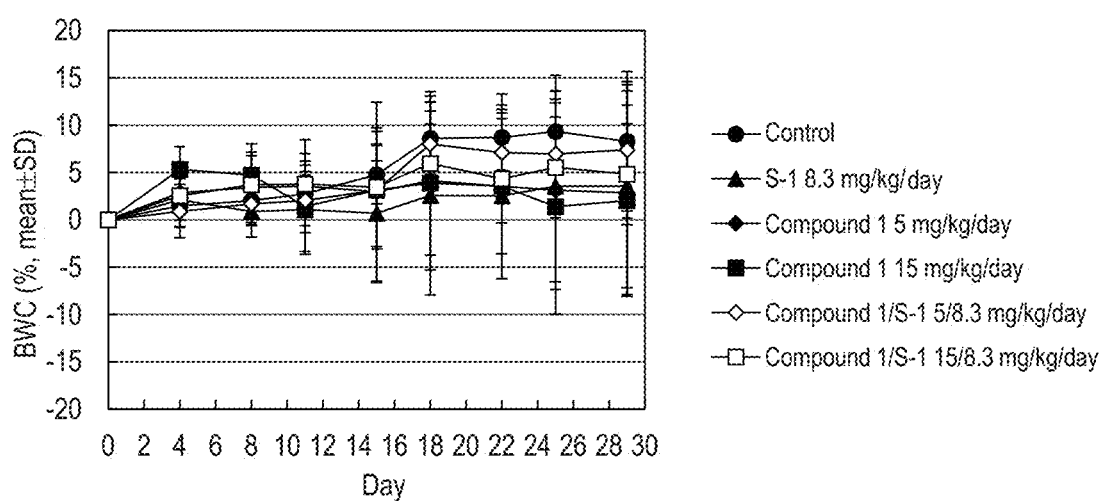
FIG. 1B shows the antitumor effects of Compound 1 and S-1 used alone or concomitantly. The rates of mouse body weight change in medicine administration groups and a control group are shown.
Figure 1C:
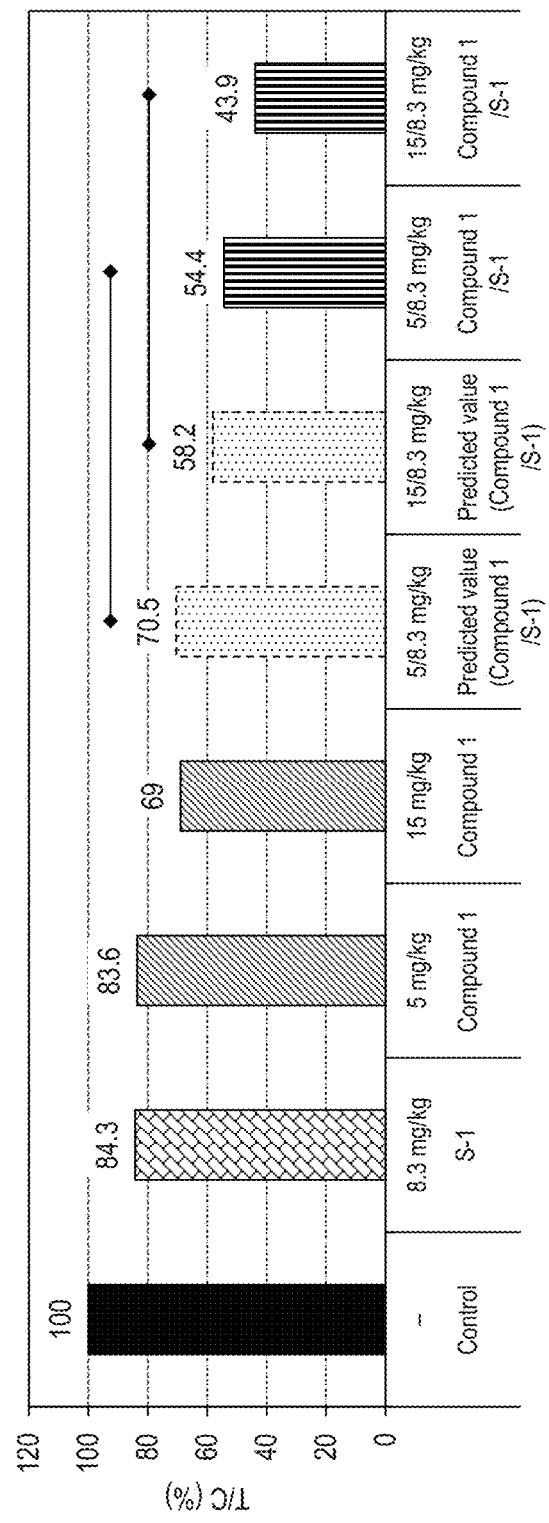
FIG. 1C shows the antitumor effects of Compound 1 and S-1 used alone or concomitantly. The effects (T/C (%)) of Compound 1 and S-1 used alone or concomitantly at Day 15 are shown.

The tumor growth inhibitory effect of Compound 1 and S-1 concomitantly used exceeded the computationally predicted effect of concomitant use of both the medicines (T/C=70.5% and 58.2%) based on the effect of each medicine used alone as an index, demonstrating that the concomitant use exhibits synergistic effects (P<0.05; Bliss method, Student's t test). These results are shown in FIGS. 1A and 1C. On the other hand, the average rate of body weight change in the Compound 1/S-1 concomitant use group exhibited no significant difference from the rate of body weight change in each medicine group (FIG. 1B).

Example 2: Measurement of Antitumor Effect of Concomitant Use of Compound 1 and Paclitaxel on Tumor from Human Gastric Cancer Cell Line SNU-16 Subcutaneously Implanted to Nude Mouse Similarly as in Example 1, a cell suspension of a human gastric cancer line SNU-16 was subcutaneously implanted to 6-week-old male BALB/cAJcl-nu/nu mice (CLEA Japan, Inc.) at $8 \times 10^6$ cells/mouse. For grouping (n=10/group), after the cell suspension implantation, mice having a tumor volume (TV) of 100 to 300 mm$^3$ were selected and assigned such that average TV was equal among groups.

Compound 1 was orally administered each day at 5 or 15 mg/kg/day for 14 days once a day. Paclitaxel was administered at a single dose of 60 mg/kg/day based on the maximum soluble quantity of the dosing solution by injection to the tail vein at Day 1.

Antitumor effects were evaluated by using the difference between the average values of relative tumor volumes (RTV) in two groups to be compared on the day of assessment, as an index. Also, T/C (%) was calculated from the average RTV values of medicine administration groups and a control group.

As a result, each of the treatment with Compound 1 (5 and mg/kg) and the treatment with paclitaxel (60 mg/kg) inhibited alone the growth of subcutaneously implanted SNU-16 tumor, with respective T/C (%) on the day of assessment being 83.6%, 69.0% and 12.9%. By contrast, the concomitant treatment with 5 or 15 mg/kg Compound 1 and 60 mg/kg paclitaxel in combination inhibited tumor growth stronger than the treatment with each medicine alone, with respective T/C (%) being 3.1% and 1.5%.

Figure 2A:
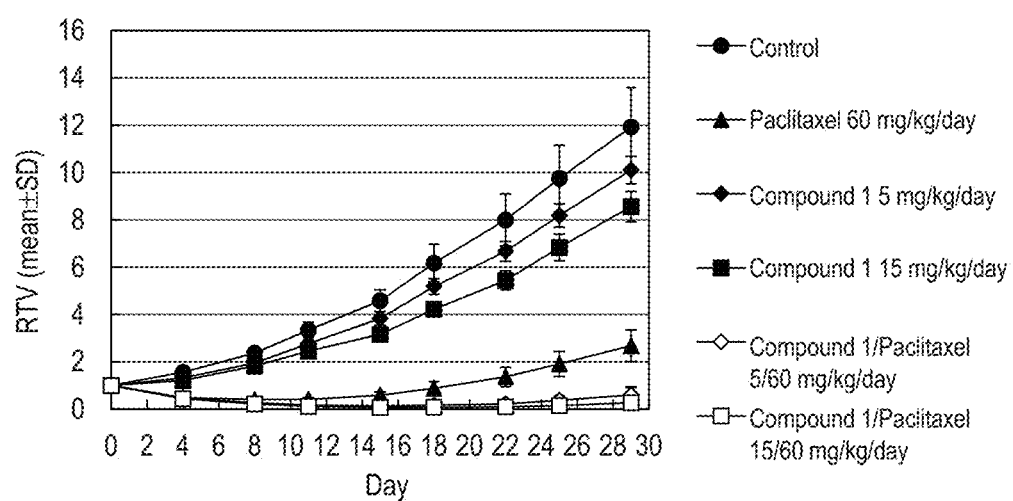
FIG. 2A shows the antitumor effects of Compound 1 and paclitaxel used alone or concomitantly. The relative tumor volumes (RTV) in medicine administration groups and a control group are shown.
Figure 2B:
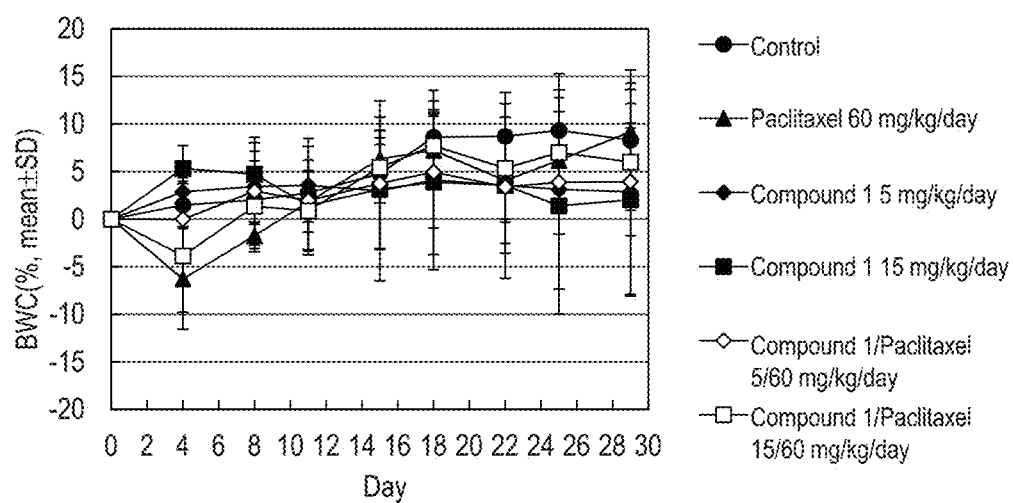
FIG. 2B shows the antitumor effects of Compound 1 and paclitaxel used alone or concomitantly. The rates of mouse body weight change in medicine administration groups and a control group are shown.
Figure 2C:
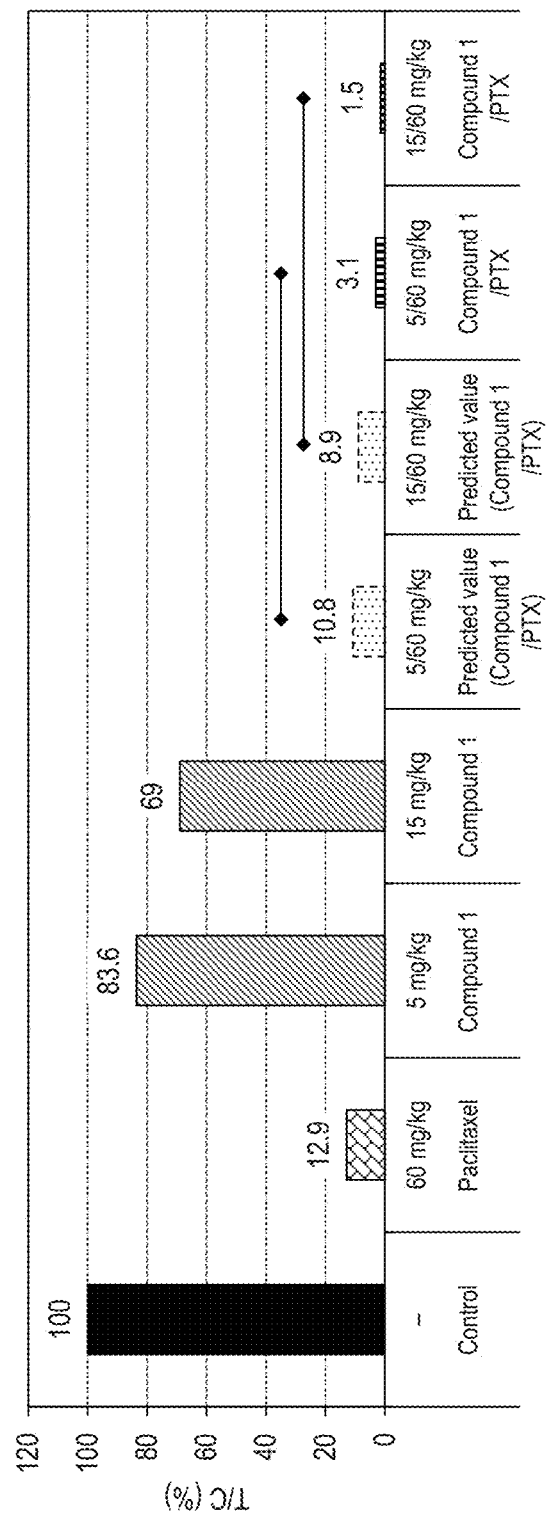
FIG. 2C shows the antitumor effects of Compound 1 and paclitaxel used alone or concomitantly. The effects (T/C (%)) of Compound 1 and paclitaxel used alone or concomitantly at Day 15 are shown.

The tumor growth inhibitory effect of Compound 1 and paclitaxel concomitantly used exceeded the computationally predicted effect of concomitant use of both the medicines (T/C=10.8% and 8.9%) based on the effect of each medicine used alone as an index, demonstrating that the concomitant use exhibits synergistic effects (P<0.05; Bliss method, Student's t test). These results are shown in FIGS. 2A and 2C. On the other hand, transient decrease in body weight was observed in the mice after paclitaxel administration, indicating a side effect of paclitaxel. The average rate of body weight change in the Compound 1/paclitaxel concomitant use group exhibited no significant difference from the rate of body weight change in each medicine group (FIG. 2B).

Example 3: Measurement of Antitumor Effect of Concomitant Use of Compound 1 and Cisplatin on Tumor from Human Endometrial Cancer Line AN3CA Subcutaneously Implanted to Nude Mouse With reference to Gynecol Oncol. 2014; 132 (2): 468-73, a cell suspension of a human endometrial cancer line AN3CA (available from American Type Culture Collection) was subcutaneously implanted to 6-week-old female BALB/cAJcl-nu/nu mice (CLEA Japan, Inc.) at $1 \times 10^7$ cells/mouse. An engrafted tumor was removed from the mice, chopped into fragments of 2 mm square, and then subcutaneously implanted to 6-week-old female BALB/cAJcl-nu/nu mice. For grouping (n=6/group), after the implantation, mice having a tumor volume (TV) of 100 to 300 mm$^3$ were selected and assigned such that average TV was equal among groups.

Compound 1 was orally administered each day at 15 mg/kg/day for 14 days once a day. Cisplatin was administered at 7 mg/kg/day from the tail vein at Day 1. The cisplatin dose of 7 mg/kg corresponded to the maximum tolerated dose for single-dose administration to nude mice.

Antitumor effects were evaluated by using the difference between the average values of relative tumor volumes (RTV) in two groups to be compared on the day of assessment, as an index. Also, T/C (%) was calculated from the average RTV values in medicine administration groups and a control group.

As a result, each of the treatment with Compound 1 (15 mg/kg) and the treatment with cisplatin (7 mg/kg) inhibited alone the growth of subcutaneously implanted AN3CA tumor, with respective T/C (%) on the day of assessment being 46.0% and 53.0%. By contrast, the concomitant treatment with 15 mg/kg Compound 1 and 7 mg/kg cisplatin in combination inhibited tumor growth stronger than the treatment with each medicine alone, with T/C (%) being 14.9%.

Figure 3A:
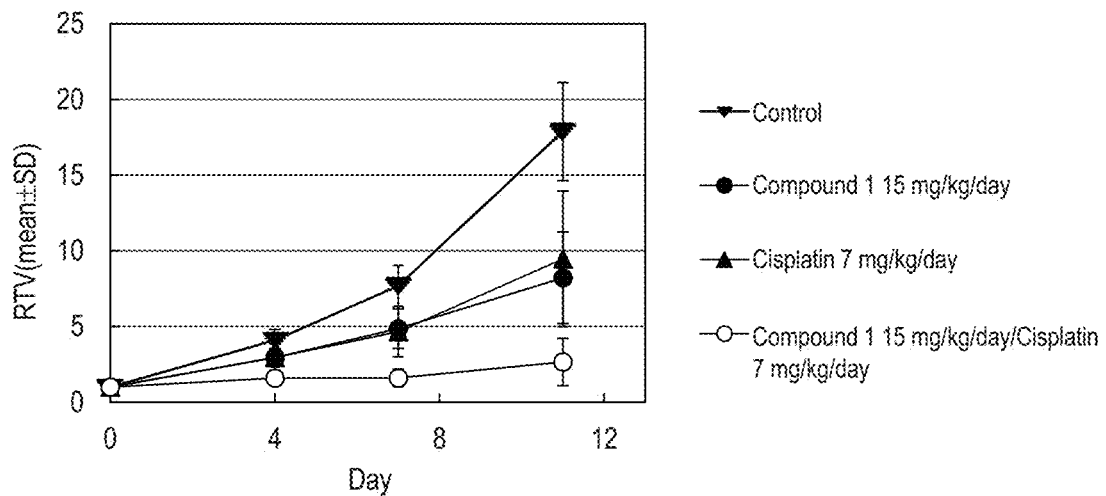
FIG. 3A shows the antitumor effects of Compound and cisplatin used alone or concomitantly. The relative tumor volumes (RTV) in medicine administration groups and a control group are shown.
Figure 3B:
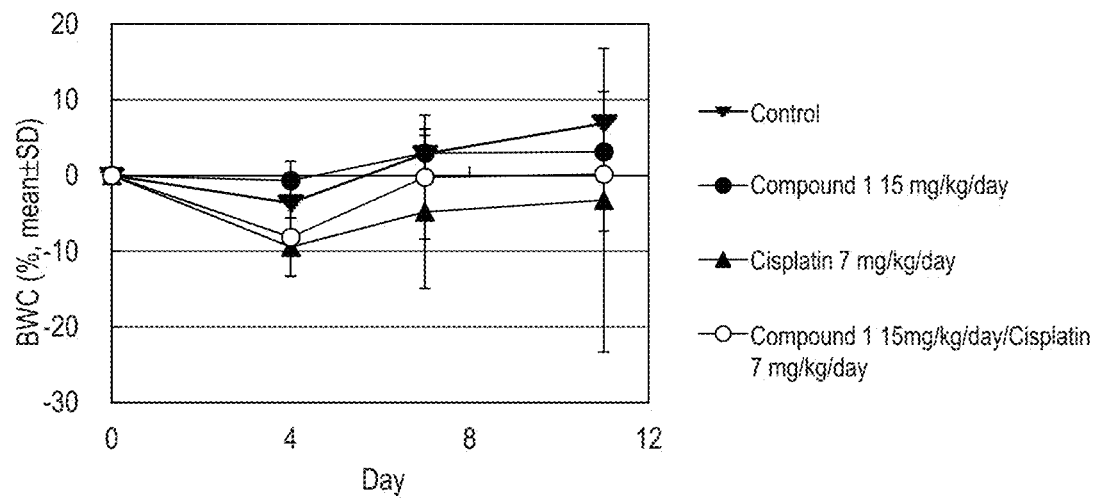
FIG. 3B shows the antitumor effects of Compound and cisplatin used alone or concomitantly. The rates of mouse body weight change in medicine administration groups and a control group are shown.
Figure 3C:
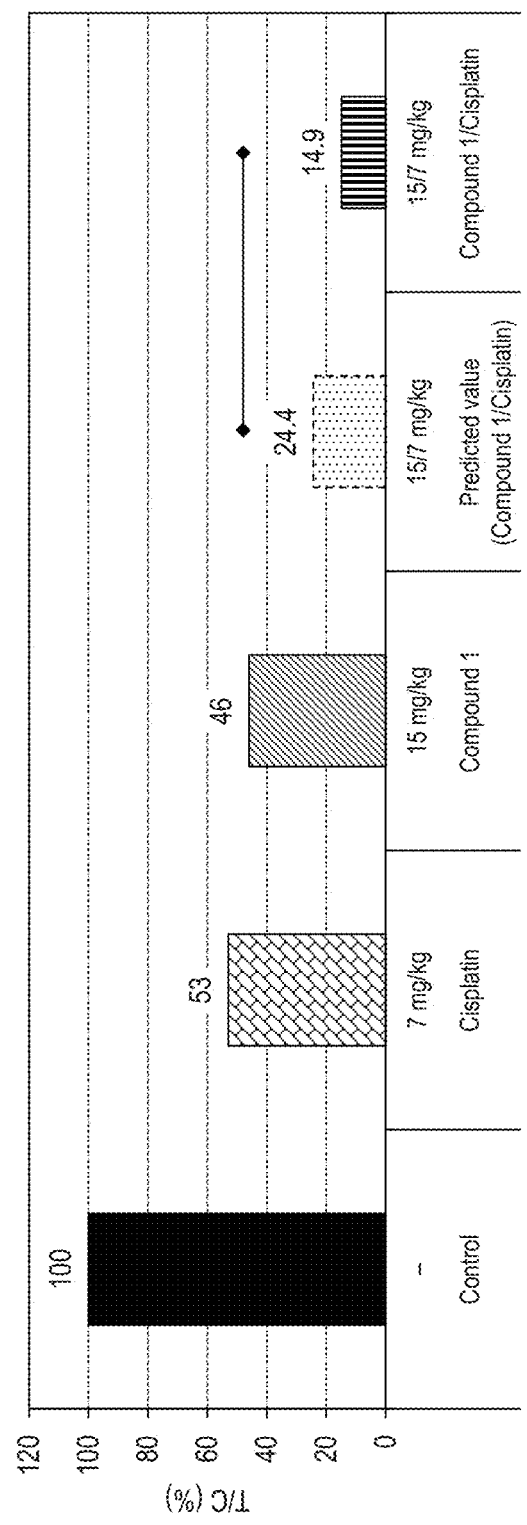
FIG. 3C shows the antitumor effects of Compound 1 and cisplatin used alone or concomitantly. The effects (T/C (%)) of Compound 1 and cisplatin used alone or concomitantly at Day 11 are shown.

The tumor growth inhibitory effect of Compound 1 and cisplatin concomitantly used had statistically significant enhancing effects on the effect of each medicine used alone (P<0.05; Aspin-Welch t test). Also, the tumor growth inhibitory effect of Compound 1 and cisplatin concomitantly used exceeded the computationally predicted effect of concomitant use of both the medicines (T/C=24.4%) based on the effect of each medicine used alone as an index (Bliss method). These results are shown in FIGS. 3A and 3C. On the other hand, transient decrease in body weight was observed in the mice after cisplatin administration, indicating a side effect of cisplatin. Time-dependent change in the body weights of the mice was not exacerbated by concomitant use of Compound 1 and cisplatin, as compared with change in the body weights of the mice treated with cisplatin alone (FIG. 3B).

Example 4: Measurement of Antitumor Effect of Concomitant Use of Compound 1 and Gemcitabine on Tumor from Human Endometrial Cancer Line AN3CA Subcutaneously Implanted to Nude Mouse Similarly as in Example 3, a cell suspension of a human endometrial cancer line AN3CA was subcutaneously implanted to 6-week-old female BALB/cAJcl-nu/nu mice (CLEA Japan, Inc.) at $1 \times 10^7$ cells/mouse. An engrafted tumor was removed from the mice, chopped into fragments of 2 mm square, and then subcutaneously implanted to 6-week-old female BALB/cAJcl-nu/nu mice. For grouping (n=6/group), after the implantation, mice having a tumor volume (TV) of 100 to 300 mm³ were selected and assigned such that average TV was equal among groups.

Compound 1 was orally administered each day at 15 mg/kg/day for 14 days. Gemcitabine was administered at 100 mg/kg/day from the tail vein at Day 1 and Day 8. The dose of gemcitabine was set to 100 mg/kg at which a drug effect can be expected, on the basis of the report of J Pharmacol. Exp Ther., 2008; 325: 484-490, etc.

Antitumor effects were evaluated by using the difference between the average values of relative tumor volumes (RTV) in two groups to be compared on the day of assessment, as an index. Also, T/C (%) was calculated from the average RTV values in medicine administration groups and a control group.

Each of the treatment with Compound 1 (15 mg/kg) and the treatment with gemcitabine (100 mg/kg) inhibited alone the growth of subcutaneously implanted AN3CA tumor, with respective T/C (%) on the day of assessment being 42.1% and 75.5%. By contrast, the concomitant treatment with 15 mg/kg Compound 1 and 100 mg/kg gemcitabine in combination inhibited tumor growth stronger than the treatment with each medicine alone, with T/C (%) being 24.7%.

Figure 4A:
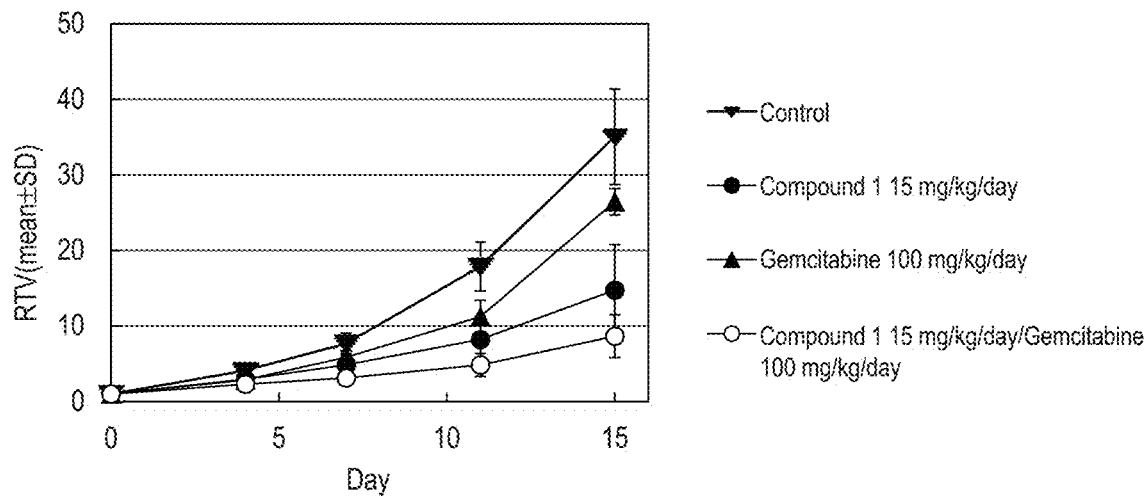
FIG. 4A shows the antitumor effects of Compound 1 and gemcitabine used alone or concomitantly. The relative tumor volumes (RTV) in medicine administration groups and a control group are shown.
Figure 4B:
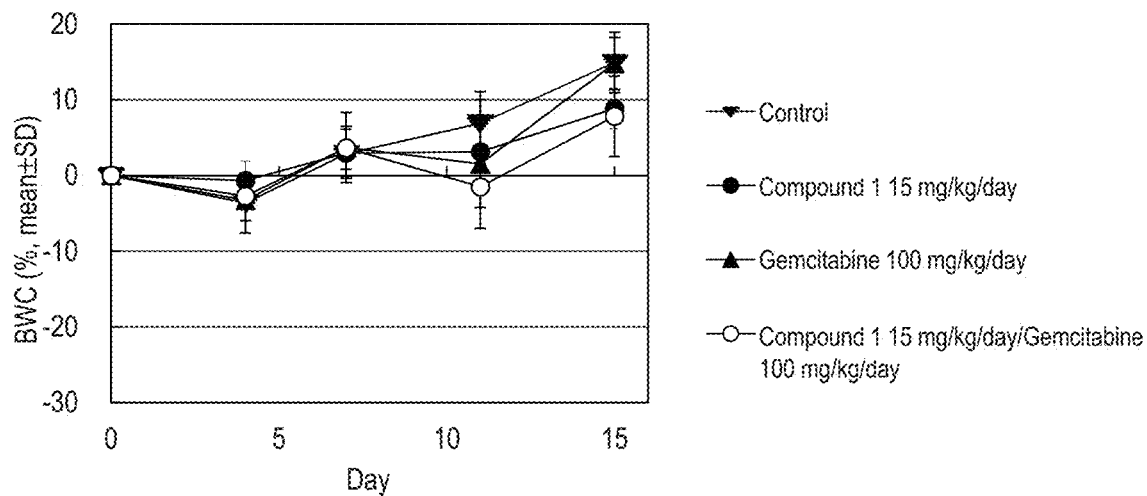
FIG. 4B shows the antitumor effects of Compound 1 and gemcitabine used alone or concomitantly. The rates of mouse body weight change in medicine administration groups and a control group are shown.

The tumor growth inhibitory effect of Compound 1 and gemcitabine concomitantly used tended to enhance the effect of Compound 1 used alone (P=0.0594; Aspin-Welch t test) and also had statistically significant enhancing effects on the effect of gemcitabine used alone (P<0.05; Aspin-Welch t test). The tumor growth inhibitory effect of Compound 1 and gemcitabine concomitantly used exceeded the computationally predicted effect of concomitant use of both the medicines (T/C=31.8%) based on the effect of each medicine used alone as an index (Bliss method). These results are shown in FIGS. 4A and 4C. On the other hand, time-dependent change in the body weights of the mice was not remarkably exacerbated by concomitant use of Compound 1 and gemcitabine, as compared with change in the body weights of the mice treated with gemcitabine alone (FIG. 4B).

Example 5: Measurement of Antitumor Effect of Concomitant Use of Compound 1 and Everolimus on Tumor from Human Endometrial Cancer Line AN3CA Subcutaneously Implanted to Nude Mouse Similarly as in Example 3, a cell suspension of a human endometrial cancer line AN3CA was subcutaneously implanted to 6-week-old female BALB/cAJcl-nu/nu mice (CLEA Japan, Inc.) at 1×10⁷ cells/mouse. An engrafted tumor was removed from the mice, chopped into fragments of 2 mm square, and then subcutaneously implanted to 6-week-old female BALB/cAJcl-nu/nu mice. For grouping (n=6/group), after the implantation, mice having a tumor volume (TV) of 100 to 300 mm³ were selected and assigned such that average TV was equal among groups.

Compound 1 was orally administered each day at 15 and 50 mg/kg/day for 14 days. Everolimus was orally administered each day at 2 mg/kg/day for 14 days. The dose of everolimus was set to 2 mg/kg at which a drug effect can be expected, on the basis of the report of Neoplasia, 2013; 15: 1391-1399, etc.

Antitumor effects were evaluated by using the difference between the average values of relative tumor volumes (RTV) in two groups to be compared on the day of assessment, as an index. Also, T/C (%) was calculated from the average RTV values in medicine administration groups and a control group.

Each of the treatment with Compound 1 (15 and 50 mg/kg) and the treatment with everolimus (2 mg/kg) inhibited alone the growth of subcutaneously implanted AN3CA tumor, with respective T/C (%) on the day of assessment being 33.3%, 12.6% and 27.1%. By contrast, the concomitant treatment with 15 or mg/kg Compound 1 and 2 mg/kg everolimus in combination inhibited the tumor growth stronger than the treatment with each medicine alone, with respective T/C (%) being 5.1% and 1.9%.

Figure 5A:
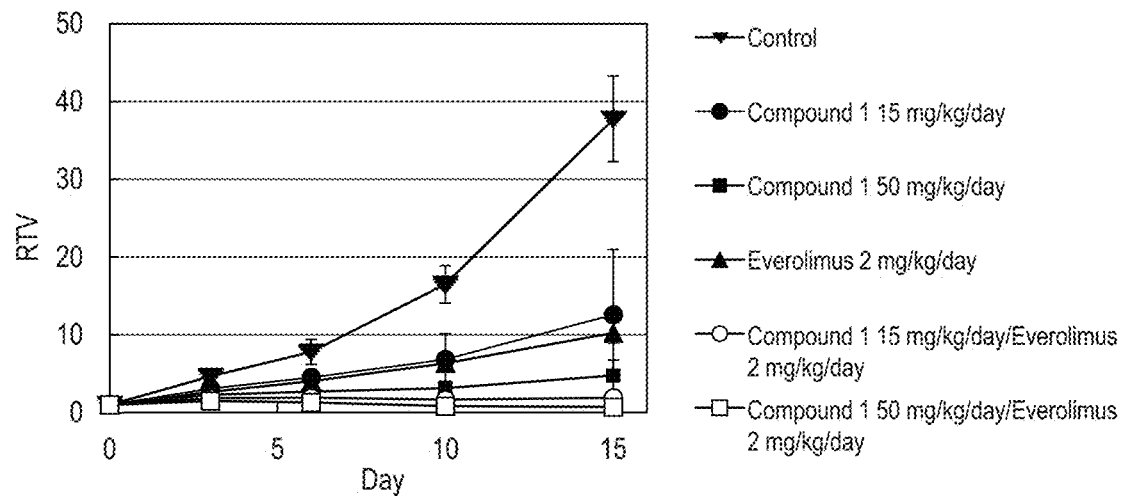
FIG. 5A shows the antitumor effects of Compound 1 and everolimus used alone or concomitantly. The relative tumor volumes (RTV) in medicine administration groups and a control group are shown.
Figure 5B:
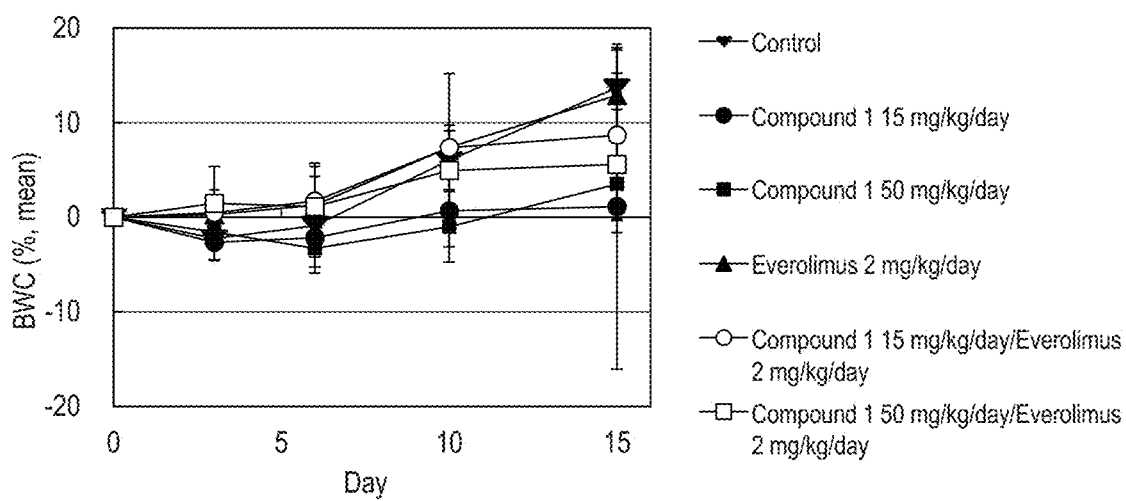
FIG. 5B shows the antitumor effects of Compound 1 and everolimus used alone or concomitantly. The rates of mouse body weight change in medicine administration groups and a control group are shown.
Figure 5C:
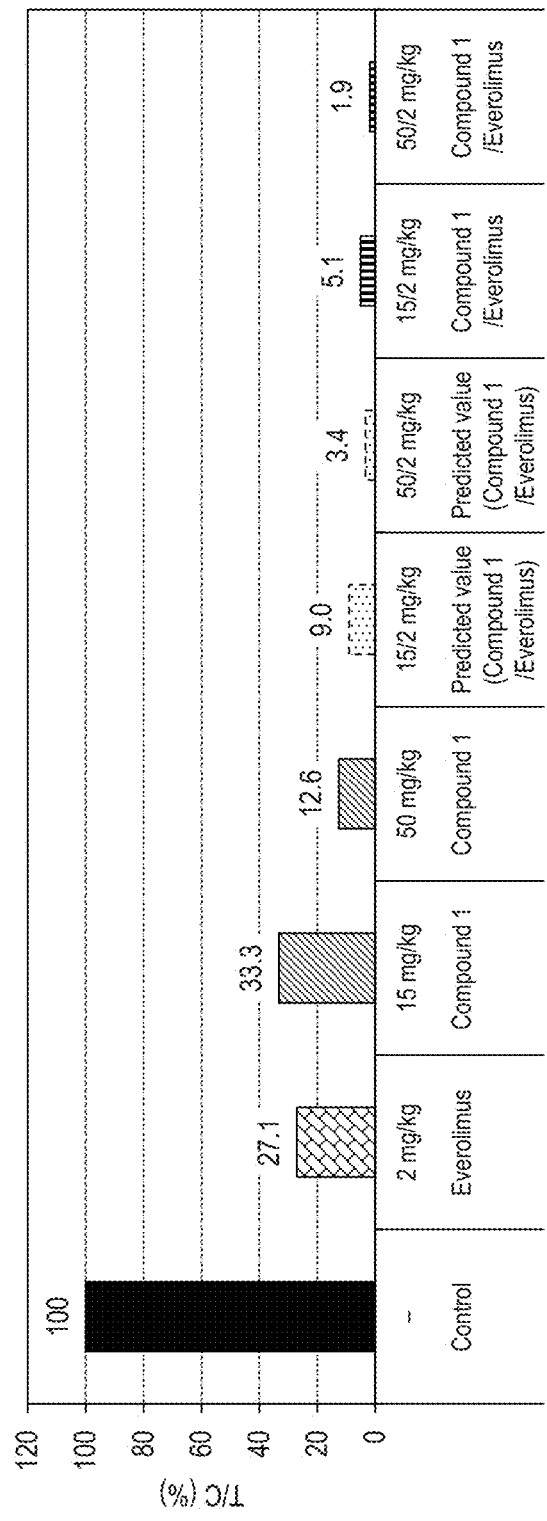
FIG. 5C shows the antitumor effects of Compound 1 and everolimus used alone or concomitantly. The effects (T/C (%)) of Compound 1 and everolimus used alone or concomitantly at Day 15 are shown.

The tumor growth inhibitory effect of Compound 1 and everolimus concomitantly used had statistically significant enhancing effects on the effect of each medicine used alone (P<0.05; Aspin-Welch t test). Also, the tumor growth inhibitory effect of Compound 1 and everolimus concomitantly used exceeded the computationally predicted effect of concomitant use of both the medicines (T/C=9.0% and 3.4%) based on the effect of each medicine used alone as an index (Bliss method). These results are shown in FIGS. 5A and 5C. On the other hand, time-dependent change in the body weights of the mice was not remarkably exacerbated by concomitant use of Compound 1 and everolimus, as compared with change in the body weights of the mice treated with everolimus alone (FIG. 5B).

Example 6: Evaluation of Tumor Growth Inhibitory Effect of Concomitant Use of Compound 1 and 5-FU In Vitro <A Materials and Methods>

With reference to Clin Cancer Res. 2013; 19 (9): 2572-83, a human gastric cancer cell line SNU-16 was cultured in a RPMI-1640 medium containing 10% fetal bovine serum. The cells were maintained at 37° C. under 5% $CO_2$ and subcultured at a ratio of 1:5 to 1:20 by 1 to 2 passages per week.

<Cell Survival Rate Assay>

Cell survival rate measurement was carried out using CellTiter-Glo (produced by Promega Corp.). The cells were collected by an ordinary method, then suspended in a RPMI-1640 medium containing 10% fetal bovine serum, and seeded in a 96-well plate. The number of cells seeded per well was set to 2000 cells/80 μL. After incubation at 37° C. for 24 hours under 5% $CO_2$, 10 μL of a medium containing Compound 1 and 5-FU or a vehicle (DMSO) was added to each well. The concentration of Compound 1 was set to 10 concentrations of a 3-fold dilution series with 100 μM as the highest final concentration. The concentration of 5-FU was set to 10 concentrations each of 3 types of 3-fold dilution series with 80, 100 and 200 μM as the highest concentrations. In addition to groups of each medicine alone, groups of both the medicines simultaneously added were prepared in parallel. After adding the medicine to the cells, the cells were further incubated at 37° C. for 72 hours under 5% $CO_2$. Cell survival rates were calculated by adding 100 μL of CellTiter-Glo solution to each well, incubating the cells at room temperature for 10 minutes, and then measuring the chemiluminescence intensity of each well using a plate reader (ARVO). The cell survival rates at the time of medicine addition were calculated as a ratio vs. the control group (100%) according to the following equation:

Cell survival rate (%)=(Chemiluminescence intensity at the time of medicine addition)/(Chemiluminescence intensity of the control group)×100

Also, Fa (fraction of affect) values were calculated by subtracting a 1/100 value of the cell survival rate from 1.

The concentration at which each medicine exhibited 50% cell growth inhibitory effect (IC$_{50}$) was determined using median effect analysis software CalcuSyn 2.0 (CalcuSyn, Inc.). Next, a combination index (CI) value at each combined concentration of the medicines was determined. The presence or absence of the combinatory effect of the two medicines was assessed as antagonistic, additive and synergistic effects when the CI value exceeded 1, was equal to 1, and was less than 1, respectively (Table 1; Pharmacol Rev. 2006; 58 (3): 621-81, BMC Complement Altern Med. 2013; 13: 212, and Anticancer Res. 2005; 25 (3B): 1909-17).

TABLE 1

| CI Range (upper limit) | Description |
| --- | --- |
| 0.1 | Very strong synergy |
| 0.3 | Strong synergy |
| 0.7 | Synergy |
| 0.85 | Moderate synergy |
| 0.9 | Slight synergy |
| 1 | Almost additive |
| 1.2 | Slight antagonism |
| 1.45 | Moderate antagonism |
| 3.3 | Antagonism |
| 10 | Strong antagonism |
| >10 | Very strong antagonism |

Combinations of Compound 1 and 5-FU concentrations that attained Fa=0.5 (corresponding to ED50), 0.75 (corresponding to ED75), or 0.9 (corresponding to ED90) were extracted on the basis of the Fa values in the SNU-16 cells calculated from the combined Compound 1 and 5-FU concentrations, and applied to linear curve fitting using CalcuSyn (HULINKS Inc.) to obtain CI.

<B Results>

Figure 6A:
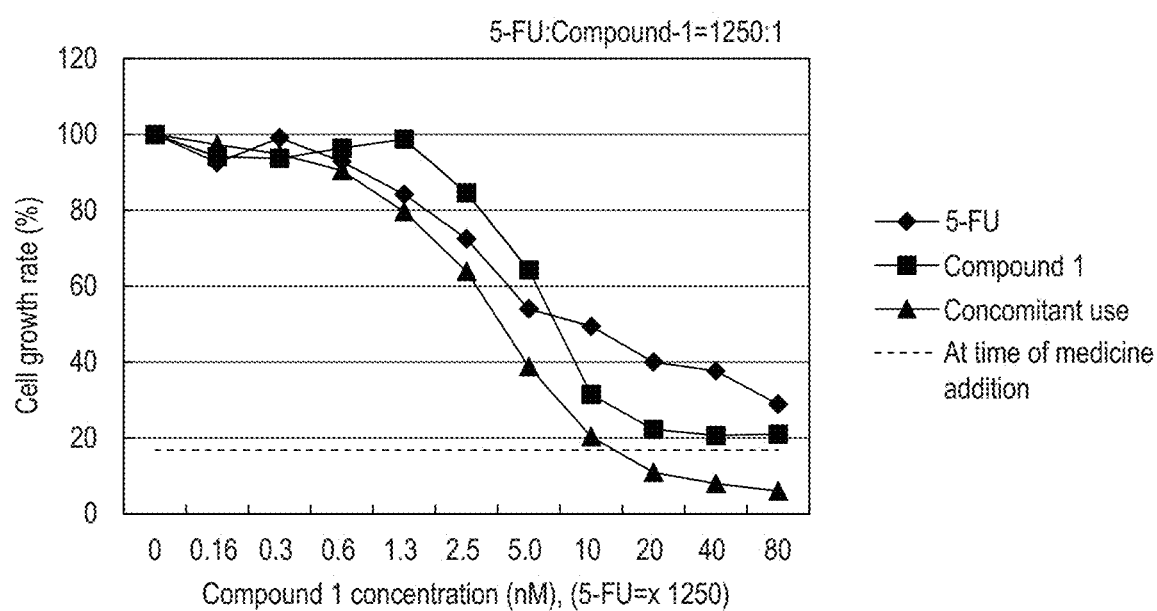
FIG. 6A shows the effect of concomitant use of Compound 1 and 5-FU on the cell growth rate of a SNU-16 cell line (5-FU:Compound 1=1250:1).
Figure 6B:
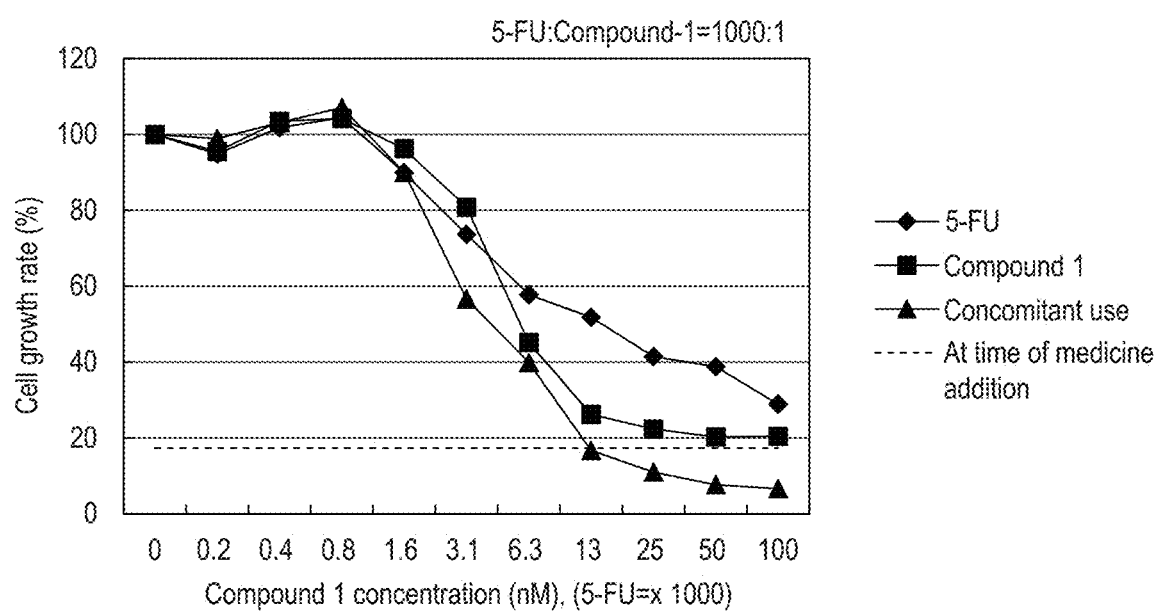
FIG. 6B shows the effect of concomitant use of Compound 1 and 5-FU on the cell growth rate of a SNU-16 cell line (5-FU:Compound 1=1000:1).
Figure 6C:
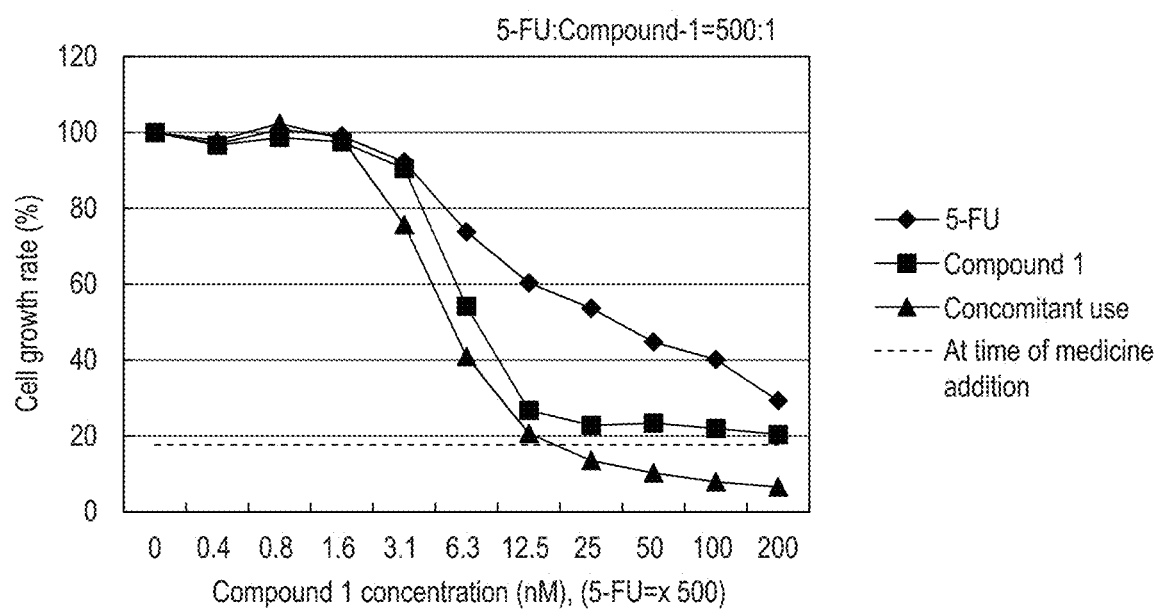
FIG. 6C shows the effect of concomitant use of Compound 1 and 5-FU on the cell growth rate of a SNU-16 cell line (5-FU:Compound 1=500:1).

Concomitant use of Compound 1 and 5-FU exhibited synergistic effects in all combinations with 3 concentration ratios used (FIGS. 6A to 6C). Particularly, synergistic effects as strong as CI=0.3 to 0.4 were found in the concentration range of 10 to 200 nM as the concentration of Compound 1 added. Table 2 below shows each combination index value obtained by a 5-FU:Compound 1 ratio of 1250:1, 1000:1, or 500:1 at each point in time when the cell growth inhibitory effect of concomitant use exhibited 50%, 75% and 90% (ED50, ED75, and ED90).

From the results described above, it was confirmed that a preferable effect of concomitant use is obtained when Compound 1 or a pharmaceutically acceptable salt thereof is used in the range of 0.0008 to 0.002 moles per mole of 5-FU.

TABLE 2

| | | Combination index value | | |
| --- | --- | --- | --- | --- |
| Cell line | 5-FU:Compound 1 | ED50 | ED75 | ED90 |
| SNU-16 | 1250:1 | 0.69 | 0.53 | 0.43 |
| | 1000:1 | 0.99 | 0.56 | 0.32 |
| | 500:1 | 0.51 | 0.40 | 0.32 |

Example 7: Evaluation of In Vitro Effect of Concomitant Use of Compound 1 and 5-FU, Paclitaxel, Cisplatin, or Gemcitabine <A Materials and Methods>

Human gastric cancer cell line SNU-16 (available from American Type Culture Collection), human breast cancer cell line MFM223 (available from European Collection of cell cultures), human lung cancer cell line H1581 (available from American Type Culture Collection), DMS114 (available from American Type Culture Collection), and LK2 (available from Health Science Research Resources Bank), human endometrial cancer line AN3CA (available from American Type Culture Collection) and MFE280 (available from DS Pharma Biomedical Co., Ltd.), and human bladder cancer cell line RT112/84 (available from European Collection of cell cultures) were cultured using any of RPMI-1640, DMEM, and MEM media containing 10% fetal bovine serum. The cells of each line were maintained at 37° C. under 5% $CO_2$ and subcultured at a ratio of 1:5 to 1:20 by 1 to 2 passages per week. The names of the cells used, carcinomas of their origins, and information on FGFR mutations are shown below.

TABLE 3

| Cell line | Carcinoma of origin | Information on FGFR gene alteration |
| --- | --- | --- |
| SNU-16 | Gastric cancer | FGFR2 amplification |
| MFM223 | Breast cancer | FGFR1, 2 amplification |
| H1581 | Lung cancer | FGFR1 amplification |
| DMS114 | Lung cancer | FGFR1 amplification |
| LK2 | Lung cancer | FGFR1 amplification |
| AN3CA | Endometrial cancer | FGFR2 K310R N549K |
| MFE280 | Endometrial cancer | FGFR2 S252W |
| RT112/84 | Bladder cancer | FGFR3 WT overexpression TACC3 translocation |

<Cell Survival Rate Assay>

Cell survival rate measurement was carried out using CellTiter-Glo. The cells were collected by an ordinary method, suspended in the above medium containing 10% fetal bovine serum, and then seeded in a 96-well plate. The number of cells seeded per well was set to 2000 cells/80 μL. The cells were incubated at 37° C. for 24 hours under 5% $CO_2$, and then, 10 μL of a medium containing Compound 1 and 5-FU, paclitaxel, cisplatin or gemcitabine, or a vehicle was added to each well.

In consideration of the sensitivity of the cells to each medicine,

Compound 1 was used at four concentrations in 3-fold dilution series starting at 10, 100 and 1000 nM, and zero concentration (DMSO);

5-FU was used at five concentrations in 3-fold dilution series starting at 10 and 100 μM, and zero concentration (DMSO);

paclitaxel was used at five concentrations in 3-fold dilution series starting at 100 nM, and zero concentration (DMSO);

cisplatin was used at five concentrations in 3-fold dilution series starting at 60 and 166 μM, and zero concentration (DMSO);

gemcitabine was used at five concentrations in 3-fold dilution series starting at 30, 100, 300 and 10000 nM, and zero concentration (DMSO), and each combination was studied.

After the medicine addition, the cells were further incubated at 37° C. for 72 hours under 5% $CO_2$. Cell survival rates were calculated by adding 100 μL of CellTiter-Glo solution to each well, incubating the cells at room temperature for 10 minutes, and then measuring chemiluminescence intensity using a plate reader ARVO. The cell survival rates at the time of medicine addition were calculated similarly as in Example 6.

Also, Fa (fraction of affect) values were calculated by subtracting a 1/100 value of the cell survival rate from 1.

Next, a combination index (CI) value at each combined concentration of the medicines was determined. The presence or absence of the effect of concomitant use of the two medicines was assessed as antagonistic, additive and synergistic effects when the CI value exceeded 1, was equal to 1, and was less than 1, respectively.

A CI value of concomitant use of Compound 1 and each chemotherapeutic agent was calculated for the 8 cell lines derived from 5 different cancer tissues. The CI value under each condition was plotted in FIG. 7. The abscissa of Figure depicts the concentration of Compound 1 (nM), and the concentrations of the antitumor agents were indicated in the legends.

<B Results>

Compound 1 concomitantly used with 5-FU, paclitaxel, cisplatin or gemcitabine exhibited synergistic effects of concomitant use (CI<1) in wide ranges of chemotherapeutic agent concentrations. As for the concentration of Compound 1 itself, synergistic effects of concomitant use were also confirmed in the range of 1.1 to 111 nM. Furthermore, the synergistic enhancement of the effects of the chemotherapeutic agents by Compound 1 was confirmed, irrespective of the action mechanisms of the chemotherapeutic agents. In addition, the cancer cell types on which synergistic effects of concomitant use were found had different types of FGFR aberrations (amplification, point mutation and translocation), demonstrating that the synergistic effects are exerted irrespective of the types of FGFR aberrations.

Figure 7A:
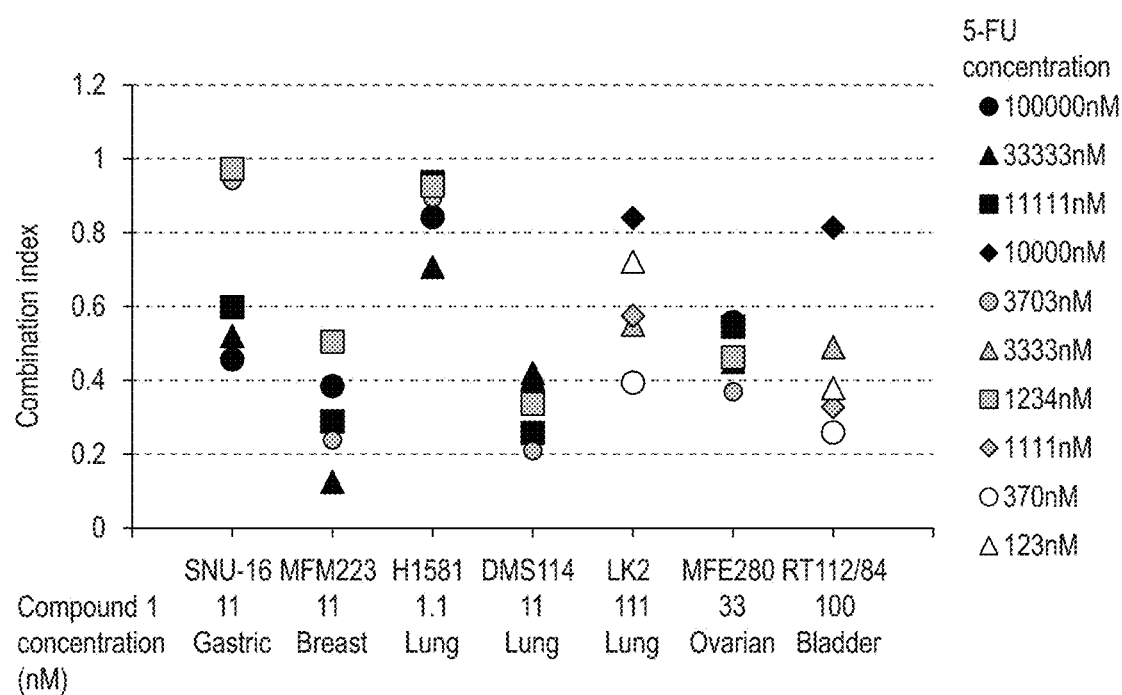
FIG. 7A shows the effect of concomitant use of Compound 1 on various carcinomas by combination index values. The effect of concomitant use of Compound 1 with varying concentrations of 5-FU is shown.

More specifically, as shown in FIG. 7A, concomitant use of Compound 1 and 5-FU exhibited synergistic effects (CI<1) in the concentration range of 11 to 100 nM as the concentrations of Compound 1 added, and exhibited synergistic effects as strong as CI<0.5 on the human lung cancer cell line DMS114.

Figure 7B:
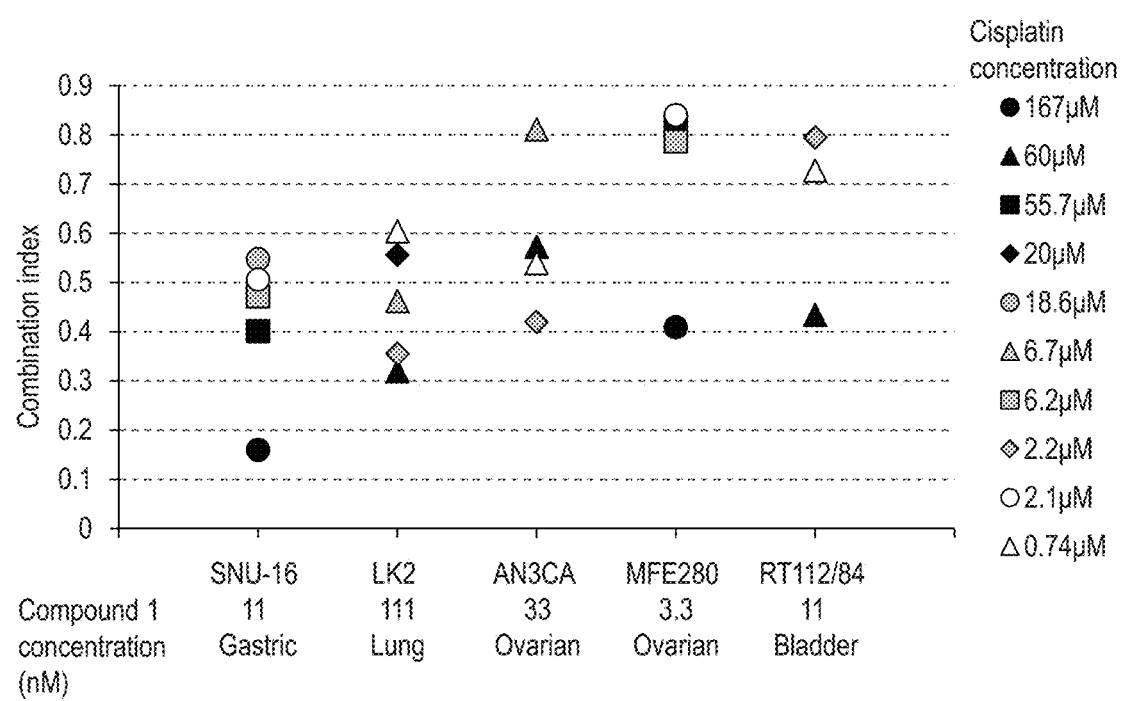
FIG. 7B shows the effect of concomitant use of Compound 1 on various carcinomas by combination index values. The effect of concomitant use of Compound 1 with varying concentrations of cisplatin is shown.

As shown in FIG. 7B, concomitant use of Compound 1 and cisplatin exhibited synergistic effects (CI<1) in the concentration range of 3.3 to 111 nM as the concentrations of Compound 1 added.

Figure 7C:
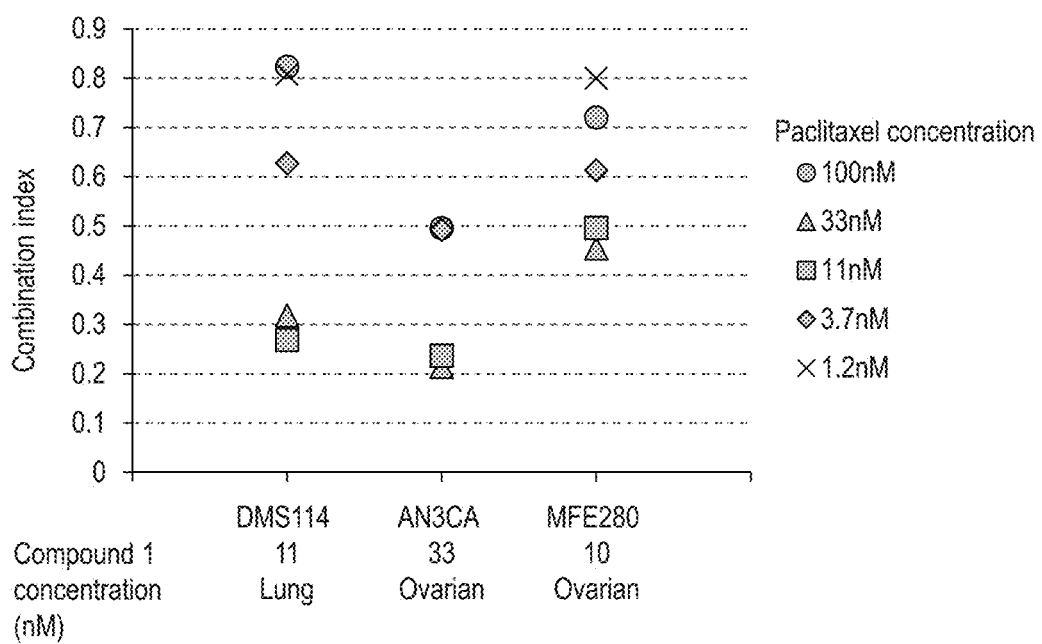
FIG. 7C shows the effect of concomitant use of Compound 1 on various carcinomas by combination index values. The effect of concomitant use of Compound 1 with varying concentrations of paclitaxel is shown.

As shown in FIG. 7C, concomitant use of Compound 1 and paclitaxel exhibited synergistic effects (CI<1) in the concentration range of 10 to 33 nM as the concentrations of Compound 1 added.

Figure 7D:
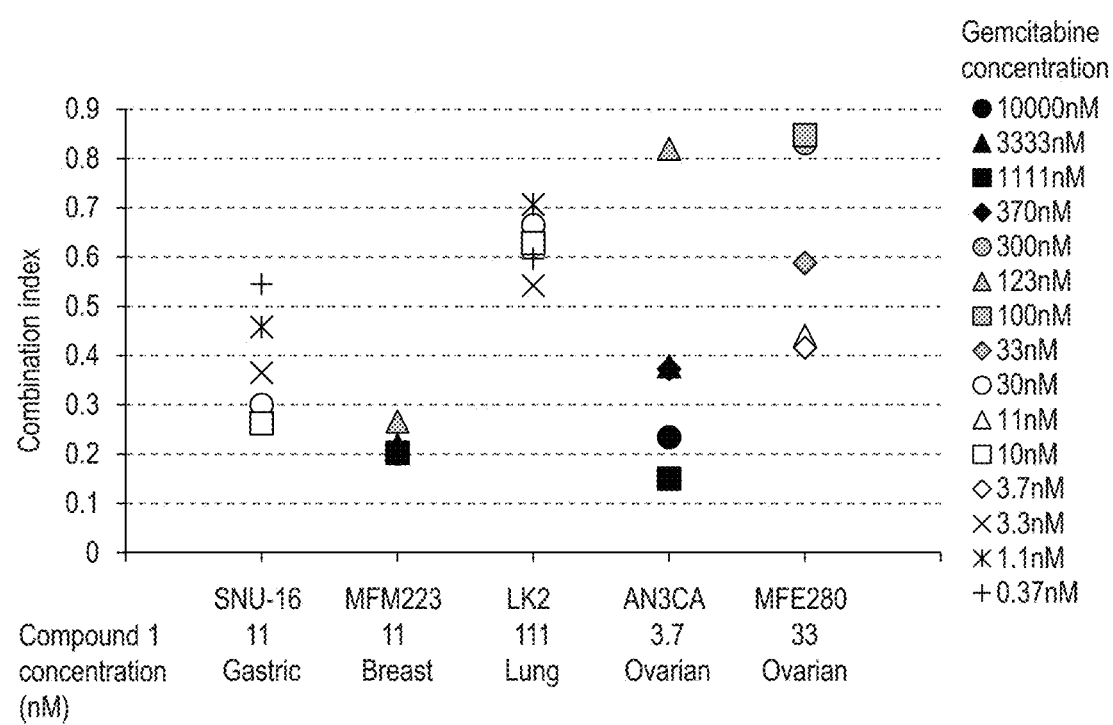
FIG. 7D shows the effect of concomitant use of Compound 1 on various carcinomas by combination index values. The effect of concomitant use of Compound 1 with varying concentrations of gemcitabine is shown.

As shown in FIG. 7D, concomitant use of Compound 1 and gemcitabine exhibited synergistic effects (CI<1) in the concentration range of 3.7 to 111 nM as the concentrations of Compound 1 added, and exhibited synergistic effects as strong as CI<0.5 on the human endometrial cancer line AN3CA.

Example 8: Evaluation of Effect of Concomitant Use of Compound 1 and AKT Inhibitor <A Materials and Methods>

A human endometrial cancer line AN3CA was cultured using a MEM medium containing 10% fetal bovine serum. The cells were maintained at 37° C. under 5% $CO_2$ and subcultured at a ratio of 1:5 to 1:20 by 1 to 2 passages per week.

<Cell Survival Rate Assay>

Cell survival rate measurement was carried out using CellTiter-Glo. The cells were collected by an ordinary method, suspended in the above medium containing 10% fetal bovine serum, and then seeded in a 96-well plate. The number of cells seeded per well was set to 2000 cells/80 μL. The cells were incubated at 37° C. for 24 hours under 5% $CO_2$, and then, 10 μL of a medium containing Compound 1 and an AKT inhibitor 8-[4-(1-aminocyclobutyl)phenyl]-9-phenyl-1,2,4-triazolo[3,4-f][1,6]naphthyridin-3(2H)-one (MK2206) dihydrochloride, or a vehicle was added to each well. The concentration of Compound 1 was set to 5 concentrations of a 3-fold dilution series with 0.03 μM as the highest final concentration. The concentration of MK2206 dihydrochloride was set to 4 concentrations of a 3-fold dilution series with 1 μM (in terms of a free form) as the highest concentration. A DMSO addition group was employed as a control, and Compound 1 alone, MK2206 dihydrochloride alone, and combinations of both the medicines were examined at each concentration. The cells were further incubated at 37° C. for 72 hours under 5% $CO_2$ (Day 3). 100 μL of CellTiter-Glo solution was added to each well, and the cells were incubated at room temperature for 10 minutes, followed by the measurement of chemiluminescence intensity using a plate reader ARVO. Growth inhibitory effects relative to the results of the vehicle group were calculated from the obtained data.

A cell growth inhibition rate at each medicine concentration was calculated as described below from the magnitude relationship between the chemiluminescence intensity of the control group on Day 3 (S) and the chemiluminescence intensity of the control group on the day of medicine addition (B), and a graph was created.

In the case of chemiluminescence intensity on Day 3 (S)>chemiluminescence intensity on the day of medicine addition (B), Cell growth rate=(Chemiluminescence intensity on Day 3 obtained from the treatment of medicine A at concentration $X$–$B$)/($S$–$B$)

In the case of chemiluminescence intensity on Day 3 (S)<chemiluminescence intensity on the day of medicine addition (B), Cell growth rate=–(Chemiluminescence intensity on Day 3 obtained from the treatment of medicine A at concentration $X$–$B$)/$B$ wherein medicine A corresponds to Compound 1 or MK2206 dihydrochloride, and concentration X represents any concentration of the dilution series.

<B Results>

Figure 8A:
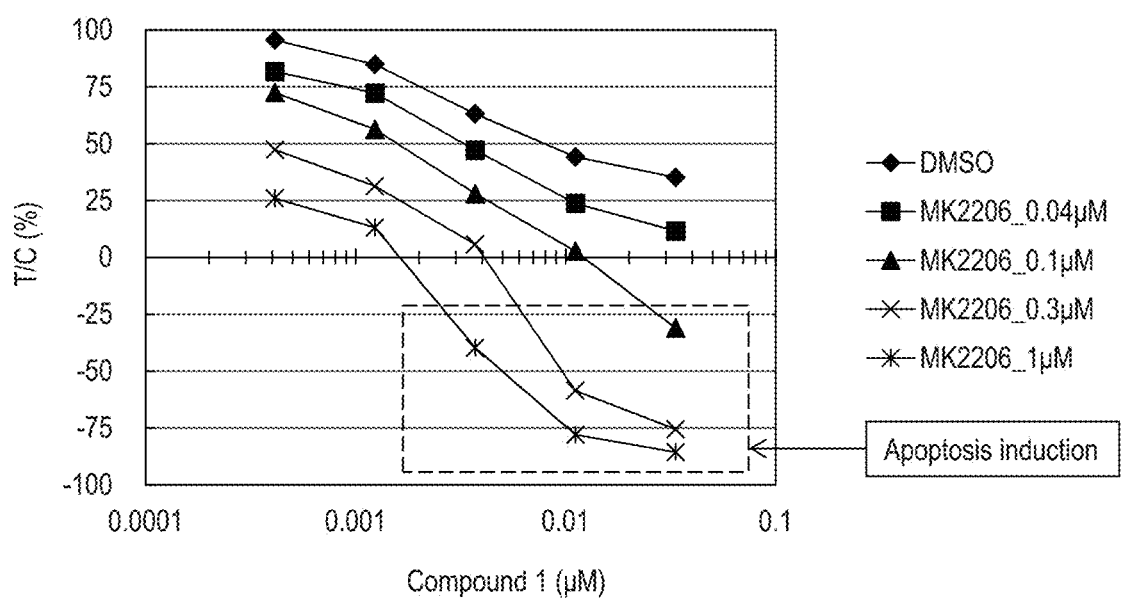
FIG. 8A shows that apoptosis is induced by concomitant use of an AKT inhibitor MK2206 and Compound 1. The effect of concomitant use of Compound 1 with varying concentrations of MK2206 is shown.
Figure 8B:
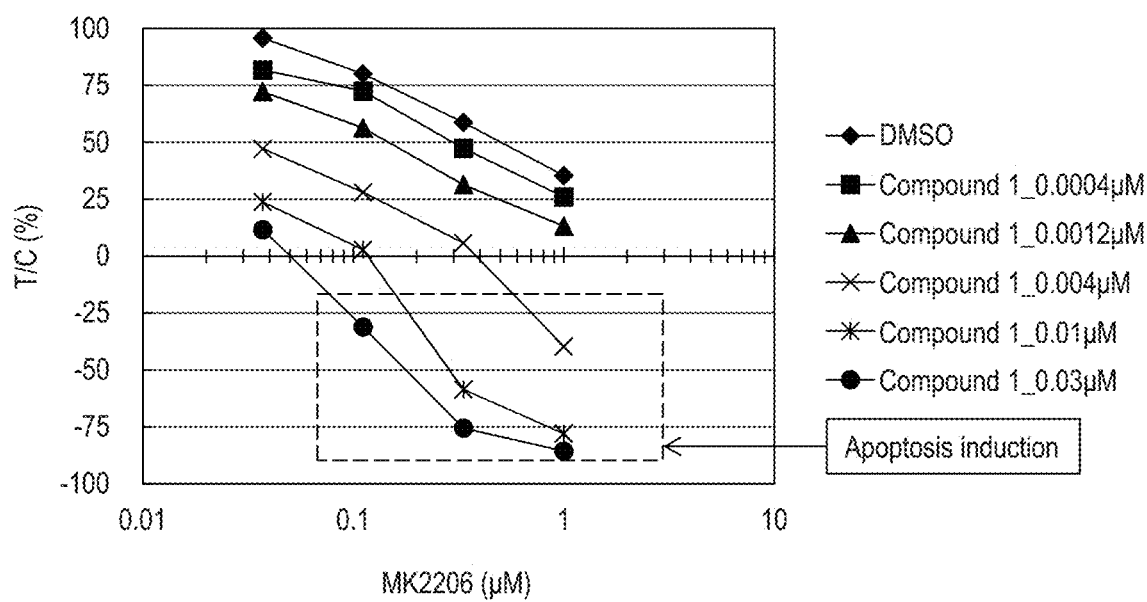
FIG. 8B shows that apoptosis is induced by concomitant use of an AKT inhibitor MK2206 and Compound 1. The effect of concomitant use of varying concentrations of Compound 1 with MK2206 is shown.

Concomitant use of Compound 1 and MK2206 dihydrochloride was observed to enhance a cell growth inhibitory effect dependent on the concentration of each medicine on the endometrial cancer cell line AN3CA having an FGFR2 mutation, as compared with the cell growth inhibitory effect of each medicine alone (FIGS. 8A and 8B). Particularly, concomitant use of Compound 1 and MK2206 dihydrochloride at high concentrations (e.g., the combinations of 0.01 μM or higher of Compound 1 and 0.1 μM or higher of MK2206) was confirmed to have an effect of killing the cells so as to fall below the number of cells at the time of medicine addition, indicating that apoptosis was induced.

From the results described above, it was confirmed that a preferable effect of concomitant use is obtained when Compound 1 or a pharmaceutically acceptable salt thereof is used in the range of 0.001 to 1 moles per mole of MK2206.

Example 9: Evaluation of Effect of Concomitant Use of Compound 1 and AKT Inhibitor (Confirmation of Apoptosis Induction)

<A Materials and Methods>

A human endometrial cancer line AN3CA was cultured using a MEM medium containing 10% fetal bovine serum. The cells were maintained at 37° C. under 5% $CO_2$ and subcultured at a ratio of 1:5 to 1:20 by 1 to 2 passages per week.

<Cell Survival Rate Assay>

The presence or absence of induction of apoptosis by concomitant use was observed using CellEvent™ Caspase-3/7 Green Detection Reagent (Invitrogen Corp.). The cells were collected by an ordinary method, suspended in the above medium containing 10% fetal bovine serum, and seeded in a 12-well plate. The number of cells seeded per well was set to $1 \times 10^6$ cells/800 μL. The cells were incubated at 37° C. for 24 hours under 5% $CO_2$, and then, 100 μL of a medium containing Compound 1 and MK2206 dihydrochloride, or a vehicle was added to each well. The concentration of Compound 1 added was set to a final concentration of 10 nM. The concentration of MK2206 dihydrochloride was set to 300 nM (in terms of a free form). These medicines used alone (DMSO was added as a control) or concomitantly were comparatively studied. After the medicine addition, the cells were incubated at 37° C. for 24 hours under 5% $CO_2$. Apoptosis was detected by adding 1 μL of CellEvent™ Caspase-3/7 Green Detection Reagent (Invitrogen Corp.) solution per well to the cells, incubating the cells at 37° C. for 30 minutes, and then measuring cell images and fluorescence signals in the bright field under a fluorescence microscope. The observed fluorescence signals indicate the induction of Caspase 3/7, and the amplitude of the signals represents the presence or absence of induction of apoptosis-like cell death.

<B Results>

Figure 9:
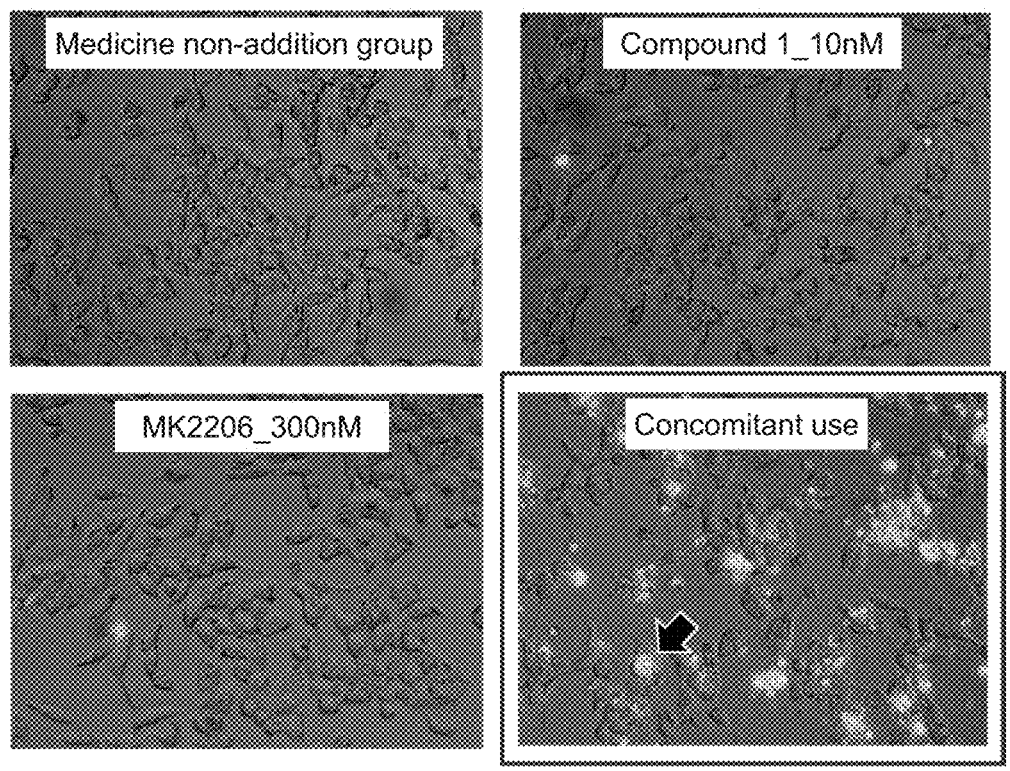
FIG. 9 shows that apoptosis is induced in a human endometrial cancer line AN3CA by concomitant use of an AKT inhibitor MK2206 and Compound 1.

As shown in FIG. 9, the induction of cell death was hardly found in the medicine non-addition group and the cells supplemented with Compound 1 or MK2206 dihydrochloride alone. On the other hand, strong fluorescent staining image indicating the induction of cell death was confirmed in the group supplemented with Compound 1 and MK2206 dihydrochloride, indicating a remarkable apoptosis-inducing effect of concomitant use of both the medicines.

Example 10: Evaluation of Antitumor Effect of Concomitant Use of Compound 1 and AKT Inhibitor or mTOR Inhibitor <A Materials and Methods>

A human endometrial cancer line AN3CA was cultured in a MEM medium containing 10% fetal bovine serum. The cells were maintained at 37° C. under 5% $CO_2$ and subcultured at a ratio of 1:5 to 1:20 by 1 to 2 passages per week.

<Cell Survival Rate Assay>

Cell survival rates were measured using CellTiter-Glo. The cells were collected by an ordinary method, suspended in the above medium containing 10% fetal bovine serum, and seeded in a 96-well plate. The number of cells seeded per well was set to 2000 cells/80 μL. The cells were incubated at 37° C. for 24 hours under 5% $CO_2$, and then, 10 μL of a medium containing Compound 1 and MK2206 dihydrochloride or a mTOR inhibitor everolimus, or a vehicle was added to the cells seeded in each well. The concentration of Compound 1 was set to 10 concentrations in total of a 2-fold dilution series with 0.16 μM as the highest final concentration. The concentration of MK2206 dihydrochloride was set to 10 concentrations in total of a 2-fold dilution series with 6.4 μM (in terms of a free form) as the highest final concentration. The concentration of everolimus was set to 10 concentrations in total of a 2-fold dilution series with 0.032 μM as the highest final concentration. DMSO was added to a control, and each medicine used alone or concomitantly used with Compound 1 was studied. After adding the medicine to the cells, the cells were further incubated at 37° C. for 72 hours under 5% $CO_2$. 100 μL of CellTiter-Glo solution was added to each well, and the cells were incubated at room temperature for 10 minutes, followed by the measurement of chemiluminescence using a plate reader ARVO. Growth inhibitory effects relative to the vehicle group were calculated from the obtained data similarly as in Examples 7 and 8.

The concentration at which each medicine exhibited 50% cell growth inhibitory effect ($IC_{50}$) was determined using median effect analysis software CalcuSyn 2.0 (CalcuSyn, Inc.) similarly as in Example 6. Next, a combination index (CI) value at each combined concentration of the medicines was determined.

Combinations of Compound 1 and MK2206 dihydrochloride or everolimus concentrations that attained Fa=0.4, 0.5, 0.6, 0.7, 0.8, or 0.9 were extracted from the Fa values calculated from the combined Compound 1 and MK2206 dihydrochloride or everolimus concentrations in the AN3CA cells, and applied to linear curve fitting using CalcuSyn to obtain CI.

<B Results>

Figure 10A:
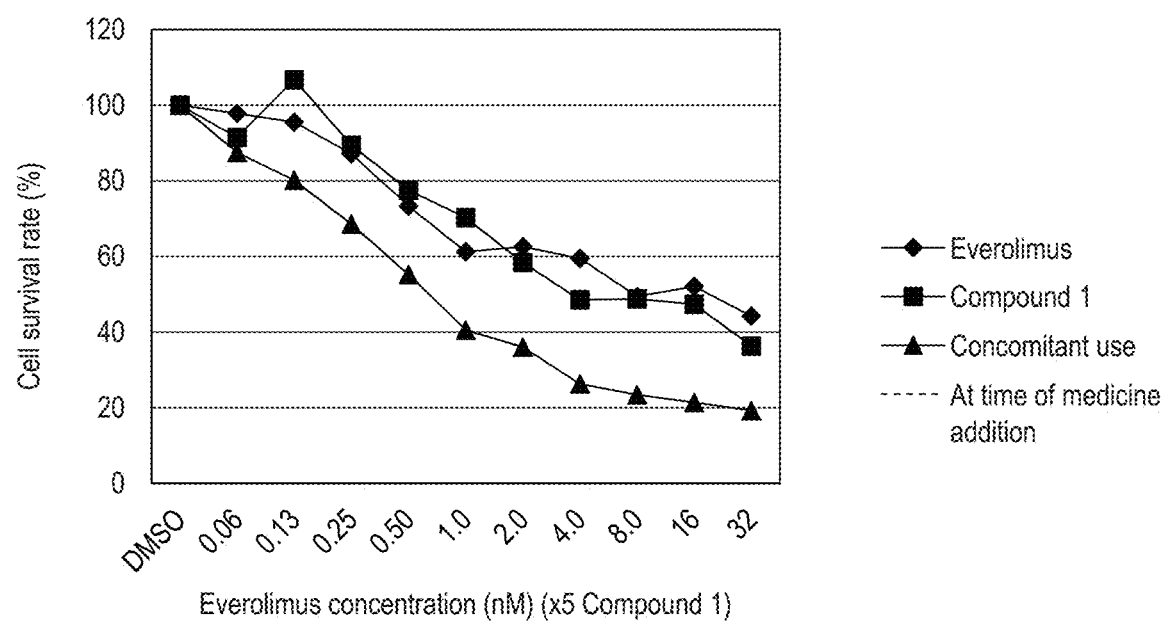
FIG. 10A shows the effect of concomitant use of Compound 1 and everolimus on the cell survival rate of a human endometrial cancer line AN3CA.
Figure 10B:
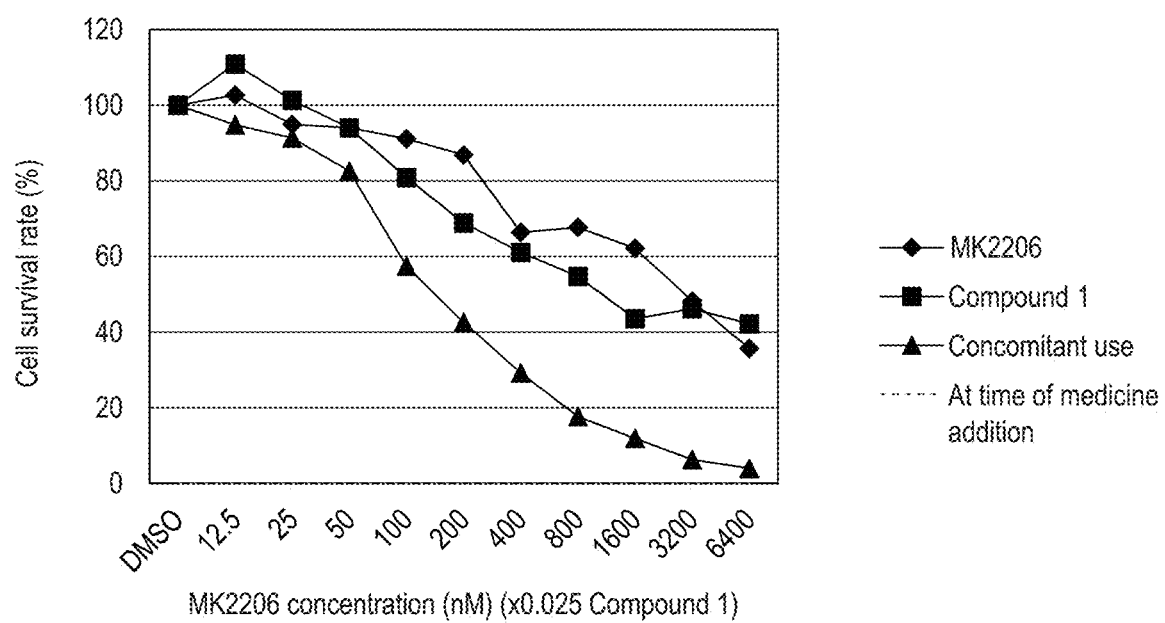
FIG. 10B shows the effect of concomitant use of Compound 1 and MK2206 on the cell survival rate of a human endometrial cancer line AN3CA.

CI values for combinations of Compound 1 and MK2206 dihydrochloride or everolimus concentrations that attained Fa=0.4, 0.5, 0.6, 0.7, 0.8, or 0.9 were calculated and shown in Table 4. In the table, the molar ratios between the medicines are indicated within the parentheses. Concomitant use of Compound 1 and everolimus or MK2206 dihydrochloride was confirmed to exhibit synergistic effects as strong as CI<0.3 in all of the drug effect ranges tested (FIGS. 10A and 10B and Table 4).

From the results described above, it was confirmed that a preferable effect of concomitant use is obtained when Compound 1 or a pharmaceutically acceptable salt thereof is used in the range of 5 moles per mole of everolimus.

It was also confirmed that a preferable effect of concomitant use is obtained when Compound 1 or a pharmaceutically acceptable salt thereof is used at 0.025 moles per mole of MK2206.

TABLE 4

| Medicine | | |
|---|---|---|
| | | Everolimus:Compound 1 (1:5) |
| Fa | 0.4 | 0.270 |
| | 0.5 | 0.264 |
| | 0.6 | 0.260 |
| | 0.7 | 0.257 |
| | 0.8 | 0.255 |
| | 0.9 | 0.258 |
| | | MK2206:Compound 1 (1:0.025) |
| Fa | 0.4 | 0.256 |
| | 0.5 | 0.195 |
| | 0.6 | 0.149 |
| | 0.7 | 0.111 |
| | 0.8 | 0.078 |
| | 0.9 | 0.046 |

Example 11: Influence of Concomitant Use of Compound 1 and AKT Inhibitor or mTOR Inhibitor on MAPK/ERK Pathway and PI3K/AKT Pathway <A Materials and Methods>

A human endometrial cancer line AN3CA was grown in a MEM medium containing 10% fetal bovine serum. The cells were maintained at 37° C. under 5% $CO_2$ and subcultured at a ratio of 1:5 to 1:20 by 1 to 2 passages per week.

<Western Blot>

The intracellular phosphorylation levels of ERK, AKT, mTOR and S6 were detected by Western blot method. The cells were collected by an ordinary method, suspended in the above medium containing 10% fetal bovine serum, and seeded in a 12-well plate. The number of cells seeded per well was set to $1 \times 10^6$ cells/800 µL. The cells were incubated at 37° C. for 24 hours under 5% $CO_2$, and then, 100 µL of a medium containing Compound 1 and MK2206 dihydrochloride or everolimus, or a vehicle was added to each well. Compound 1 was added at final concentrations of 10 and 100 nM to the cells. Likewise, MK2206 dihydrochloride was added at a final concentration of 5 µM (in terms of a free form), and everolimus was added at a final concentration of 3 nM. Each medicine alone and each combination were studied. DMSO was added as a control at a final concentration of 0.2%.

The cells were incubated at 37° C. for 2 hours under 5% $CO_2$. Then, cell lysates were prepared using RIPA Buffer [composition: 50 mM Tris-HCl (pH 8.0), 150 mM NaCl, 5 mM EDTA, 1% (w/w) Nonidet P-40, 0.1% (w/w) sodium deoxycholate, and 0.1% (w/w) SDS]. The amounts of phosphorylated AKT, phosphorylated ERK, phosphorylated mTOR, phosphorylated S6 and GAPDH were detected using Western blot according to an ordinary method.

<B Results>

Figure 11:
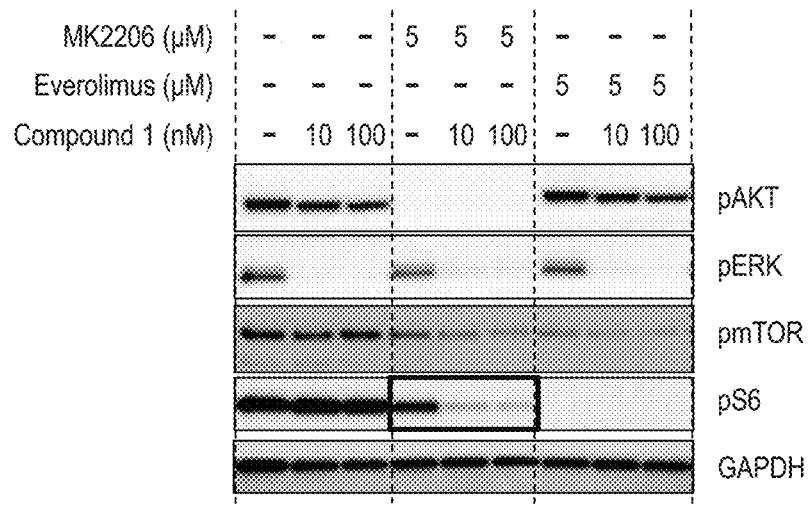
FIG. 11 shows the effect of concomitant use of Compound 1 and everolimus or MK2206 on the phosphorylation of proteins AKT, ERK, mTOR and S6 in a human endometrial cancer line AN3CA.

As shown in FIG. 11, Compound 1 at both the concentrations of 10 and 100 nM strongly inhibited the phosphorylation of ERK in the AN3CA cells treated with Compound 1 for 24 hours. On the other hand, the treatment with MK2206 dihydrochloride or everolimus alone inhibited AKT phosphorylation or mTOR phosphorylation, respectively. Concomitant use of Compound 1 and MK2206 dihydrochloride inhibited both the phosphorylation of ERK and the phosphorylation of AKT. Particularly, strong inhibition of S6 protein phosphorylation was confirmed only in the concomitant use. As for concomitant use of Compound 1 and everolimus, the co-inhibition of ERK phosphorylation and S6 protein phosphorylation was observed only in the concomitant use of both the medicines.

From the results described above, it was confirmed that a preferable effect of concomitant use is obtained when Compound 1 or a pharmaceutically acceptable salt thereof is used in the range of 0.002 to 0.02 moles per mole of everolimus.

It was also confirmed that a preferable effect of concomitant use is obtained when Compound 1 or a pharmaceutically acceptable salt thereof is used in the range of 0.002 to 0.02 moles per mole of MK2206.

Example 12: Activation of FGF/FGFR Pathway Responsible for Resistance to EGFR Inhibitor, and Influence of Addition of Compound 1 Thereon <A Materials and Methods>

Human lung cancer lines HCC4006 (available from American Type Culture Collection), NCI-H1650 (available from American Type Culture Collection), and NCI-H322 (available from DS Pharma Biomedical Co., Ltd.) were cultured using an RPMI medium containing 10% fetal bovine serum. The cells of each line were maintained at 37° C. under 5% $CO_2$ and subcultured at a ratio of 1:5 to 1:20 by 1 to 2 passages per week.

<Cell Survival Rate Assay>

Cell survival rates were measured using CellTiter-Glo. The cells were recovered by an ordinary method, suspended in the above medium containing 10% fetal bovine serum, and seeded in a 96-well plate. The number of cells seeded per well was set to 2000 cells/70 µL. The cells were incubated at 37° C. for 24 hours under 5% $CO_2$, and then, 10 µL of a medium containing Compound 1, an EGFR inhibitor gefitinib, a vehicle (DMSO), or 2 medicines of Compound 1 and gefitinib was added to each well. In order to study effects on the activated FGF/FGFR pathway in the cells, a ligand FGF2 or FGF7 was added to the cells and compared with non-addition. The concentrations of Compound 1 and gefitinib were set to 10 concentrations in total of 3-fold dilution series with 100 nM and 10 µM, respectively, as the highest final concentrations. DMSO was added to a control well, and 10 ng/mL FGF2 or 100 ng/mL FGF7 was added to the medium.

The cells were incubated at 37° C. for 72 hours under 5% $CO_2$. Then, 100 µL of CellTiter-Glo solution was added to each well, and the cells were incubated at room temperature for 10 minutes, followed by the measurement of chemiluminescence intensity using a plate reader (ARVO). Growth inhibitory effects relative to the vehicle group were calculated from the obtained data.

<B Results>

Figure 12B:
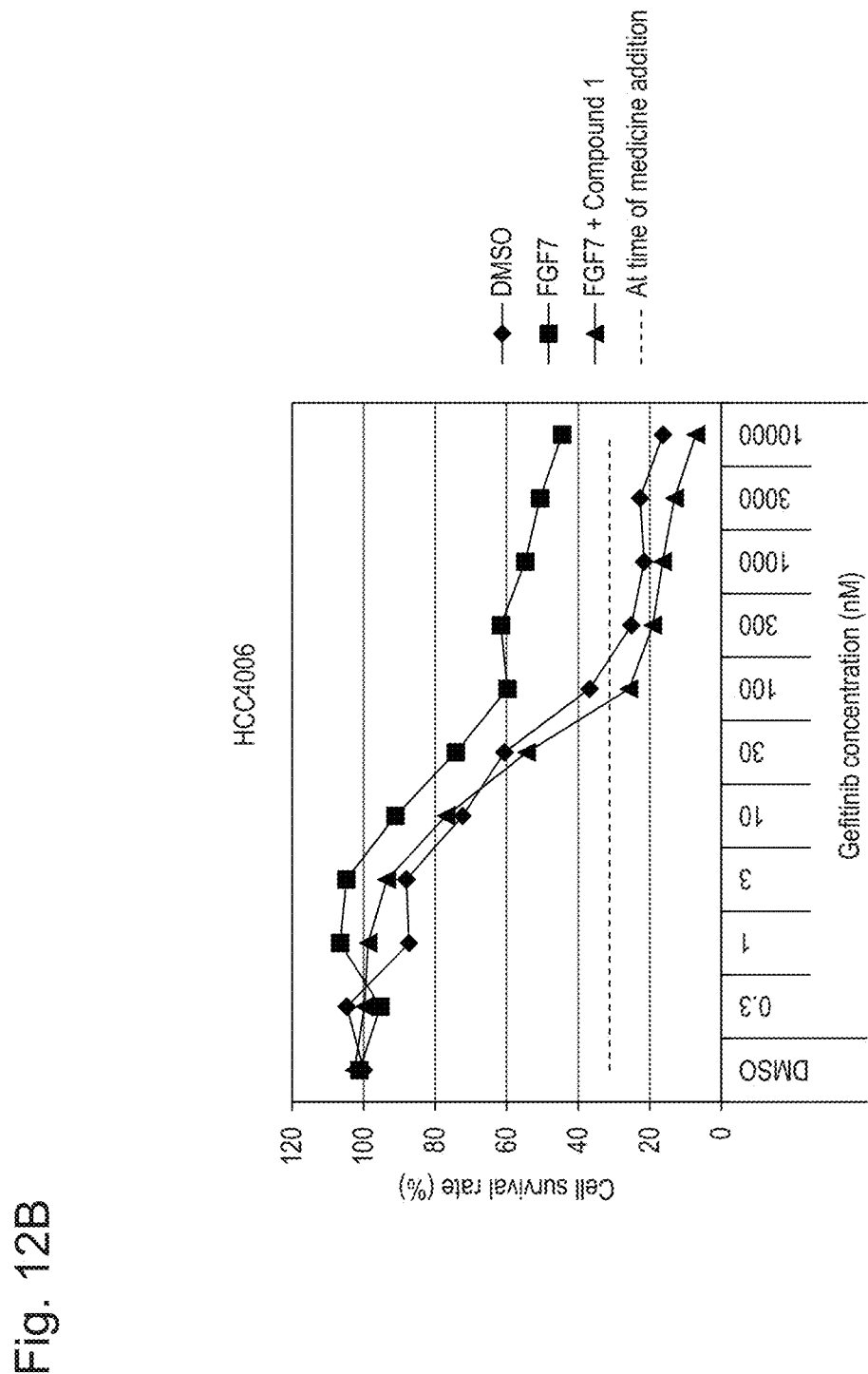
FIG. 12B shows the effect of concomitant use of Compound 1 and gefitinib on the cell survival rate of HCC4006 cell line.
Figure 12C:
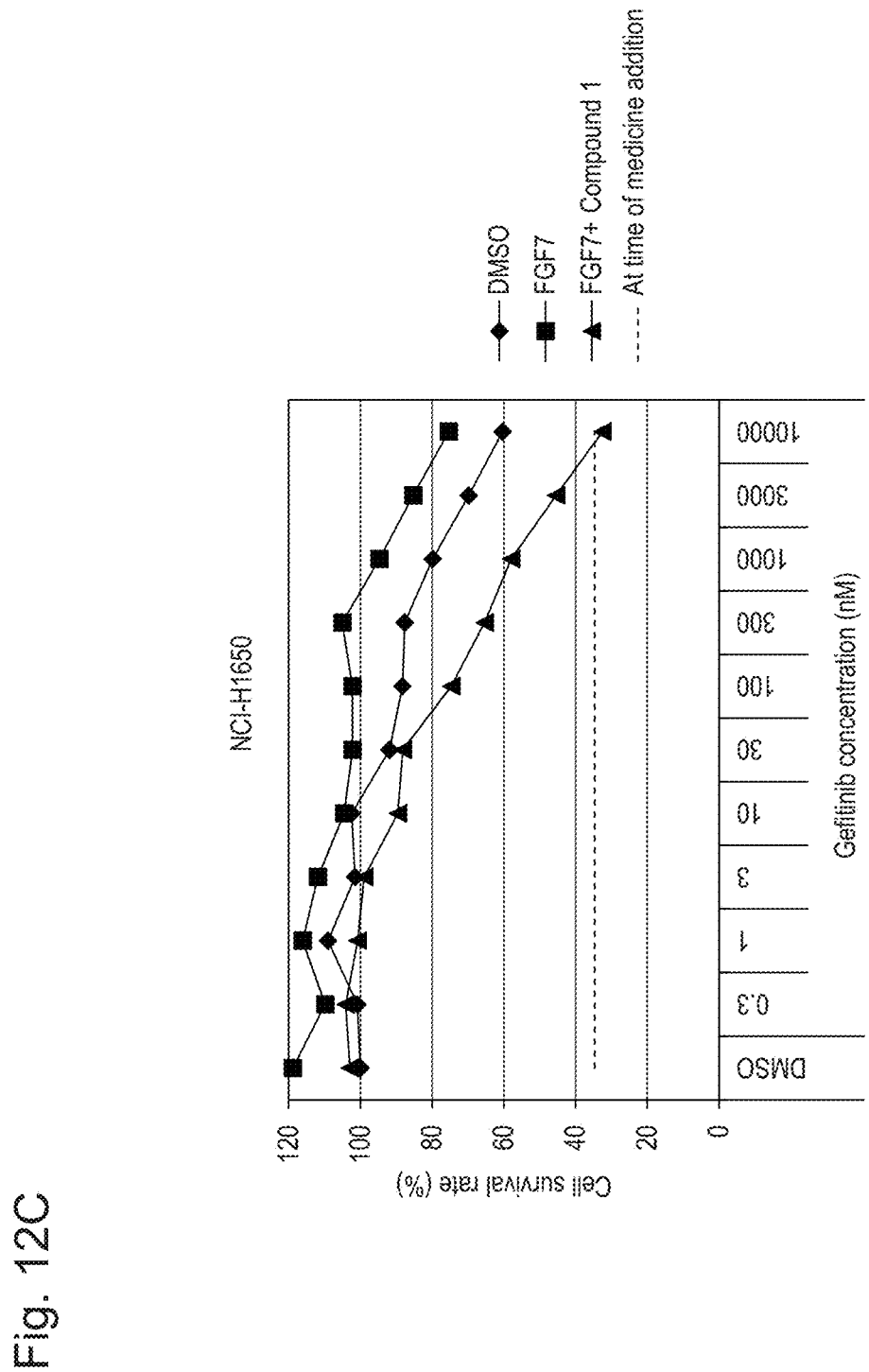
FIG. 12C shows the effect of concomitant use of Compound 1 and gefitinib on the cell survival rate of NCI-H1650 cell line.
Figure 12D:
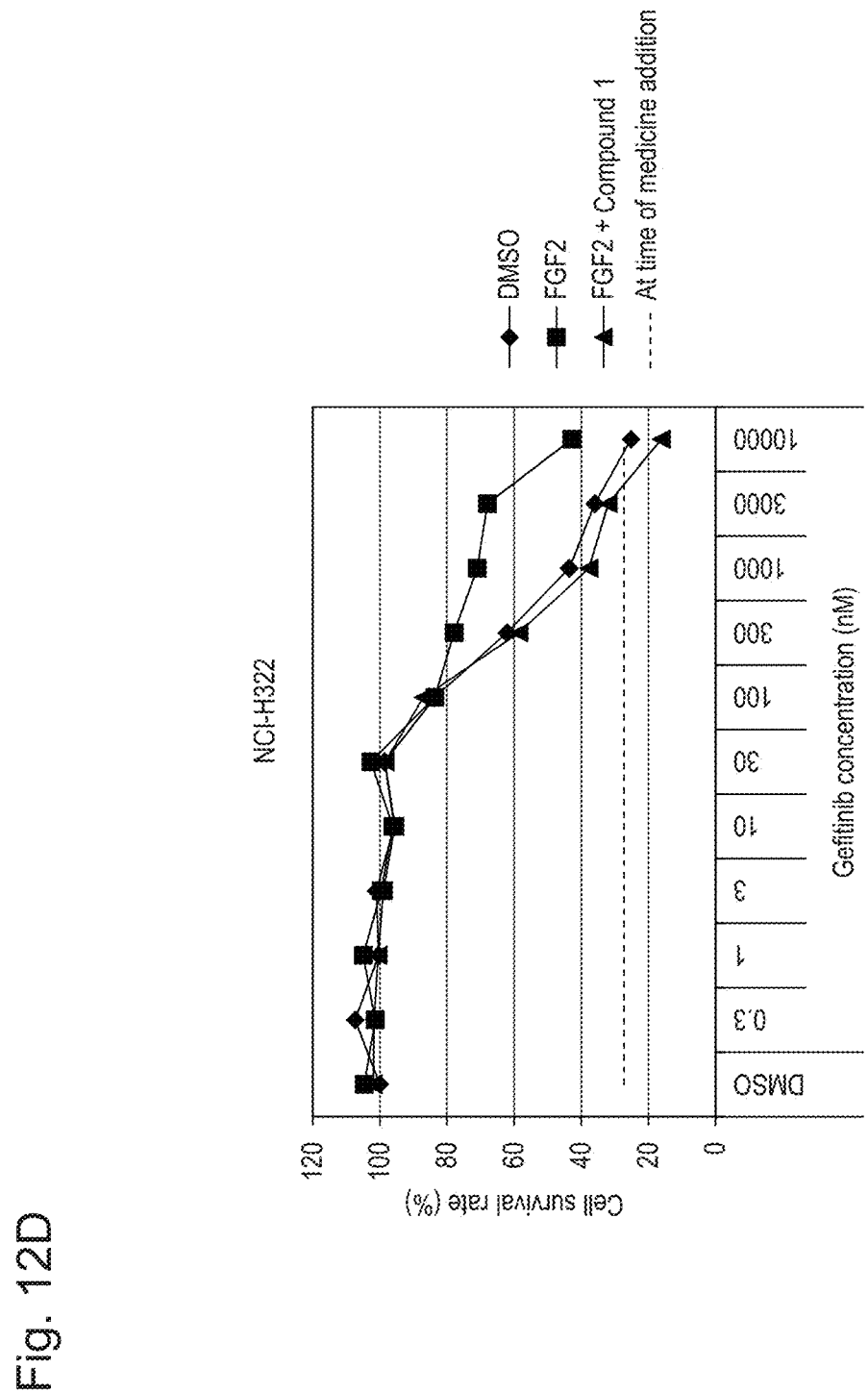
FIG. 12D shows the effect of concomitant use of Compound 1 and gefitinib on the cell survival rate of NCI-H322 cell line.

The lung cancer-derived HCC4006 and NCI-H1650 lines were deficient in EGFR inhibitor-sensitive EGFR exon 9 (FIG. 12A). The addition of the FGFR ligand FGF7 attenuated the drug effect of gefitinib (FIGS. 12B and 12C). When the FGFR activation by FGF addition was inhibited by adding Compound 1 thereto, the effect of gefitinib was restored to the same level as in ligand non-addition, or further enhanced. Similar effects of Compound 1 were found in the FGFR-expressing line NCI-H322 having no EGFR mutation (FIG. 12D). These results demonstrated that concomitant use of Compound 1 and an EGFR inhibitor is effective for lung cancer in which FGF/FGFR signals are responsible for resistance or low sensitivity to the EGFR inhibitor.

From the results described above, it was confirmed that a preferable effect of concomitant use is obtained when Compound 1 or a pharmaceutically acceptable salt thereof is used in the range of 0.01 to 1 moles per mole of gefitinib.

INDUSTRIAL APPLICABILITY

The present invention can remarkably enhance an antitumor effect as compared with the administration of a conventionally known antitumor agent alone, and is also effective for tumors having drug resistance; thus can greatly expand the possibility of chemotherapy for malignant tumors.

All publications, patents and patent applications cited herein are incorporated herein by reference in their entirety.

The invention claimed is:

1. A method for treating a tumor comprising administering
   a) (S)-1-(3-(4-amino-3-((3,5-dimethoxyphenyl)ethynyl)-1H-pyrazolo[3,4-d]pyrimidin-1-yl)pyrrolidin-1-yl) prop-2-en-1-one or a pharmaceutically acceptable salt thereof, and
b) one or more additional compound(s) having an antitumor effect or pharmaceutically acceptable salt(s) thereof, selected from the group consisting of tegafur/gimeracil/oteracil potassium, 5-fluorouracil, gemcitabine, paclitaxel, cisplatin, everolimus, 8-[4-(1-aminocyclobutyl)phenyl]-9-phenyl-1,2,4-triazolo[3,4-f][1,6]naphthyridin-3(2H)-one, and gefitinib,
to a patient in need thereof.

2. A method for enhancing the antitumor effect of one or more compound(s) having an antitumor effect or pharmaceutically acceptable salt(s) thereof, selected from the group consisting of tegafur/gimeracil/oteracil potassium, 5-fluorouracil, gemcitabine, paclitaxel, cisplatin, everolimus, 8-[4-(1-aminocyclobutyl)phenyl]-9-phenyl-1,2,4-triazolo[3,4-f][1,6]naphthyridin-3(2H)-one, and gefitinib, comprising administering said compound with (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or a pharmaceutically acceptable salt thereof.

3. The method according to claim 1, wherein the tumor is selected from the group consisting of lung cancer, esophagus cancer, gastric cancer, duodenum cancer, liver cancer, hepatocellular cancer, biliary tract cancer, pancreatic cancer, colorectal cancer, breast cancer, uterine cancer, ovarian cancer, renal cancer, bladder cancer, prostate cancer, testicular tumor, thyroid cancer, bone or soft tissue tumor, leukemia, malignant lymphoma, multiple myeloma, head and neck cancer, brain tumor, and skin cancer.

4. The method according to claim 3, wherein the tumor is selected from the group consisting of gastric cancer, biliary tract cancer, uterine cancer, bladder cancer, and brain tumor.

5. The method according to claim 3, wherein the tumor is gastric cancer and the additional compound having antitumor effect or the pharmaceutically salt thereof is selected from the group consisting of paclitaxel, tegafur/gimeracil/oteracil potassium, 5-fluorouracil, gemcitabine, and cisplatin.

6. The method according to claim 3, wherein the tumor is biliary tract cancer and the additional compound having an antitumor effect or the pharmaceutically acceptable salt thereof is selected from the group consisting of gemcitabine and cisplatin.

7. The method according to claim 3, wherein the tumor is uterine cancer and the additional compound having an antitumor effect or the pharmaceutically acceptable salt thereof is selected from the group consisting of 5-fluorouracil, gemcitabine, cisplatin, and paclitaxel.

8. The method according to claim 3, wherein the tumor is endometrial cancer, and the additional compound having an antitumor effect or the pharmaceutically acceptable salt thereof is selected from the group consisting of 5-fluorouracil, gemcitabine, cisplatin, and paclitaxel.

9. The method according to claim 1, wherein the tumor to be treated has a mutation in FGFR.

10. The method according to claim 1, wherein the tumor to be treated is resistant to the additional compound having an antitumor effect.

11. The method according to claim 1, wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or a pharmaceutically acceptable salt thereof, and the additional compound having an antitumor effect or a pharmaceutically acceptable salt thereof are administered simultaneously, separately, or sequentially.

12. The method according to claim 1, wherein one or more additional compound(s) having an antitumor effect or pharmaceutically acceptable salt(s) thereof is an antimetabolite.

13. The method according to claim 1, wherein one or more additional compound(s) having an antitumor effect or pharmaceutically acceptable salt(s) thereof is selected from the group consisting of tegafur/gimeracil/oteracil potassium, 5-fluorouracil, and gemcitabine.

14. The method according to claim 1, wherein said one or more additional compound(s) having an antitumor effect or pharmaceutically acceptable salt(s) thereof is tegafur/gimeracil/oteracil potassium.

15. The method according to claim 14, wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.1 to 2 moles per mole of the tegafur.

16. The method according to claim 1, wherein said one or more additional compound(s) having an antitumor effect or pharmaceutically acceptable salt(s) thereof is 5-fluorouracil.

17. The method according to claim 16, wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.0001 to 1 moles per mole of the 5-fluorouracil.

18. The method according to claim 1, wherein one or more additional compound(s) having an antitumor effect or pharmaceutically acceptable salt(s) thereof is gemcitabine.

19. The method according to claim 18, wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.001 to 1 moles per mole of the gemcitabine.

20. The method according to claim 1, wherein said one or more additional compound(s) having an antitumor effect or pharmaceutically acceptable salt(s) thereof is an alkaloid antitumor agent.

21. The method according to claim 1, wherein said one or more additional compound(s) having an antitumor effect or pharmaceutically acceptable salt(s) thereof is paclitaxel.

22. The method according to claim 21, wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.1 to 10 moles per mole of the paclitaxel.

23. The method according to claim 1, wherein said one or more additional compound(s) having an antitumor effect or pharmaceutically acceptable salt(s) thereof is a molecular targeting drug.

24. The method according to claim 1, wherein said one or more additional compound(s) having an antitumor effect or pharmaceutically acceptable salt(s) thereof is selected from the group consisting of everolimus, 8-[4-(1-aminocyclobutyl)phenyl]-9-phenyl-1,2,4-triazolo[3,4-f][1,6]naphthyridin-3(2H)-one, gefitinib, and pharmaceutically acceptable salts thereof.

25. The method according to claim 1, wherein said one or more additional compound(s) having an antitumor effect or pharmaceutically acceptable salt(s) thereof is everolimus.

26. The method according to claim 25, wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 1 to 100 moles per mole of the everolimus.

27. The method according to claim 1, wherein said one or more additional compound(s) having an antitumor effect or pharmaceutically acceptable salt(s) thereof is 8-[4-(1-aminocyclobutyl)phenyl]-9-phenyl-1,2,4-triazolo[3,4-f][1,6]naphthyridin-3(2H)-one or the pharmaceutically acceptable salt thereof.

28. The method according to claim 27, wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.001 to 1000 moles per mole of the 8-[4-(1-aminocyclobutyl)phenyl]-9-phenyl-1,2,4-triazolo[3,4-f][1,6]naphthyridin-3(2H)-one.

29. The method according to claim 1, wherein said one or more additional compound(s) having an antitumor effect or pharmaceutically acceptable salt(s) thereof is gefitinib or a pharmaceutically acceptable salt thereof.

30. The method according to claim 29, wherein the (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or the pharmaceutically acceptable salt thereof is administered at 0.001 to 1000 moles per mole of the gefitinib.

* * * * *

UNITED STATES PATENT AND TRADEMARK OFFICE
CERTIFICATE OF CORRECTION

PATENT NO. : 11,975,002 B2
APPLICATION NO. : 16/082117
DATED : May 7, 2024
INVENTOR(S) : Miura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 403 days.

Signed and Sealed this
Twelfth Day of November, 2024

*Katherine Kelly Vidal*

Katherine Kelly Vidal
*Director of the United States Patent and Trademark Office*